US009113789B2

(12) United States Patent
Wenzel et al.

(10) Patent No.: US 9,113,789 B2
(45) Date of Patent: *Aug. 25, 2015

(54) SYSTEM AND METHOD FOR ESTIMATING ELECTRICAL CONDUCTION DELAYS FROM IMMITTANCE VALUES MEASURED USING AN IMPLANTABLE MEDICAL DEVICE

(75) Inventors: Brian Jeffrey Wenzel, San Jose, CA (US); Dorin Panescu, San Jose, CA (US); Mihir Naware, San Jose, CA (US); Jeffery Siou, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 571 days.

This patent is subject to a terminal disclaimer.

(21) Appl. No.: 13/485,512

(22) Filed: May 31, 2012

(65) Prior Publication Data
US 2013/0137999 A1    May 30, 2013

Related U.S. Application Data

(62) Division of application No. 12/127,963, filed on May 28, 2008, now Pat. No. 8,208,999.

(51) Int. Cl.
*A61B 5/02*      (2006.01)
*A61B 5/0215*   (2006.01)
(Continued)

(52) U.S. Cl.
CPC .............. *A61B 5/0215* (2013.01); *A61B 5/002* (2013.01); *A61B 5/0002* (2013.01); *A61B 5/053* (2013.01);
(Continued)

(58) Field of Classification Search
CPC ...... A61B 5/7405; A61B 5/746; A61B 5/742; A61B 5/053; A61B 5/0215; A61B 5/0031; A61B 5/686

USPC .................................................. 600/481–504
See application file for complete search history.

(56) References Cited

U.S. PATENT DOCUMENTS

| 3,934,458 A | 1/1976 | Beretsky |
| 4,390,021 A | 6/1983 | Spurrell |

(Continued)

FOREIGN PATENT DOCUMENTS

| EP | 1629863 | 3/2006 |
| WO | 96/15827 | 5/1996 |

(Continued)

OTHER PUBLICATIONS

Helfant et al., "Effect of Sustained Isometric Handgrip Exercise on Left Ventricular Performance," Circulation. 1971;44:982.

(Continued)

*Primary Examiner* — Patricia Mallari
*Assistant Examiner* — Tiffany Weston
(74) *Attorney, Agent, or Firm* — Theresa A. Raymer

(57) ABSTRACT

Techniques are provided for estimating electrical conduction delays with the heart of a patient based on measured immittance values. In one example, impedance or admittance values are measured within the heart of a patient by a pacemaker or other implantable medical device, then used by the device to estimate cardiac electrical conduction delays. A first set of predetermined conversion factors may be used to convert the measured immittance values into conduction delay values. In some examples, the device then uses the estimated conduction delay values to estimate LAP or other cardiac pressure values. A second set of predetermined conversion factors may be used to convert the estimated conduction delays into pressure values. Techniques are also described for adaptively adjusting pacing parameters based on estimated LAP.

23 Claims, 26 Drawing Sheets

OVERVIEW OF TECHNIQUE FOR ESTIMATING CARDIAC PRESSURE

MEASURE AN ELECTRICAL CONDUCTION DELAY IN THE HEART OF THE PATIENT WHERE THE DELAY IS AFFECTED BY CARDIAC PRESSURE SUCH AS LEFT ATRIAL PRESSURE (LAP)    50

ESTIMATE LAP OR OTHER SUITABLE CARDIAC PERFORMANCE PARAMETERS WITHIN THE PATIENT FROM THE ELECTRICAL CONDUCTION DELAY    52

(51) Int. Cl.
    *A61B 5/053* (2006.01)
    *A61N 1/365* (2006.01)
    *A61B 5/00* (2006.01)

(52) U.S. Cl.
    CPC .............. *A61B 5/4839* (2013.01); *A61B 5/686* (2013.01); *A61B 5/7278* (2013.01); *A61B 5/7282* (2013.01); *A61B 5/742* (2013.01); *A61B 5/7405* (2013.01); *A61B 5/746* (2013.01); *A61N 1/36521* (2013.01); *A61B 2560/0223* (2013.01)

(56) References Cited

U.S. PATENT DOCUMENTS

| | | | | |
|---|---|---|---|---|
| 4,393,877 | A | 7/1983 | Imran | |
| 4,535,774 | A | 8/1985 | Olson | |
| 4,686,987 | A | 8/1987 | Salo et al. | |
| 4,873,987 | A | 10/1989 | Djordjevich | |
| 4,938,228 | A | 7/1990 | Righter | |
| 4,969,465 | A | 11/1990 | Pless | |
| 4,971,058 | A | 11/1990 | Pless | |
| 5,003,976 | A | 4/1991 | Alt | 607/18 |
| 5,042,303 | A | 8/1991 | Geluk | |
| 5,054,485 | A | 10/1991 | Cohen | |
| 5,065,759 | A | 11/1991 | Begemann | |
| 5,105,810 | A | 4/1992 | Collins | |
| 5,119,813 | A | 6/1992 | Cohen | |
| 5,133,350 | A | 7/1992 | Duffin | |
| 5,144,949 | A | 9/1992 | Olson | |
| 5,156,148 | A | 10/1992 | Cohen | |
| 5,179,946 | A | 1/1993 | Weiss | |
| 5,184,614 | A | 2/1993 | Collins | |
| 5,201,865 | A | 4/1993 | Kuehn | |
| 5,282,840 | A | 2/1994 | Hurdlik | |
| 5,284,491 | A | 2/1994 | Sutton | |
| 5,292,340 | A | 3/1994 | Crosby | |
| 5,300,093 | A | 4/1994 | Koestner et al. | |
| 5,305,745 | A | 4/1994 | Zacouto | |
| 5,327,900 | A | 7/1994 | Mason | |
| 5,330,505 | A | 7/1994 | Cohen | |
| 5,334,222 | A * | 8/1994 | Salo et al. | 607/17 |
| 5,391,190 | A | 2/1995 | Pederson | |
| 5,417,717 | A | 5/1995 | Salo | |
| 5,476,483 | A | 12/1995 | Bornzin et al. | 607/17 |
| 5,476,484 | A | 12/1995 | Hedberg | |
| 5,507,785 | A | 4/1996 | Deno | |
| 5,531,772 | A | 7/1996 | Prutchi | |
| 5,676,141 | A | 10/1997 | Hollub | 600/323 |
| 5,690,611 | A | 11/1997 | Swartz | |
| 5,713,935 | A | 2/1998 | Prutchi | |
| 5,720,769 | A | 2/1998 | Van Ort | |
| 5,738,104 | A | 4/1998 | Lo | |
| 5,746,214 | A | 5/1998 | Brown | |
| 5,792,194 | A | 8/1998 | Morra | |
| 5,800,467 | A | 9/1998 | Park et al. | |
| 5,814,088 | A | 9/1998 | Paul | |
| 5,836,985 | A | 11/1998 | Rostami et al. | 607/14 |
| 5,954,752 | A | 9/1999 | Mongeon | |
| 5,957,861 | A | 9/1999 | Combs | |
| 6,044,297 | A | 3/2000 | Sheldon et al. | 607/17 |
| 6,081,747 | A | 6/2000 | Levine | |
| 6,198,965 | B1 | 3/2001 | Penner | |
| 6,208,900 | B1 | 3/2001 | Ecker | |
| 6,219,579 | B1 | 4/2001 | Bakels | |
| 6,223,082 | B1 | 4/2001 | Bakels et al. | 607/17 |
| 6,249,705 | B1 | 6/2001 | Snell | 607/59 |
| 6,251,303 | B1 | 6/2001 | Bawendi | |
| 6,275,727 | B1 | 8/2001 | Hopper | |
| 6,278,894 | B1 | 8/2001 | Salo et al. | |
| 6,285,907 | B1 | 9/2001 | Kramer | |
| 6,317,626 | B1 | 11/2001 | Warman | |
| 6,328,699 | B1 | 12/2001 | Eigler et al. | 600/486 |
| 6,337,994 | B1 | 1/2002 | Stoianovici | |
| 6,411,848 | B2 | 6/2002 | Kramer | |
| 6,424,865 | B1 | 7/2002 | Ding | 607/9 |
| 6,438,408 | B1 | 8/2002 | Mulligan et al. | 600/510 |
| 6,459,929 | B1 | 10/2002 | Hopper | |
| 6,473,640 | B1 | 10/2002 | Eriebacher | |
| 6,473,647 | B1 | 10/2002 | Bradley | |
| 6,477,420 | B1 | 11/2002 | Struble | |
| 6,480,733 | B1 | 11/2002 | Turcott | 600/516 |
| 6,501,983 | B1 | 12/2002 | Natarajan et al. | |
| 6,508,771 | B1 | 1/2003 | Padmanabhan | |
| 6,512,949 | B1 | 1/2003 | Combs | |
| 6,512,952 | B2 | 1/2003 | Stahmann et al. | 607/9 |
| 6,522,923 | B1 | 2/2003 | Turcott | 607/27 |
| 6,527,729 | B1 | 3/2003 | Turcott | |
| 6,539,261 | B2 | 3/2003 | Dal Molin | |
| 6,572,557 | B2 | 6/2003 | Tchou et al. | 600/483 |
| 6,595,927 | B2 | 7/2003 | Pitss-Crick | |
| 6,620,186 | B2 | 9/2003 | Saphon | |
| 6,628,988 | B2 | 9/2003 | Kramer et al. | 607/9 |
| 6,643,546 | B2 | 11/2003 | Mathis et al. | 607/9 |
| 6,643,548 | B1 | 11/2003 | Mai et al. | 607/17 |
| 6,645,153 | B2 | 11/2003 | Kroll et al. | 600/481 |
| 6,668,194 | B2 | 12/2003 | VanHout | |
| 6,714,811 | B1 | 3/2004 | Padmanabhan | |
| 6,741,885 | B1 | 5/2004 | Park et al. | 600/509 |
| 6,748,261 | B1 | 6/2004 | Kroll | 600/510 |
| 6,754,530 | B2 | 6/2004 | Bakels | |
| 6,763,267 | B2 | 7/2004 | Ding | 607/9 |
| 6,904,313 | B1 | 6/2005 | Snell | |
| 6,970,742 | B2 | 11/2005 | Mann et al. | 607/23 |
| 7,027,866 | B2 | 4/2006 | Warkentin | |
| 7,065,400 | B2 | 6/2006 | Schechter | |
| 7,065,403 | B1 | 6/2006 | Mouchawar | |
| 7,115,095 | B2 | 10/2006 | Eigler et al. | 600/486 |
| 7,127,290 | B2 | 10/2006 | Girouard | |
| 7,139,609 | B1 | 11/2006 | Min | |
| 7,139,610 | B2 | 11/2006 | Ferek-Petric | |
| 7,142,918 | B2 | 11/2006 | Stahmann | |
| 7,149,568 | B2 | 12/2006 | Amano | |
| 7,181,283 | B2 | 2/2007 | Hettrick | |
| 7,184,821 | B2 | 2/2007 | Belalcazar | |
| 7,192,401 | B2 | 3/2007 | Saalasti | |
| 7,200,442 | B1 | 4/2007 | Koh | |
| 7,248,925 | B2 | 7/2007 | Bruhns et al. | 607/25 |
| 7,251,524 | B1 | 7/2007 | Hepp et al. | |
| 7,272,443 | B2 | 9/2007 | Min et al. | |
| 7,330,752 | B2 | 2/2008 | Kettunen | |
| 7,410,467 | B2 | 8/2008 | Cooper | |
| 7,483,743 | B2 | 1/2009 | Mann | |
| 7,488,290 | B1 | 2/2009 | Stahmann | |
| 7,590,449 | B2 | 9/2009 | Mann | |
| 7,616,991 | B2 | 11/2009 | Mann | |
| 7,794,404 | B1 | 9/2010 | Gutfinger et al. | |
| 8,600,497 | B1 | 12/2013 | Yang et al. | |
| 8,712,519 | B1 | 4/2014 | Panescu et al. | |
| 2001/0016759 | A1 | 8/2001 | Kramer | |
| 2001/0051774 | A1 | 12/2001 | Littrup | |
| 2002/0002389 | A1 | 1/2002 | Bradley | |
| 2002/0022785 | A1 | 2/2002 | Romano | |
| 2002/0082648 | A1 | 6/2002 | Kramer | |
| 2002/0082660 | A1 | 6/2002 | Stahmann | |
| 2003/0069610 | A1 | 4/2003 | Kramer | |
| 2003/0083712 | A1 | 5/2003 | Rueter | |
| 2003/0144703 | A1 | 7/2003 | Yu et al. | |
| 2003/0220556 | A1 | 11/2003 | Porat | |
| 2004/0015196 | A1 | 1/2004 | Holmstrom | |
| 2004/0019285 | A1 | 1/2004 | Eigler et al. | 600/488 |
| 2004/0059220 | A1 | 3/2004 | Mourad | |
| 2004/0064161 | A1 | 4/2004 | Gunderson | |
| 2004/0147969 | A1 | 7/2004 | Mann et al. | 607/17 |
| 2004/0215097 | A1 | 10/2004 | Wang | |
| 2004/0220640 | A1 | 11/2004 | Burnes | |
| 2004/0230112 | A1 | 11/2004 | Scholz | |
| 2005/0038477 | A1 | 2/2005 | Kramer et al. | |
| 2005/0096551 | A1 | 5/2005 | Baruch | |
| 2005/0124908 | A1 | 6/2005 | Belalcazar | |
| 2005/0125041 | A1 | 6/2005 | Min et al. | 607/9 |
| 2005/0131480 | A1 | 6/2005 | Kramer et al. | |
| 2005/0165456 | A1 | 7/2005 | Mann et al. | 607/30 |
| 2005/0177194 | A1 | 8/2005 | Bjorling | 607/9 |

(56) References Cited

U.S. PATENT DOCUMENTS

| | | | |
|---|---|---|---|
| 2005/0187585 A1 | 8/2005 | Mussig | |
| 2005/0215914 A1 | 9/2005 | Bornzin et al. | |
| 2005/0283091 A1 | 12/2005 | Kink et al. | |
| 2006/0009810 A1 | 1/2006 | Mann et al. | 607/17 |
| 2006/0025828 A1 | 2/2006 | Armstrong | |
| 2006/0079793 A1* | 4/2006 | Mann et al. | 600/486 |
| 2006/0129196 A1 | 6/2006 | Dong | |
| 2006/0135886 A1 | 6/2006 | Lippert et al. | |
| 2006/0136002 A1 | 6/2006 | Sheth et al. | |
| 2006/0149324 A1 | 7/2006 | Mann et al. | 607/9 |
| 2006/0149330 A1 | 7/2006 | Mann et al. | 607/34 |
| 2006/0149331 A1 | 7/2006 | Mann et al. | 607/34 |
| 2006/0184060 A1 | 8/2006 | Belalcazar | |
| 2006/0235480 A1 | 10/2006 | Schechter | |
| 2006/0241512 A1 | 10/2006 | Kwok | |
| 2006/0293609 A1 | 12/2006 | Stahmann | |
| 2008/0009759 A1 | 1/2008 | Chetham | |
| 2008/0033498 A1 | 2/2008 | Mann et al. | |
| 2008/0221477 A1 | 9/2008 | Olson | |
| 2009/0018597 A1 | 1/2009 | Wenzel et al. | |
| 2009/0287267 A1 | 11/2009 | Wenzel et al. | |

FOREIGN PATENT DOCUMENTS

| | | | |
|---|---|---|---|
| WO | 96/19260 | 6/1996 | |
| WO | 98/07467 | 2/1998 | |
| WO | 01/13792 | 3/2001 | |
| WO | 01/32260 | 5/2001 | |
| WO | 01/87410 A2 | 11/2001 | |
| WO | 01/87410 A3 | 11/2001 | |
| WO | 02051496 A2 | 7/2002 | |
| WO | 02051496 A3 | 7/2002 | |
| WO | WO 03/105952 | 12/2003 | A61N 1/368 |
| WO | 2004096041 A2 | 11/2004 | |
| WO | 2004096041 A3 | 11/2004 | |
| WO | 2004105862 | 12/2004 | |
| WO | WO 2005/000206 | 1/2005 | |
| WO | 2006104868 | 10/2006 | |
| WO | WO 2006/135291 | 12/2006 | A61N 1/362 |

OTHER PUBLICATIONS

McClean et al., "Noninvasive calibration of cardiac pressure transducers in patients with heart failure: An aid to implantable hemodynamic monitoring and therapeutic guidance", Journal of Cardiac Failure, vol. 12 No. 7 2006, pp. 568-576.
Helfant et al., "Effect of Sustained Isometric Handgrip Exercise on Left Ventricular Performance," Circulation 1971;44:982.
Stutz, Michael. "All about Circuits: Conductance." Copyright 1999-2000. <http://www.allaboutcircuits.com/vol_1/chpt_5/4.html>.
Notice of Allowance mailed Mar. 30, 2012; Related U.S. Appl. No. 12/127,963.
Terminal Disclaimer filed Dec. 2, 2011; Related U.S. Appl. No. 12/127,963.
Amendment filed Dec. 2, 2011; Related U.S. Appl. No. 12/127,963.
Non-Final Office Action mailed Sep. 2, 2011; Related U.S. Appl. No. 12/127,963.
Notice of Allowance mailed May 13, 2013; Related U.S. Appl. No. 11/779,350.
Terminal Disclaimer filed May 1, 2013; Related U.S. Appl. No. 11/779,350.
Amendment filed May 1, 2013; Related U.S. Appl. No. 11/779,350.
Non-Final Office Action mailed Apr. 24, 2013; Related U.S. Appl. No. 11/779,350.
Notice of Appeal filed Mar. 14, 2012; Related U.S. Appl. No. 11/779,350.
Amendment filed Nov. 28, 2011, Related U.S. Appl. No. 11/779,350.
Final Office Action mailed Sep. 27, 2011; Related U.S. Appl. No. 11/779,350.
Amendment filed May 20, 2011, Related U.S. Appl. No. 11/779,350.
Non-Final Office Action mailed Feb. 16, 2011; Related U.S. Appl. No. 11/779,350.
Amendment filed Oct. 26, 2010; Related U.S. Appl. No. 11/779,350.
Non-Final Office Action mailed Jul. 26, 2010; Related U.S. Appl. No. 11/779,350.
Amendment filed May 4, 2010; Related U.S. Appl. No. 11/779,350.
Non-Final Office Action mailed Dec. 28, 2009; Related U.S. Appl. No. 11/779,350.
Notice of Allowance mailed Apr. 24, 2013; Related U.S. Appl. No. 11/779,380.
Notice of Appeal filed Mar. 14, 2012; Related U.S. Appl. No. 11/779,380.
Amendment filed Jan. 18, 2012; Related U.S. Appl. No. 11/779,380.
Final Office Action mailed Oct. 18, 2011; Related U.S. Appl. No. 11/779,380.
Amendment filed Jul. 18, 2011; Related U.S. Appl. No. 11/779,380.
Non-Final Office Action mailed Feb. 17, 2011; Related U.S. Appl. No. 11/779,380.
Amendment filed Nov. 29, 2010; Related U.S. Appl. No. 11/779,380.
Non-Final Office Action mailed Jul. 29, 2010; Related U.S. Appl. No. 11/779,380.
Amendment filed Jul. 12, 2010; Related U.S. Appl. No. 11/779,380.
Terminal Disclaimer filed Jul. 12, 2010; Related U.S. Appl. No. 11/779,380.
Non-Final Office Action mailed Mar. 19, 2010; Related U.S. Appl. No. 11/779,380.
Non-Final Office Action mailed Dec. 19, 2014; Related U.S. Appl. No. 13/943,680.
Non-Final Office Action mailed May 17, 2010; Related U.S. Appl. No. 11/842,109.
Non-Final Office Action mailed Aug. 18, 2009; Related U.S. Appl. No. 11/842,133.
Final Office Action mailed Mar. 8, 2010; Related U.S. Appl. No. 11/842,133.
Non-Final Office Action Mailed Jun. 10, 2009; Related U.S. Appl. No. 11/684,677.
Non-Final Office Action Mailed May 27, 2009; Related U.S. Appl. No. 11/684,681.
Non-Final Office Action Mailed Apr. 6, 2009; Related U.S. Appl. No. 11/558,101.
Non-Final Office Action Mailed Feb. 3, 2009; Related U.S. Appl. No. 11/557,851.
Non-Final Office Action Mailed May 29, 2000; Related U.S. Appl. No. 11/557,870.
Non-Final Office Action Mailed Jun. 10, 2009; Related U.S. Appl. No. 11/557,882.
Non-Final Office Action Mailed Jun. 19, 2009; Related U.S. Appl. No. 11/684,664.
Non-Final Office Action Mailed Jun. 22, 2009; Related U.S. Appl. No. 11/684,670.
Non-Final Office Action Mailed Jun. 23, 2009; Related U.S. Appl. No. 11/558,088.
Notice of Allowance Mailed Jul. 19, 2010; Related U.S. Appl. No. 11/559,235.
Notice of Allowance Mailed Apr. 16, 2010; Related U.S. Appl. No. 11/559,235.
Notice of Allowance Mailed Apr. 2, 2010; Related U.S. Appl. No. 11/559,235.
Amendment filed Dec. 4, 2009; Related U.S. Appl. No. 11/559,235.
Non-Final Office Action Mailed Sep. 15, 2009; Related U.S. Appl. No. 11/559,235.

* cited by examiner

SYSTEM AND METHOD FOR ESTIMATING ELECTRICAL CONDUCTION DELAYS FROM IMMITTANCE VALUES MEASURED USING AN IMPLANTABLE MEDICAL DEVICE

PRIORITY CLAIM

This application is a Divisional Application of and claims priority and other benefits from U.S. patent application Ser. No. 12/127,963, filed May 28, 2008, entitled "SYSTEM AND METHOD FOR ESTIMATING ELECTRICAL CONDUCTION DELAYS FROM IMMITTANCE VALUES MEASURED USING AN IMPLANTABLE MEDICAL DEVICE", now U.S. Pat. No. 8,208,999, incorporated herein by reference in its entirety.

RELATED APPLICATIONS

U.S. patent application Ser. No. 12/127,963 is a continuation-in-part, and this application claims priority to, U.S. patent application Ser. No. 11/779,350, of Wenzel et al., filed Jul. 18, 2007, entitled, "System and Method for Estimating Cardiac Pressurebased on Cardiac Electrical Conduction Delays using an Implantable Medical Device," now U.S. Pat. No. 8,504,152, which claimed priority to U.S. Provisional Patent Application No. 60/910,060 of Wenzel et al., entitled, "System and Method for Estimating Left Atrial Pressure based on Intra-Cardiac Conduction Time Delays," filed Apr. 4, 2007, which are both fully incorporated by reference herein.

FIELD OF THE INVENTION

The invention relates generally to implantable medical devices such as pacemakers and implantable cardioverter defibrillators (ICDs) and in particular to techniques for estimating conduction delays and cardiac pressure values (particularly left atrial pressure (LAP)) for use in detecting and evaluating heart failure and related conditions and to automatically adjust pacing parameters or the like.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation may deprive vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle mass causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. Often, electrical and mechanical dyssynchronies develop within the heart such that the various-chambers of the heart no longer beat in a synchronized manner, degrading overall cardiac function. A particularly severe form of heart failure is congestive heart failure (CHF) wherein the weak pumping of the heart or compromised filling leads to build-up of fluids in the lungs and other organs and tissues.

Many patients susceptible to CHF, particularly the elderly, have pacemakers, ICDs or other implantable medical devices implanted therein, or are candidates for such devices. Accordingly, it is desirable to provide techniques for detecting and tracking CHF using such devices. One particularly effective parameter for detecting and tracking CHF is cardiac pressure, particularly LAP, i.e. the blood pressure within the left atrium of the patient. Reliable detection or estimation of LAP would not only permit the implanted device to track CHF for diagnostic purposes but to also control therapies applied to address CHF such as cardiac resynchronization therapy (CRT). CRT seeks to normalize asynchronous cardiac electrical activation and the resultant asynchronous contractions by delivering synchronized pacing stimulus to the ventricles using pacemakers or ICDs equipped with biventricular pacing capability. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et at entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

Reliable estimates of LAP provided by a pacemaker or ICD would also allow the dosing of heart failure medications (such as diuretics) to be properly titrated so as to minimize the number of episodes of acute heart failure decompensation. Another advantage to providing reliable estimates of LAP is that physicians are typically familiar with LAP values. Hence, LAP estimates could be provided to the physician via diagnostic displays, which the physicians can then readily interpret.

However, LAP is a difficult parameter to detect since it is not clinically appealing to place a blood pressure sensor directly in the left atrium due to the chronic risk of thromboembolic events, as well as risks associated with the transseptal implant procedure itself. Accordingly, various techniques have been developed for estimating LAP based on other parameters that can be more safely sensed by a pacemaker or ICD. In this regard, a number of techniques have been developed that use electrical impedance signals to estimate LAP. For example, impedance signals can be sensed along a sensing vector passing through the left atrium, such as between an electrode mounted on a left ventricular (LV) lead and another electrode mounted on a right atrial (RA) lead. The sensed impedance is affected by the blood volume inside the left atrium, which is in turn reflected by the pressure in the left atrium. Accordingly, there is a correlation between the sensed impedance and LAP, which can be exploited to estimate LAP and thereby also track CHF. See, for example, U.S. Provisional Patent Application No. 60/787,884 of Wong et al., entitled, "Tissue Characterization Using Intracardiac Impedances with an Implantable Lead System," filed March 31, 2006, U.S. patent application Ser. No. 11/558,101, now abandoned, U.S. patent application Ser. No. 11/557,851, now abandoned, U.S. patent application Ser. Nos. 11/557,870, 11/557,882, now abandoned, and U.S. patent application Ser. No. 11/558,088, now U.S. Pat. No. 8,600,497, each entitled "Systems and Methods to Monitor and Treat Heart Failure Conditions", of Panescu et al. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device," now U.S. Pat. No. 8,712,519. Particularly effective techniques for calibrating impedance-based techniques are set forth in: U.S. patent application Ser. No. 11/559,235, by Panescu et al., entitled "System and Method for Estimating Cardiac Pressure Using Parameters Derived from Impedance Signals Detected by an Implantable Medical Device," now U.S. Pat. No. 7,794,404.

It is desirable to provide LAP estimation techniques that do not rely only impedance but alternatively exploit intracardiac electrogram (IEGM) signals commonly sensed by pacemakers and ICDs. Also, it is desirable to provide techniques for automatically adjusting and controlling CRT and other forms of cardiac rhythm management therapy in response to estimated LAP so as to, e.g., mitigate the effects of CHF.

The parent application, cited above, addressed these issues by providing techniques for estimating LAP or other cardiac performance parameters based on measured conduction delays. In particular, using the techniques set forth therein, LAP is estimated based on interventricular conduction delays.

Predetermined conversion factors stored within the device are used to convert the various conduction delays into LAP values or other appropriate cardiac performance parameters. The conversion factors may be, for example, slope and baseline values derived during an initial calibration procedure performed by an external system, such as an external programmer. In some examples, the slope and baseline values are periodically re-calibrated by the implantable device itself. Techniques were also set forth for adaptively adjusting pacing parameters based on estimated LAP or other cardiac performance parameters. For the sake of completeness, these various techniques are all fully described herein-below.

Thus, the parent application set forth techniques for estimating LAP based on measured conduction delays within the heart. U.S. patent application Ser. No 11/559,235, now U.S. Pat. No. 7,794,404, also cited above, set forth techniques for estimating LAP based on measured impedance values. Although these techniques are effective, it would also be desirable to combine the techniques to use impedance values (or admittance values) to estimate conduction delays and then use the conduction delays to estimate LAP. It is to this end that aspects of the present invention are directed. It is also desirable to provide techniques for estimating conduction delays from impedance values (or admittance values) and it is to this end that the present invention is primarily directed.

SUMMARY OF THE INVENTION

In accordance with an exemplary embodiment, a method and system are provided for estimating electrical conduction delays within the heart of a patient using an implantable medical device based on impedance or admittance values (referred to generally herein as immittance values) measured within the patient. Briefly, a value representative of electrical immittance is detected within the heart of the patient. An electrical conduction delay within the heart of the patient is estimated based the value representative of immittance. That is, the device exploits a correlation between impedance/admittance and electrical conduction delays to estimate the conduction delays. In this regard, as the heart tends to enlarge, particularly with heart failure progression, conduction delays tend to increase, whereas impedance values tend to decrease. Therefore, impedance (or admittance) values can be used to estimate conduction delays.

Preferably, cardiac pressure is then estimated within the patient based on the estimated electrical conduction delay. That is, the device then exploits a correlation between conduction delays and cardiac pressure to estimate LAP. Hence, impedance/admittance values are used to estimate conduction delays, which are in turn used to estimate LAP. In this manner, the device can exploit techniques that estimate LAP based on conduction delays, without needing to directly measure the conduction delays. This is particularly useful within devices that lack the capability to directly measure conduction delays. Moreover, the device need not rely on estimating LAP directly from impedance or admittance (as in some of the predecessor techniques discussed above). Within at least some patients, calibrating a direct impedance-to-LAP conversion procedure can be inconvenient and imprecise. By instead generating conduction delay estimates as intermediate values, the conduction delay values can be used to calibrate the conversion procedure, with reference to conduction delays obtained, e.g., using QuickOpt rapid optimization techniques or the like. QuickOpt techniques are described more fully in U.S. Patent Publication No. 2005/0125041 of Min et al., published Jun. 9, 2005, entitled "Methods for Ventricular Pacing," now abandoned. QuickOpt is a trademark of St. Jude Medical.

In one example, the immittance value to be detected is an impedance value (Z) obtained by measuring a raw impedance signal ($Z_0$) along at least one sensing vector passing through the heart of the patient and then determining the average impedance value (Z) from the raw impedance signal ($Z_0$) over, e.g., a period of sixteen seconds or about four respiratory cycles. Pre-determined conversion factors are then used for converting the average impedance values to conduction delay values within the patient. In an example where a single sensing vector is employed, the conduction delays are estimated by calculating:

$$\text{Delay} = \alpha + Z^2 + \beta * Z + \delta$$

where $\alpha$, $\beta$ and $\delta$ are the pre-determined conversion factors and wherein Z represents average impedance along a given vector passing through the heart of the patient. In an example where two sensing vectors are employed, the conduction delays are instead estimated by calculating.

$$\text{Delay} = \alpha_1 * Z_1^2 + \beta_1 * Z_1 + \alpha_2 * Z_2^2 + \beta_2 * Z_2 + \delta$$

where $\alpha_1$, $\beta_1$, $\alpha_2$, $\beta_2$ and $\delta$ are the conversion factors and wherein $Z_1$ represents the average impedance along a first vector passing through the heart of the patient and $Z_2$ represents the average impedance along a second, different vector passing through the heart of the patient. In some implementations, three or more sensing vectors are instead used.

In another example, the immittance value to be detected is an admittance value (Y) obtained by measuring a raw admittance signal ($Y_0$) and then determining the average admittance value (Y) from the raw admittance signal ($Y_0$) over, e.g., a period of sixteen seconds. Pre-determined conversion factors are then used for converting the average admittance values to conduction delay values within the patient. In an example where a single sensing vector is employed, the conduction delays are estimated by calculating:

$$\text{Delay} = \alpha * Y^2 + \beta * Y + \delta$$

where α, β and δ are the pre-determined conversion factors and wherein Y represents admittance along a given vector passing through the heart of the patient. The conversion factors will typically be different from the ones used with impedance. In an example where two sensing vectors are employed, the conduction delays are instead estimated by calculating.

$$\text{Delay} = \alpha_1 * Y_1^2 + \beta_1 * Y_1 + \alpha_2 * Y_2^2 + \beta_2 * Y_2 + \delta$$

where $\alpha_1$, $\beta_1$, $\alpha_2$, $\beta_2$ and $\delta$ are the conversion factors and wherein $Y_1$ represents the average admittance along a first vector passing through the heart of the patient and $Y_2$ represents the average admittance along a second, different vector passing through the heart of the patient. Again, the conversion factors will typically be different from the ones use with impedance. In some implementations, three or more sensing vectors are instead used.

The various conversion factors can be obtained in advance by, e.g., measuring conduction delays using an external system equipped with QuickOpt while also measuring average impedance or admittance using the implanted device. Linear regression techniques are then exploited to calculate the appropriate conversion factors for converting impedance/admittance values to conduction delays.

Once the conduction delays have been estimated, LAP or other cardiac pressure values are then estimated from the delays. In one example, predetermined conversion factors are again used. The conversion factors may be, for example, slope and baseline values derived using linear regression techniques. Then, LAP or other cardiac pressure values are estimated within the patient by applying the conversion factors to the estimated conduction delay. For example, cardiac pressure may estimated using:

$$\text{Cardiac Pressure} = \text{Delay} * \text{Slope} + \text{Baseline}$$

where Delay is the estimated conduction delay and Slope and Baseline are the conversion factors appropriate to the pressure value being estimated.

Note that the pressure value estimated in the foregoing example (and in the other examples described herein) is an effective intracardiac pressure ($P_{\text{eff}}$), not an absolute pressure. It represents the absolute intracardiac pressure less intrathoracic pressure:

$$P_{\text{eff}} = P_{\text{intracardiac}} - P_{\text{intrathoracic}}$$

That is, the effective pressure is a type of gauge pressure. Unless otherwise noted, all estimated cardiac pressure values discussed herein, particularly estimated LAP, are effective pressure values. In some techniques described herein, such as techniques where the Valsalva maneuver is exploited to reduce intracardiac pressure within the patient for calibration purposes, the distinction between effective pressure and absolute pressure is particularly important and effective pressure should be used. In any case, effective pressure values are typically more useful from a clinical perspective than absolute pressure values.

In some implementations, therapy is then controlled based on the estimated LAP value, particularly so as to reduce LAP, or based on the estimated conduction delays. For example, pacing timing parameters such as the atrioventricular (AV) pacing delay and the interventricular (LV-RV) pacing delay may be adjusted. Within systems equipped to provide pacing at different locations within the same chamber, intraventricular ($LV_1$-$LV_2$), intra-atrial ($LA_1$-$LA_2$) delay values may additionally or alternatively be adjusted. Alternatively, multi-site pacing systems can switch to different pacing configurations or use different pacing electrodes in order to keep the LAP estimate within a safe or hemodynamically stable range. Preferably, the adjustments are adaptive, i.e. the adjustments are performed in a closed-loop so as to adapt the adjustments to changes in estimated LAP or changes in conduction delays so as to optimize therapy.

By adjusting pacing parameters, the parameters can be promptly adjusted to immediately respond to changes within the heart that affect conduction delays or LAP, such as any deterioration in mechanical synchrony arising due to CHF, conduction defects or other ailments such as myocardial infarction or acute cardiac ischemia. Moreover, by adaptively adjusting the pacing parameters, the direction and/or magnitude of the adjustments need not be pre-determined. For example, it need not be known in advance whether a particular pacing parameter should be increased or decreased in response to deterioration in LAP. Adaptive adjustment allows the direction and magnitude of any adjustments to the pacing parameters to be automatically optimized. Thus, if an initial increase in a particular pacing parameter causes a further deterioration in LAP, the pacing parameter may then be automatically decreased in an attempt to improve LAP. If neither an increase nor a decrease in a particular pacing parameter significantly affects LAP, then a different pacing parameter may be selected for adaptive adjustment.

The adaptive adjustment of pacing therapy using estimated conduction delays or estimated LAP may be performed in conjunction with one or more impedance-based adjustments techniques, such as those set forth in the above-cited applications of Panescu et al. For example, a value representative of mechanical dyssynchrony may be derived from average impedance while an estimate of LAP is derived from conduction delays, permitting both to be used in adjusting the pacing parameters. Also, impedance signals may be used to derive electrical conduction delays from which LAP may be also estimated. Still further, if the implanted device is equipped with a sensor to directly measure another cardiac pressure value besides LAP (e.g., LV end diastolic ($LV_{END}$) pressure), then such pressure measurements may be used in conjunction with the LAP estimates to adjust pacing parameters so as to reduce both measures of pressure.

In some implementations, the pacing parameters are adaptively adjusted only when the patient is in certain predetermined states as determined by activity sensor, posture detectors, etc. In one particular example, adaptive adjustment is only performed if the patient is at rest and in a supine posture. Adaptive adjustment may be still further limited to times when the blood oxygen saturation ($SO_2$) level of the patient is within a certain acceptable range. Also, since conduction delays are being estimated (along with LAP), pacing therapy can be adjusted to control the estimated delays so as to maintain the delays within a safe or stable range about a baseline. That is, both the final LAP estimate and the intermediate conduction delay estimate can be used to control pacing therapy, track CHF, etc.

Thus, various techniques are provided for estimating conduction delays and/or LAP for use, e.g., in automatically adjusting pacing therapy and for detecting and tracking heart failure. Individual implantable systems may be equipped to perform some or all of these techniques. In some examples, LAP is determined by combining estimates derived from the various individual techniques. Heart failure is then detected or tracked based on the combined LAP estimate. Upon detecting of the onset of heart failure, appropriate warning signals may be generated for alerting the patient to consult a physician. The warning signals can include "tickle" warning signals applied to subcutaneous tissue and short-range telemetry warning signals transmitted to a warning device external to the patient such as a bedside monitor. The warning signals, as well as appropriate diagnostic information (such as the estimated LAP values), are preferably forwarded to the physician by the bedside monitor.

Various other forms of therapy may also be automatically applied or modified by the implanted system in response to heart failure, depending upon the capabilities of the system. For example, if the device is equipped to perform CRT, then CRT pacing may be initiated or otherwise controlled based on LAP. Also, if the implanted system is equipped with a drug pump, appropriate medications (such as diuretics) potentially may be administered directly to the patient, depending upon the programming of the system. Alternatively, the estimated LAP may be presented directly to the patient using a handheld or a bedside monitor, so that the patients may utilize the estimated LAP reading to self-titrate oral dosages of heart failure medications based on a sliding scale prescription that was provided to the patient in advance. This is similar to the self-titration of insulin dosage based on a measured blood sugar from a glucometer using a prescribed insulin sliding scale.

Although summarized with respect to examples where LAP is estimated based on conduction delays derived from immittance values, the techniques of the invention may also be applied to estimating other parameters from measured immittance values. For example, LV end diastolic volume (EDV) or LV end diastolic pressure (EDP) may also be estimated, at least within some patients, based on conduction delays by using appropriate calibration factors. Thus, a variety of cardiac chamber parameters may be estimated based on measured impedance/admittance values. LAP is generally preferred as it is strongly correlated with CHF.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
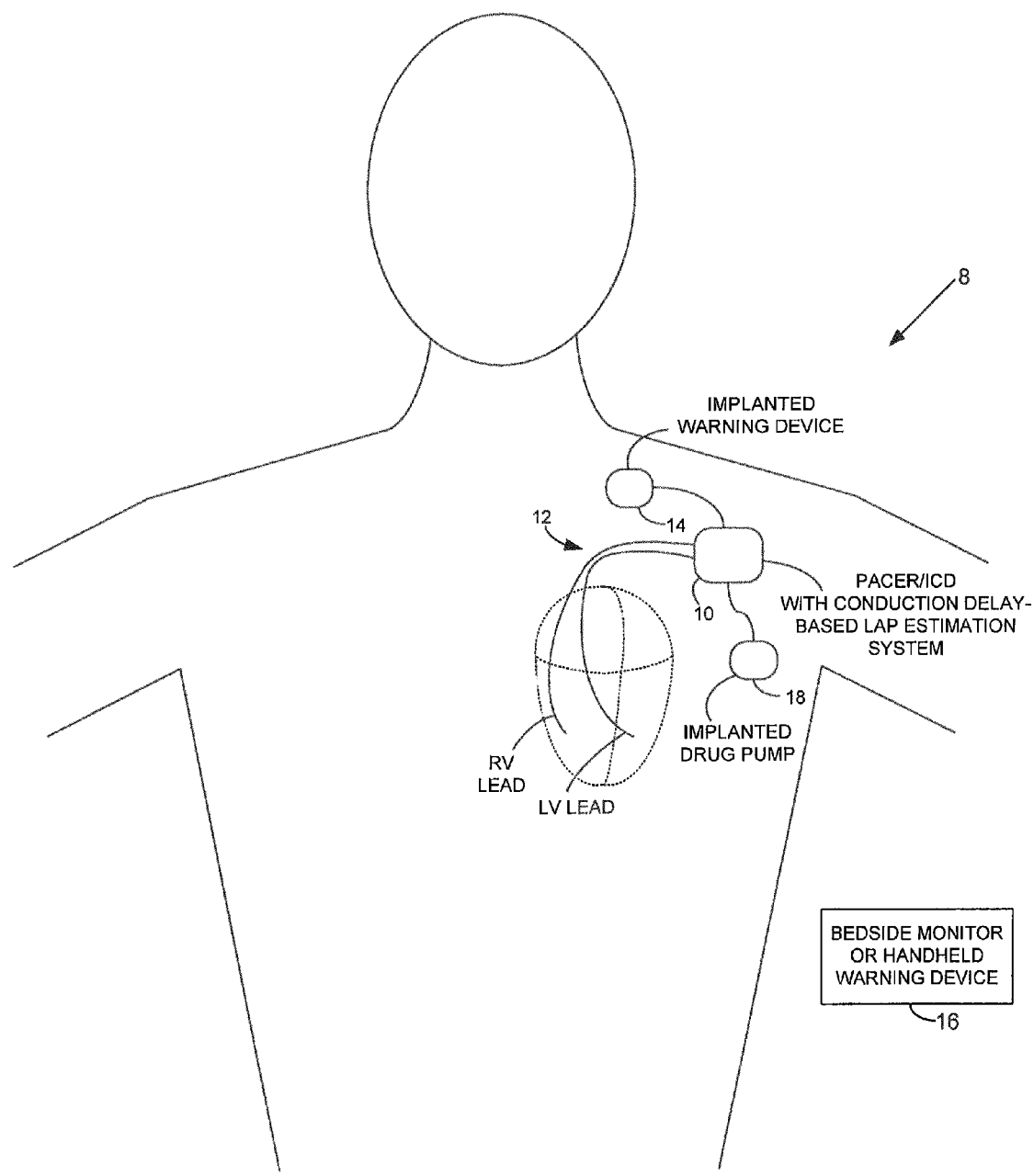
FIG. 1 is a stylized representation of an exemplary implantable medical system equipped with a conduction delay-based LAP estimation system.
Figure 14:
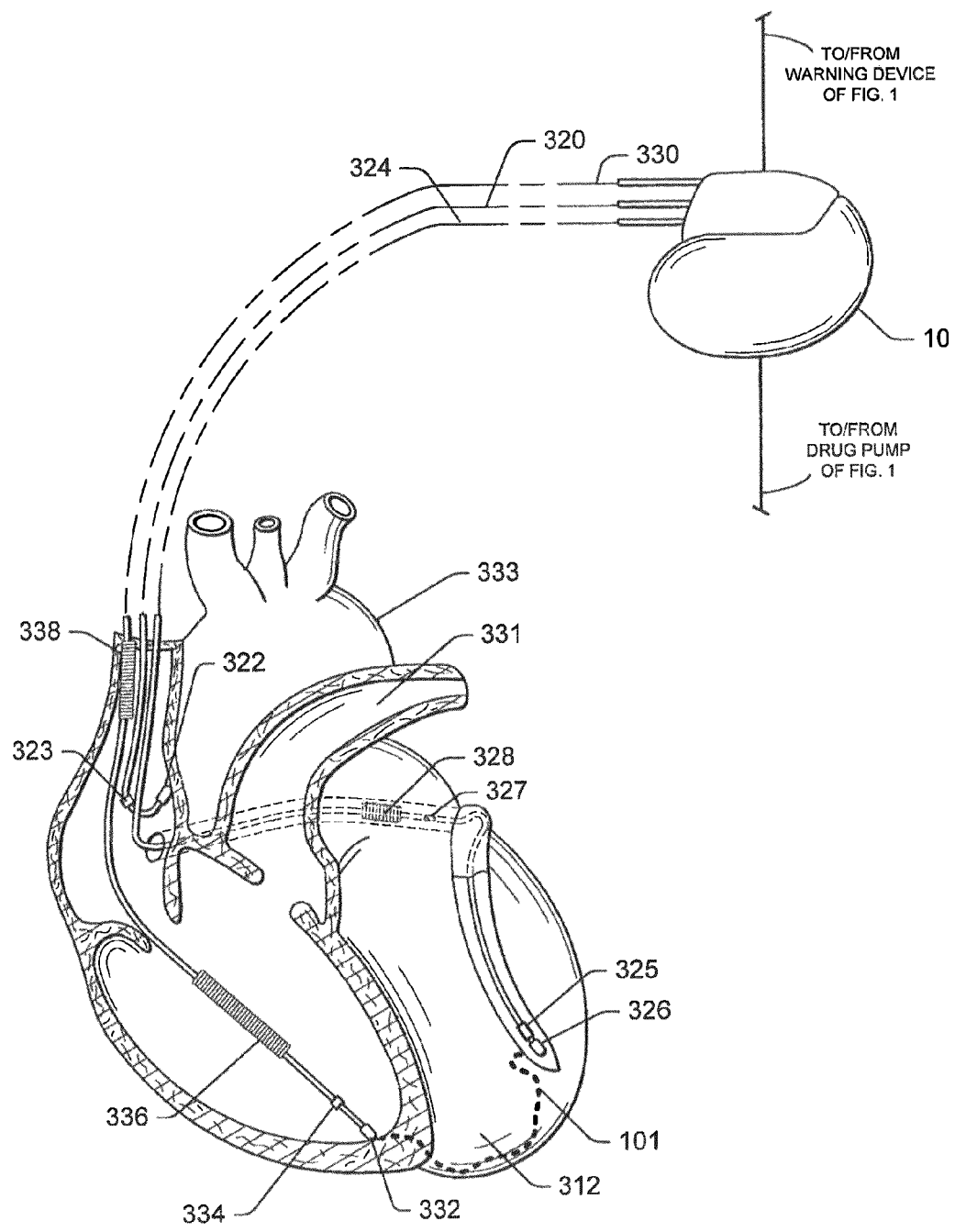
FIG. 14 is a simplified, partly cutaway view, illustrating the pacer/ICD of FIG. 1 along with a more complete set of leads implanted in the heart of the patient.

FIG. 1 provides a stylized representation of an exemplary implantable pacing medical system 8 capable of detecting electrical conduction delays within the heart of the patient and estimating LAP based on the conduction delays. To this end, implantable system 8 includes a pacer/ICD 10 or other cardiac stimulation device that incorporates internal components (shown individually in FIG. 15, and discussed below) for detecting one or more conduction delays using electrodes mounted to a set of sensing/pacing leads 12 and for estimating LAP or other cardiac performance parameters based on the conduction delays. In FIG. 1, only two leads are shown. A more complete set of leads is illustrated in FIG. 14, which is discussed below. Within many of the exemplary implementations described herein, LAP is estimated based on LV-RV delays detected by the pacer/ICD. However, other conduction delays can be exploited, alone or in combination, to estimate other cardiac pressure values or other cardiac performance parameters, such as EDV. LAP is emphasized as it is correlated with CHF. Predetermined conversion factors stored within the pacer/ICD are used to convert the conduction delays into LAP values or other appropriate cardiac chamber parameters. The conversion factors may be, for example, slope and baseline values derived during an initial calibration procedure performed by an external system, such as an external programmer (FIG. 16.) As will be explained, the baseline value may be periodically re-calibrated by the pacer/ICD itself. The slope value is assumed to remain substantially unchanged such that re-calibration of the slope is typically not required.

Figure 2:
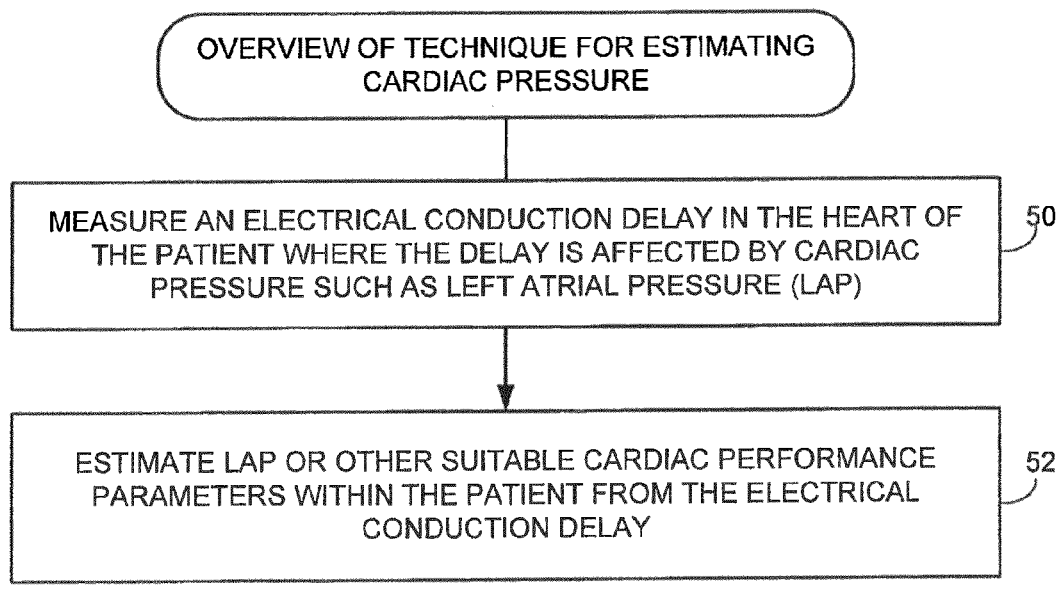
FIG. 2 is a flow diagram providing a broad overview of conduction delay-based cardiac pressure estimation techniques that may be performed by the system of FIG. 1.

FIG. 2 provides a broad summary of the cardiac pressure estimation techniques that may be performed by the pacer/ICD of FIG. 1. At step 50, the pacer/ICD measures an electrical conduction delay in the heart of the patient where the delay is affected by cardiac pressure such as left atrial pressure (LAP). At step 52, the pacer/ICD then estimates LAP or other suitable cardiac chamber values within the patient from the electrical conduction delay. The pacer/ICD of FIG. 1 is also equipped to track changes in the estimated LAP values so as to detect and track CHF and to adjust pacing parameters in an effort to mitigate CHF, such as CRT parameters. Techniques for performing CRT are discussed in the patents to Mathis, et al., Kramer, et al., to Stahmann, et al., cited above. Adaptively adjustment techniques set forth in the Panescu et al. patent application, "Closed-Loop Adaptive Adjustment of Pacing Therapy based on Cardiogenic Impedance Signals Detected by an Implantable Medical Device," cited above, may be exploited. Additionally or alternatively, the pacer/ICD may issue warning signals, if warranted. For example, if the estimated LAP exceeds a threshold indicative of CHF, warning signals may be generated to warn the patient, using either an implanted warning device 14 or an external bedside monitor/handheld warning device 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external warning device above his or her chest. The handheld device receives short-range telemetry signals from the implanted device and provides audible or visual verification of the warning signal. The handheld warning device thereby provides confirmation of the warning to the patient along with a display of the estimated LAP, who may be otherwise uncertain as to the reason for the internally generated warning signal. For further information regarding this warning/notification technique, see U.S. patent application Ser. No. 11/043,612, of Kil et al., filed Jan. 25, 2005, entitled "System and Method for Distinguishing among Cardiac lschemia, Hypoglycemia and Hyperglycemia using an Implantable Medical Device," now U.S. Pat. No. 7,502,644.

If a bedside monitor is provided, the bedside monitor provides audible or visual alarm signals to alert the patient or caregiver, as well as textual or graphic displays. In addition, diagnostic information pertaining to the deteriorating cardiac condition is transferred to the bedside monitor or is stored within the pacer/ICD for subsequent transmission to an external programmer (not shown in FIG. 1) for review by a physician or other medical professional. The physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of any significant increase in LAP. Networking techniques for use with implantable medical systems are set forth, for example, in U.S. Pat. No. 6,249,705 to Snell, entitled "Distributed Network System for Use with Implantable Medical Devices."

In addition to CRT, other forms of therapy may also be controlled by the pacer/ICD in response to changes in LAP. In this regard, if the implanted system is equipped with a drug pump, appropriate medications may be automatically administered upon detection of a significant increase in LAP due to heart failure. For example, heart failure medications may be delivered directly to the patient via the drug pump, when needed. Alternatively, if a drug pump is not available, the patient may be provided with instructions depending on the estimated LAP as to what dosage to take for various heart failure medications. Exemplary heart failure medications include angiotensin-converting enzyme (ACE) inhibitors, diuretics, nitrates, digitalis and compounds such as captopril, enalapril, lisinopril and quinapril. For example, upon detection of a high LAP level, the dosage of diuretics could be increased, either automatically via a drug pump or by sending appropriate instructions to the bedside monitor for alerting the patient or caregiver. Depending upon the particular medication, alternative compounds may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure as determined from LAP.

Various techniques may be employed to confirm the detection of heart failure (or other medical conditions) made by the pacer/ICD based on the analysis of the conduction delay before drug therapy is delivered. Exemplary impedance-based heart failure detection/evaluation techniques are set forth in U.S. patent application Ser. No. 11/559,235, now U.S. Pat. No. 7,794,404, cited above. See, also U.S. Pat. No. 6,748,261, entitled "Implantable medical device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No.6,643,548, entitled "Implantable medical device for Monitoring Heart Sounds to Detect Progression and Regression of Heart Disease and Method Thereof"; U.S. Pat. No 6,572,557, entitled "System and Method for Monitoring Progression of Cardiac Disease State using Physiologic Sensors"; and U.S. Pat. No 6,480,733, entitled "Method for Monitoring Heart Failure", each assigned to Pacesetter, Inc.

Hence, FIGS. 1 and 2 provide an overview of an implantable medical system capable of estimating LAP based on conduction delays, adjusting pacing parameters, delivering any appropriate warning/notification signals, and selectively delivering medications, when warranted. Embodiments may be implemented that do not necessarily perform all of these functions. For example, embodiments may be implemented that estimate LAP but do not automatically initiate or adjust therapy. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations and sizes of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of Conduction Delay-Based Estimation Techniques

Figure 3:
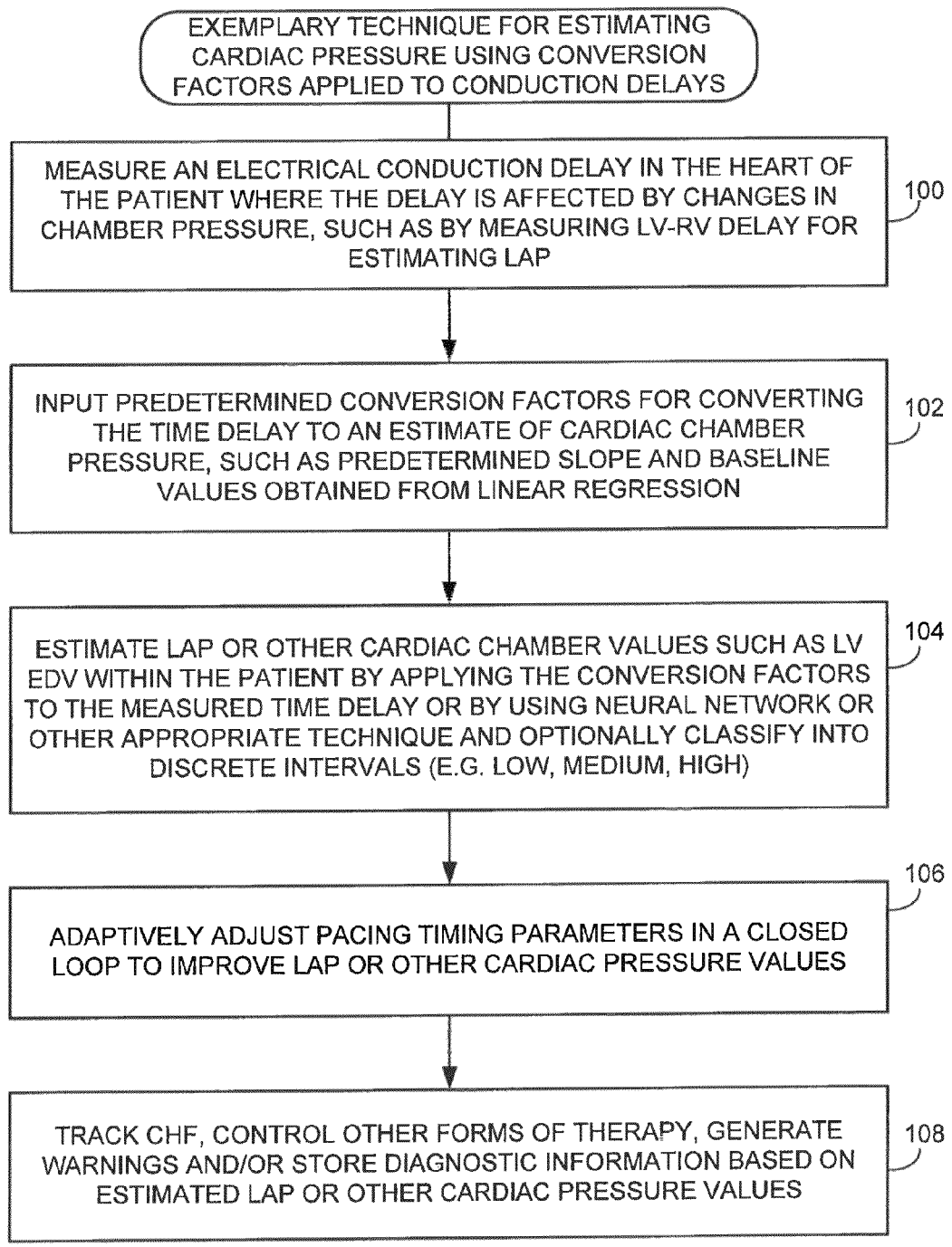
FIG. 3 is a flow diagram summarizing an illustrative technique performed in accordance with the general technique of FIG. 2 wherein cardiac pressure is estimated from conduction delays using pre-determined conversion factors and wherein pacing timing parameters are then adaptively adjusted based on the estimated pressure values.

FIG. 3 provides an overview of LAP estimation techniques that may be performed by the pacer/ICD of FIG. 1 or other implantable medical device. At step 100, the pacer/ICD measures an electrical conduction delay in the heart of the patient where the delay is affected by changes in chamber pressure, such as by measuring an interventricular LV-RV delay for use in estimating LAP. An exemplary interventricular conduction path 101 along which the delay may be measured is shown in FIG. 14, which is described more fully below. The conduction path extends through myocardial tissue between, in this particular example, a pair of LV tip and ring electrodes 426 and 425 of a coronary sinus (CS) lead 424 and a paired of RV tip and ring electrodes 424 and 434 of an RV lead 430. The tip and ring electrodes 422, 423 of a RA lead 420 are also shown. The exemplary interventricular conduction path 101 extends, as shown, down from the LV electrodes toward the apex of the ventricles and then in to the RV. Once the myocardium of the LV begins to depolarize in the vicinity of the LV electrodes, electrical depolarization signals propagate along the path ultimately triggering myocardial depolarization within the RV, which is sensed using the RV electrodes. The time during which the depolarization signal propagates along this (or other) interventricular paths is the conduction time delay measured at step 100 of FIG. 3. It should be understood that the LV-RV delay may be negative, i.e. the RV may depolarize first, followed by the LV (with the RV depolarizing either naturally or due to a V-pulse delivered to the RV.) That is, depolarization signals may propagate along an interventricular conduction path from the RV to LV, instead of vice versa. Herein, for clarity, when the LV-RV delay is negative, the delay is instead typically referred to as an RV-LV delay.

The inter-ventricular conduction time delay following the delivery of a left ventricular pacing stimulus may be used to estimate LV size and/or LV filling pressure. At the time a pacing stimulus is delivered to the LV, the chamber is filled with blood and corresponds to the LV EDV. The pacing stimulus will cause the LV muscle to depolarize and subsequently contract. While the LV depolarization occurs, the depolarization wavefront travels across the LV toward the right ventricle and ultimately causes the RV to depolarize and subsequently contract. The delay between the time when the LV pacing stimulus was administered and the time when the RV depolarizes may be proportional to the LV EDV, which is also proportional to the LV EDP. LV EDP is a good estimate for LAP in the absence of significant mitral valve stenosis. Thus, the interventricular time delay in cardiac depolarization and/or contraction following a ventricular stimulus may be used, at least within some patients, to estimate the end-diastolic ventricular filling volume and/or filling pressure.

Moreover, the duration of the interventricular conduction delay depends largely upon the distance over which the depolarization signal traverses, which depends, in part, on the sizes of the chambers of the heart it passes through. As heart failure progress, pressure within the LV increases and the LV chamber often becomes distended, resulting in a generally longer conduction time delay. Hence, there is, in at least some patients, a correlation between interventricular conduction time delays and LV chamber size and LV chamber pressure. Hence, in such patients, there is a correlation between LV-RV delay and LV EDV and LV EDP. Likewise, as heart failure progresses, LAP increases. Accordingly, within at least some patients, there is also a correlation between LV-RV delay and LAP. The techniques of the invention exploit this correlation to estimate LAP from the LV-RV delay. LV EDV and LV EDP may also be estimated from the LV-RV delay.

Figure 4:
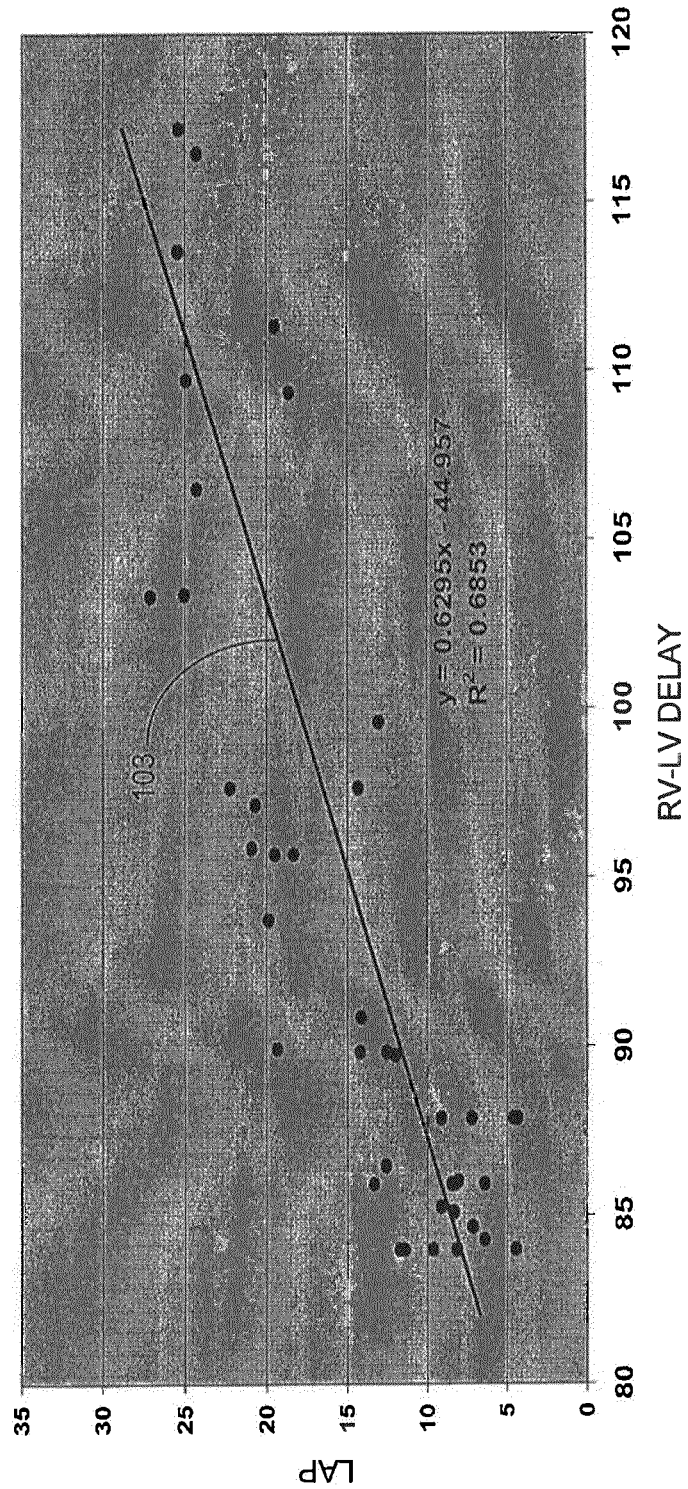
FIG. 4 is a graph illustrating a linear correlation between LAP and LV-RV delay that may be exploited by the estimation procedure of FIG. 3.

FIG. 4 illustrates data collected from a canine test subject showing the correlation between RV-LV delay (in msecs) and LAP (in mmHg). In this example, the RV-LV delay was measured based on paced RV pulses using the QuickOpt techniques, discussed below. LAP was measured using a HeartPOD LAP detection device developed by Savacor Inc., now owned by St. Jude Medical. HeartPOD is a trademark of St. Jude Medical. The canine test subject was paced via a rapid pacing protocol so as to induce and emulate heart failure, which resulted in increasing LAP values over time. As can be seen, there is a linear correlation between LAP and RV-LV delay within this test subject, as represented by linear regression line 103. Similar correlations are present in at least some, and likely most, human heart failure patients. Based on the correlation, LAP can be estimated based on RV-LV conduction delays (or LV-RV delays), at least within patients where the correlation is present.

An LV-RV conduction delay may be measured, for example, by tracking the time between when a V-pulse is delivered to the LV using the LV tip and ring electrodes and the peak of a QRS-complex sensed within the RV using the RV tip and ring electrodes. An RV-LV conduction delay may be measured, for example, by tracking the time between when a V-pulse is delivered to the RV using the RV tip and ring electrodes and the peak of a QRS-complex sensed within the LV using the LV tip and ring electrodes. However, other points within the QRS-complexes might instead be employed, such as the starting point of a complex. The peak is typically the easiest to detect. Also, instead of using the time at which a V-pulse is delivered, the pacer/ICD might instead detect and use the peak of the resulting evoked response (RV). Hence, conduction delays derived from paced events may be quantified in a variety of ways. As will be explained, conversion factors are used to convert the measured time delay into LAP or other cardiac performance values. So long as the system uses the appropriate conversion factors, the conduction delays may be measured using any suitable technique. Also, the pacer/ICD is not limited to measuring conduction delays from paced events. As another example, the conduction delay might instead be measured between the peak of a QRS-complex sensed in the LV using the tip and ring electrodes of the CS lead and the peak of the QRS-complex sensed within the RV, again using tip and ring electrodes of a RV lead. Again, the conduction delay may be quantified in a variety of ways, so long as the appropriate conversion factors are employed.

At step 102, the pacer/ICD inputs predetermined conversion factors for converting the measured time delay to an estimate of cardiac chamber pressure, such as predetermined slope and baseline values obtained from linear regression analysis applied to data of the type shown in FIG. 4 (though, of course, collected from human patients). Exemplary calibration techniques for determining the conversion factors based on a linear equation derived from linear regression are discussed below. At step 104, the pacer/ICD then estimates LAP or other cardiac pressure values within the patient by applying the conversion factors retrieved from memory to the measured time delays or by using a neural network, linear discriminant analyzer (LDA) or other appropriate technique. Also, the pacer/ICD may classify the pressure value within discrete intervals, such as LOW, MEDIUM and HIGH. That is, the pacer/ICD need not calculate specific values of the cardiac pressure but may instead simply determine whether the pressure is low, medium or higher, or within other predetermined ranges. The discrete intervals may be used as part of a prediction model that predicts LAP trends in a discrete fashion.

When using slope and baseline conversion factors to estimate specific values of pressure, cardiac pressure may be generally estimated using:

$$\text{Cardiac Pressure} = \text{Delay} * \text{Slope} + \text{Baseline}$$

where Delay represents the measured conduction delay, i.e. LV-RV delay, etc., and Slope and Baseline represent the conversion factors appropriate for use with the particular delay. This formula assumes a linear relationship between cardiac pressure and the measured conduction delay, which is an appropriate presumption based on the particular conduction delays discussed herein, at least insofar as estimating LAP is concerned. Routine experimentation may be performed to determine whether a linear relationship is also suitable for use in estimating other particular cardiac chamber values, such as LVP, LV EDV or LV EDP, or is also suitable for use with other conduction delays, such as RA-LV, RA-RV, RA-LA, etc. Moreover, it should be understood that linear models need not necessarily be used, i.e. more sophisticated correlation models may instead by employed. Linear models are preferred in view of their simplicity. As noted, neural networks or LDAs may instead be employed, where appropriate.

At step 106, the pacer/ICD then adaptively adjusts pacing timing parameters in a closed loop to improve LAP or other cardiac performance values. For example, LV-RV delays or AV delays may be adjusted in an effort to reduce LAP. That is, a combination of AV delay and LV-RV delay values are selected that yield the lowest LAP values. However, other delay parameters may be adjusted as well, such as inter-atrial delays or, if the implantable system is equipped to pace at two or more locations within a given atrial or ventricular chamber, then intra-atrial or intraventricular delays may be adjusted. Adaptive adjustment techniques are discussed in greater detail below. At step 108, the pacer/ICD tracks CHF, controls pacing therapy (such as CRT), generates warnings and/or stores diagnostic information based on estimated LAP values or other estimated cardiac chamber parameters. As already explained, the warnings and/or diagnostic data can be forwarded to a physician for review. Preferably, the diagnostic data includes the estimated LAP values for physician review. This is particularly advantageous since physicians are typically more comfortable reviewing LAP information than raw conduction delay values.

Preferably, steps 100-108 are repeated for each heartbeat to track changes in LAP on a beat-by-beat basis, adjust pacing parameters, track CHF, etc. That is, in some implementations, a near real-time LAP(t) function may be estimated so as to allow the pacer/ICD to track beat-to-beat changes in LAP. This allows the pacer/ICD to respond promptly to changes within the heart of the patient. Also, the beat-by-beat LAP estimates may be applied to a predictor or prediction model so as to predict changes in LAP so that therapy may be controlled in advance of unacceptably high LAP levels or so that warnings may be generated in advance.

If the LV and RV are both being paced so that interventricular conduction delays are not readily measurable via IEGMS, the pacer/ICD may be programmed to periodically suspend RV pacing (or LV pacing) so as to permit at least a few intrinsic ventricular depolarizations so that the conduction delays can be measured. Alternatively, the electrical conduction delay technique of the invention may be used in conjunction with impedance-based mechanical delay techniques, which can derive estimates of LAP during those heartbeats when LV-RV conduction delays are not readily measurable. See, for example, U.S. patent application Ser. No. 11/558,194, by Panescu et al., now U.S. Pat. No. 8,712,519, cited above. In general, the conduction delay-based LAP estimation techniques of the invention can be combined with a variety of other LAP estimation techniques to derive a final estimate of LAP. Still further impedance signals may be analyzed to determine the electrical conduction delays from which cardiac pressure may then be estimated using appropriate conversion factors. In this regard, it is known in the art that electrical impedance changes may be indicative of changes in heart chamber dimensions. See, e.g., U.S. Pat. No. 5,003,976 to Alt. Alt describes that analyzing the impedance between two intracardiac electrodes may be used to determine changes in cardiac chamber volumes. As already explained, changes in chamber volume also affect conduction delays, allowing impedance signals to be used to detect conduction delays, particularly in circumstance where such delays cannot readily be determined from IEGMs.

Although the examples described herein are primarily directed to estimating LAP, other cardiac performance parameters may alternatively be estimated, such as LV EDV, LV EDP, RVP, RAP, etc., by using appropriate conversion factors in combination with appropriate conduction delays. Otherwise routine experimentation may be performed to identify particular parameters detectable using the techniques of the invention and the appropriate conduction delays and conversion factors. In some cases, a linear conversion may not be suitable and algorithms that are more sophisticated may be required to convert conduction delays into parameter estimates. In some cases, multiple conduction delays may be required to properly estimate a particular parameter. That is, multiple conduction delays may be measured using different electrodes so as to permit the pacer/ICD to estimate chamber pressures and volumes within different chambers of the heart, assuming appropriate conversion values have been determined and calibrated. To this end, the implanted system may be equipped, e.g., with multiple electrodes per lead or with multiple leads per chamber. Unipolar, bipolar or cross-chamber sensing systems may be employed, where appropriate.

Turning now to FIGS. 5-13, various illustrative embodiments will be described in greater detail.

Exemplary LAP Estimation Techniques

Figure 5:
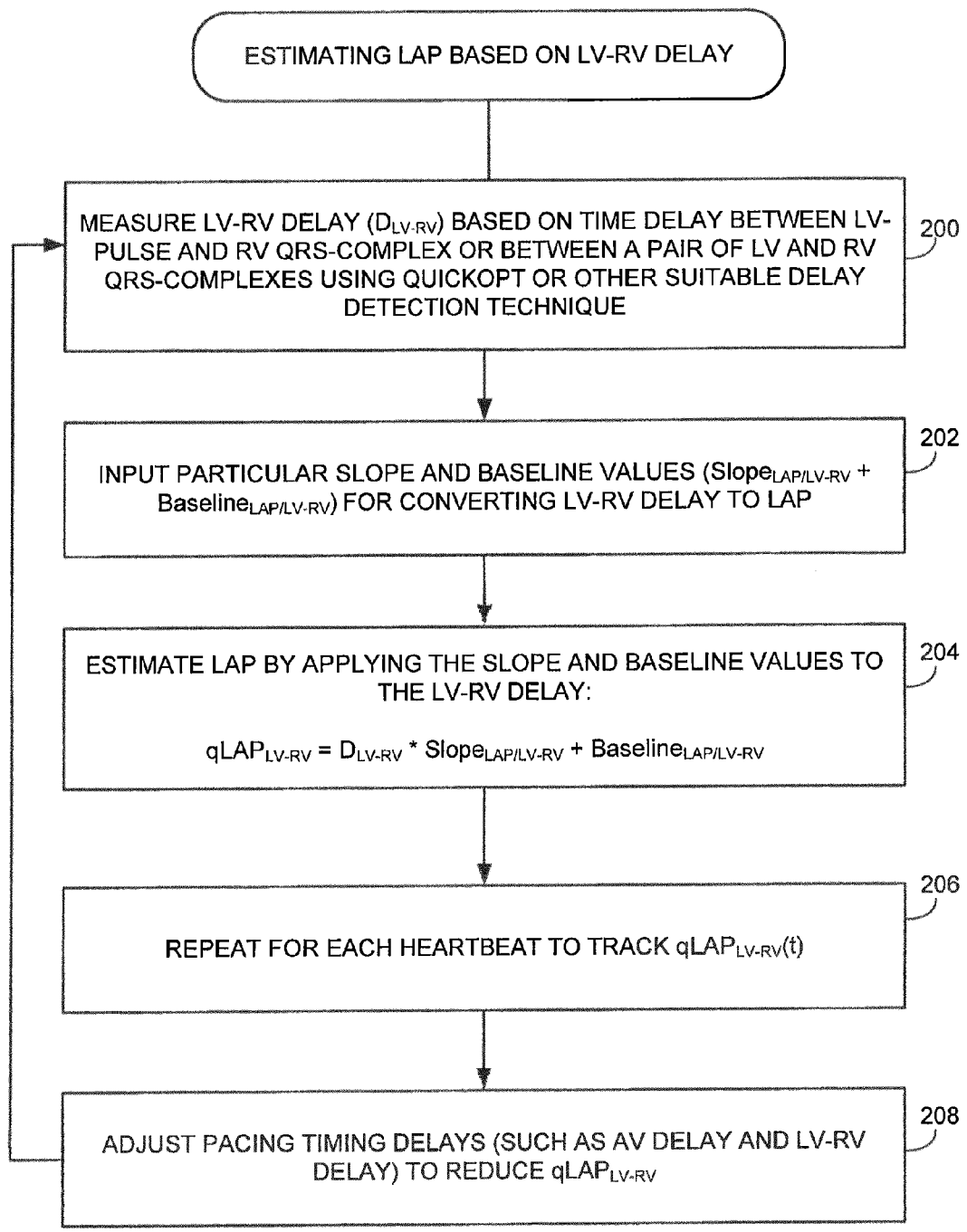
FIG. 5 is a flow diagram illustrating a particular example of the illustrative technique of FIG. 3 wherein LAP is estimated based on measured LV-RV delays, along with appropriate slope and baseline calibration values, to produce a qLAP value.

FIG. 5 provides an LV-RV delay-based LAP detection example wherein QuickOpt procedures were used for ascertaining the conduction delays. At step 200, the pacer/ICD measures the LV-RV delay ($D_{LV-RV}$) based on time delay between an LV-pulse and an RVQRS-complex or between a pair of LV and RVQRS-complexes using QuickOpt or other suitable delay detection technique. The QuickOpt technique is discussed in U.S. Patent Application No. 2005/0125041, cited above. For the sake of completeness, pertinent portions of the QuickOpt code are provided in the attached appendix (Appendix A). The example of Appendix A primarily operates to set RV thresholds. However, the LV-RV delay may be obtained using information generated by the code. That is, in the code, "ndx_lv" is the location of the LV QRS. "ndx_rv" is the location of the RV QRS. Hence, the LV-RV delay may be obtained by subtracting ndx_rv from ndx_lv (or vice versa).

At step 202, the pacer/ICD inputs the particular slope and baseline values ($Slope_{LAR/LV-RV}$ and $Baseline_{LAP/LV-RV}$) for converting the delay value ($D_{LV-RV}$) into an estimate of LAP (denoted $qLAP_{LV-RV}$). The slope and baseline values (which also may be referred to as gain and offset values) are predetermined conversion values that the pacer/ICD retrieves from memory. Calibration techniques for initially deriving the conversion values will be discussed below with reference to FIGS. 8-13. At step 204, the pacer/ICD estimates LAP by applying the slope and baseline values to the delay value:

$$qLAP_{LV-RV} = D_{LV-RV} * Slope_{LAP/Lv-RV} + Baseline_{LAP/LV-RV}$$

As indicated by step 206, the pacer/ICD repeats for each heartbeat to track qLAP(t). The LV-RV subscript is applied to qLAP to indicate that this estimate is made based on LV-RV delays (rather than some other conduction delay value.) The LAP/LV-RV subscript is applied to Slope and Baseline to indicate that these conversion factors are appropriate for use in estimating LAP based on LV-RV delays (rather than some other cardiac chamber parameter estimated from some other conduction delay value.)

Figure 6:
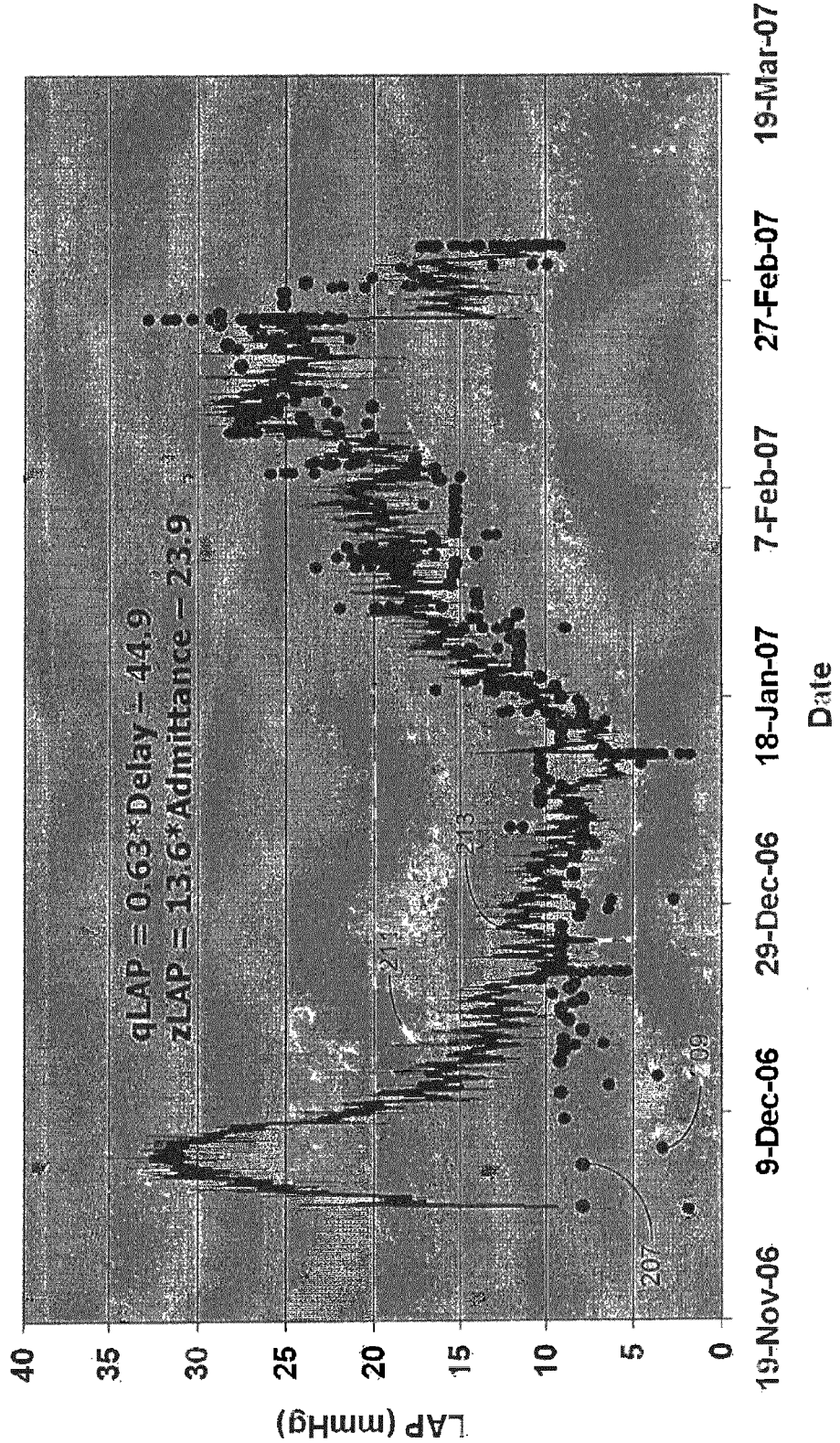
FIG. 6 is a graph providing exemplary data illustrating changes over time in qLAP values estimated within a canine test subject using the technique of FIG. 5.

FIG. 6 illustrates $qLAP_{LV-RV}$ values obtained within the same canine test subject of FIG. 4 showing changes over time as heart failure is induced. Light-shaded dots 207 are $qLAP_{LV-RV}$ values calculated as described herein. The darker-shaded dots 209 are actual LAP values measured using the HeartPOD system, discussed above, which includes an LAP sensor. As can be seen, the $qLAP_{LV-RV}$ values correlate fairly well with the HeartPOD values, verifying that the estimation is effective. (The $qLAP_{LV-RV}$ values are not necessarily identical to the actual LAP values since $qLAP_{LV-RV}$ merely provides an estimate of LAP and not a precise value.) The graph also shows zLAP values (represented by way of the light-shaded curve 211), as well as a six point moving average of zLAP (represented by way of the dark-shaded curve 213). The zLAP values were obtained using the impedance-based LAP estimation detection techniques set forth in U.S. patent application Ser. No. 11/559,235, cited above, now U.S. Pat. No. 7,794,404. (More generally, the techniques described therein are "admittance-based.") As can be seen, the zLAP estimates diverge from $qLAP_{LV-RV}$ values and from the true LAP values during the first couple of weeks of data. This is due to healing in and around the recently implanted electrodes, which affects impedance measurements. Hence, one advantage of the conduction delay-based techniques described herein (i.e. qLAP techniques) is that reliable estimates can be achieved even during the first few weeks following lead implant. (Note that the figure also provides the slope and baseline values used in calculating zLAP (based on admittance) and $qLAP_{LV-RV}$ (based on the LV-RV conduction delay).)

Returning to FIG. 5, at step 208, the pacer/ICD adjusts the timing delays (such as the LV-RV and AV delays) in an effort reduce $qLAP_{LV-RV}$ so as to mitigate CHF or other heart ailments. In this regard, the various pacing timing parameters noted above may be adaptively adjusted. That is, typically, at least the AV and LV-RV timing parameters are adjusted. Advantageously, the direction and magnitude of the adjustment need not be known in advance. Rather, the pacer/ICD makes an incremental adjustment in one timing parameter in one direction, then determines whether the adjustment improved $qLAP_{LV-RV}$ or not. If an improvement is gained, the pacer/ICD makes an additional incremental adjustment in that timing parameter in that same direction in an attempt to achieve still further improvement. If the adjustment has an adverse effect on $qLAP_{LV-RV}$, the pacer/ICD makes an incremental adjustment in the same timing parameter but in the opposite direction in an attempt to achieve an improvement in $qLAP_{LV-RV}$. The magnitudes of the adjustments are adaptively varied so as to further optimize the parameter. If the initial adjustment had no effect, the pacer/ICD selects a different timing parameter to adjust. Once a particular parameter is optimized, the pacer/ICD can select a different parameter. For example, once AV delay has been optimized, the VV pacing delay may then be optimized. The range within which the parameters are automatically adjusted can be restricted via device programming to ensure that the parameters remain within acceptable bounds.

Care should be taken when optimizing or adapting pacing parameters when the parameter that is to be optimized is the parameter that is initially measured and used to estimate qLAP. Such closed loop feedback techniques are not precluded but it is often appropriate to restrict the range through which the parameters are automatically adjusted or by providing other suitable feedback control techniques. For example, insofar as optimizing or adapting VV delays based on qLAP values derived from LV-RV delays are concerned, the VV delay may be adjusted from a qLAP value estimated based on LV-RV delays by defining suitable adjustment criteria. This is generally equivalent to a closed loop system where the feedback variable is optimized to a pre-established criterion (e.g. by keeping qLAP to less than 25 mmHg.). This is discussed more fully below. Similarly, qLAP could be used to adjust pacing sites to reach a pre-established estimated LAP goal.

Figure 7:
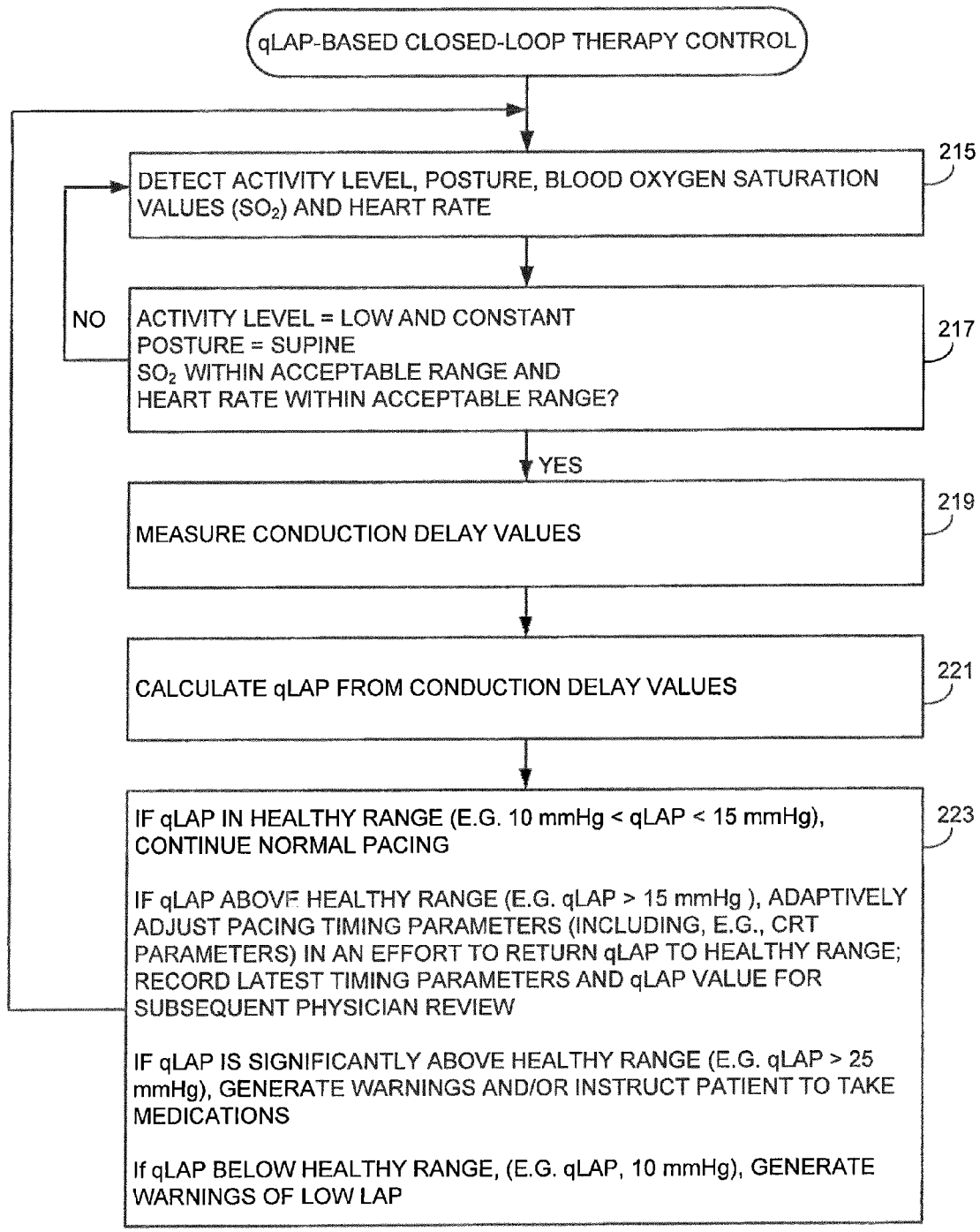
FIG. 7 is a flow diagram illustrating a closed-loop procedure for adaptively adjusting pacing parameters based on estimated cardiac pressure values obtained in accordance with the exemplary estimation technique of FIG. 5.

FIG. 7 provides an exemplary closed-loop adjustment procedure wherein pacing parameters are adaptively adjusted so as to reduce a qLAP but only under certain conditions. Beginning at step 215, the pacer/ICD detects detect patient activity level, patient posture, blood oxygen saturation values ($SO_2$) and heart rate. Patient activity may be detected using an accelerometer or other physical activity sensor mounted within the pacer/ICD itself or positioned elsewhere within the patient. Depending upon the implementation, the physical activity sensor may be employed in conjunction with an "activity variance" sensor, which monitors the activity sensor diurnally to detect the low variance in the measurement corresponding to a rest state. For a complete description of an activity variance sensor, see U.S. Pat. No. 5,476,483 to Bornzin et al., entitled "System and Method for Modulating the Base Rate during Sleep for a Rate-Responsive Cardiac Pacemaker." Techniques for detecting patient posture or changes in posture are set forth in U.S. patent application Ser. No. 0/329,233, of Koh et al., entitled "System and Method for Determining Patient Posture Based On 3-D Trajectory Using an Implantable Medical Device," now U.S. Pat. No. 7,149,579. Other techniques are set forth in U.S. Pat. No. 6,044,297 to Sheldon, et al. "Posture and Device Orientation and Calibration for Implantable Medical Devices." Techniques for detecting $SO_2$ are described in U.S. Pat. No. 5,676,141 to Hollub, entitled "Electronic Processor for Pulse Oximeters." Depending upon the particular application, either arterial $SO_2$ (i.e. $SaO_2$), or venous SO $SO_2$ (i.e. $SvO_2$), or both, may be detected and exploited. Heart rate may be derived from an IEGM.

At step 217, the pacer/ICD determines whether all of the following are true: (1) the patient is at rest and has been at rest for some predetermined amount of time, based on patient activity; (2) the posture is supine; (3) $SO_2$ is within an acceptable predetermined range consistent with patient rest; and (4) heart rate is within an acceptable predetermined range consistent with rest (such as a heart rate below 80 beats per minute (bpm)). If these conditions are met, the pacer/ICD proceeds to steps 219-223 to adaptively adjusting the pacing parameters. That is, at step 219, the pacer/ICD measures conduction delay values, such as LV-RV delays. At step 221, the pacer/ICD calculates qLAP from the measured delay using the techniques discussed above. At step 223, the pacer/ICD adaptively adjusts pacing parameters such as CRT timing parameters in an effort to maintain qLAP within a predetermined acceptable range and also records the latest timing parameters and qLAP values for subsequent physician review. For example, the pacer/ICD may be programmed to attempt to maintain qLAP within the range of 10-15 mmHg. In one example, if qLAP is initially found to be within that range, no pacing parameter adjustments are made. However, if qLAP is found to be in the range of 15-25 mmHg, then CRT parameter are adjusted in an attempt to reduce qLAP to within 10-15 mmHg. If qLAP is found to exceed 25 mmHg, then the pacer/ICD may be programmed to warning the patient (and/or the appropriate medical personal) and/or to initiate appropriate therapy. For example, if a drug pump is provided, the pacer/ICD may control the drug pump to deliver diuretics or other medications directed to reducing LAP (assuming such medications are available and have been found to be safe and effective for delivery via an implantable drug pump.) If no drug pump is provided, the pacer/ICD may relay instruction signals to the patient (and/or appropriate medical personnel) to direct the patient to take suitable medications. In this manner, medications directed to reducing LAP may be titrated. Alternatively, warnings may simply be generated that direct the patient to see his or her physician. The following summarizes one exemplary implementation of these strategies:

If qLAP in healthy range (e.g. 10 mmHg<qLAP<15 mmHg), continue normal pacing

If qLAP above healthy range (e.g. qLAP>15 mmHg), adaptively adjust pacing timing parameters (including, e.g., CRT parameters) in an effort to return qLAP to healthy range; record latest timing parameters and qLAP value for subsequent physician review If qLAP is significantly above healthy range (e.g. qLAP>25 mmHg), generate warnings and/or instruct patient to take medications If qLAP below healthy range, (e.g. qLAP, 10 mmHg), generate warnings of low LAP Still further, any CRT adjustments may be made based not only on qLAP but on other parameters as well. For example, adjustments may be made so as to maintain qLAP within a given range while also maintaining certain IEGM morphological parameters (such as P-wave width) within a certain range. As can be appreciated a wide range of feedback strategies and techniques may be exploited.

Processing then returns to step 215 and, so long as the conditions of step 217 are still met, the pacer/ICD will continually and incrementally adjust the pacing parameters using the adaptive procedure. This helps ensure that adjustments are made while the patient is in a particular resting state so that changes to qLAP due to factors other than the changes in the pacing parameters (such as patient activity) will not adversely affect the adaptive procedure. By looking at just qLAP values, which can be calculated fairly quickly, the procedure can typically be performed in near real-time. Once the patient becomes active again, further adaptive adjustments to pacing parameters are suspended until the patient is again at rest. Note that the list of patient status conditions in step 217 is merely exemplary. In other examples, more or fewer conditions may be used. For example, in other implementations, the patient need not necessarily be supine. Also, if the patient is subject to AF, the acceptable heart rate range may be expanded or that condition eliminated entirely so that frequent episodes of AF do not prevent adaptive adjustment of the pacing parameters.

Various additional techniques and strategies for adaptively optimizing pacing parameters may be employed, where appropriate, to supplement or enhance the techniques described herein. Examples are set forth in U.S. Pat. No. 11/231,081, filed Sep. 19, 2005,of Turcott, entitled "Rapid Optimization of Pacing Parameters," now U.S. Pat. No. 7,738,936; U.S. patent application Ser. No 11/199,619, filed Aug. 8, 2005, of Gill et al, entitled " System And Method For Determining Preferred Atrioventricular Pacing Delay Values Based On Intracardiac Electrogram Signals," now U.S. Pat. No. 7,505,813; U.S. Pat. No. 11/366,930, of Muller et aL, filed Mar. 1, 2006, entitled "System and Method for Determining Atrioventricular Pacing Delay based on Atrial Repolarization," now U.S. Pat. No. 7,643,878; U.S. patent application Ser. No. 10/928,586, of Bruhns et aL, entitled "System and Method for Determining Optimal Atrioventricular Delay based on Intrinsic Conduction Delays", filed Aug. 27, 2005, now U.S. Pat. No. 7,248,925; and U.S. Pat. No. 6,522,923 to Turcott, entitled "Methods, Systems and Devices for Optimizing Cardiac Pacing Parameters Using Evolutionary Algorithms." See, also, the adaptive adjustment techniques described in the above-cited patent application of Panescu et al. ( Ser. No. 11/558,914), now U.S. Pat. No. 8/712,519.

The locations of pacing sites may also be adaptively adjusted based on qLAP. In one particular example, the pacer/ICD is equipped with N electrodes in the RV, where N is an arbitrary number of electrodes. The pacer/ICD calculates qLAP when unipolar pacing is performed using each RV electrode, i.e. $RV_1$—case, $RV_2$—case, $RV_3$—case, etc. The pacer/ICD then selects the particular RV electrode that achieves the lowest value of qLAP for use in performing further pacing. Once optimal pacing sites are chosen, CRT timing parameters may be optimized using the techniques above for use with that particular pacing site. Similarly, the LV lead may carry multiple CRT pacing electrodes. In a similar fashion, optimal pacing configurations can be selected from the electrodes on the LV lead. Yet similarly, combined RV and LV pacing configurations may be selected to reduce qLAP. Alternatively, all these pacing electrodes can be separately, or individually, distributed on endocardial, epicardial or within myocardial tissue. The electrodes can be carried on separate leads, on multiple leads or implanted individually. Note that, whenever switching between pacing electrodes, new conversion factors will need to be applied/available. Accordingly, the pacer/ICD will need to have sufficient resources to store the many conversion factors and to keep track of which ones are well-calibrated and which ones are inaccurate (or otherwise not useable).

Calibration Techniques

Figure 8:
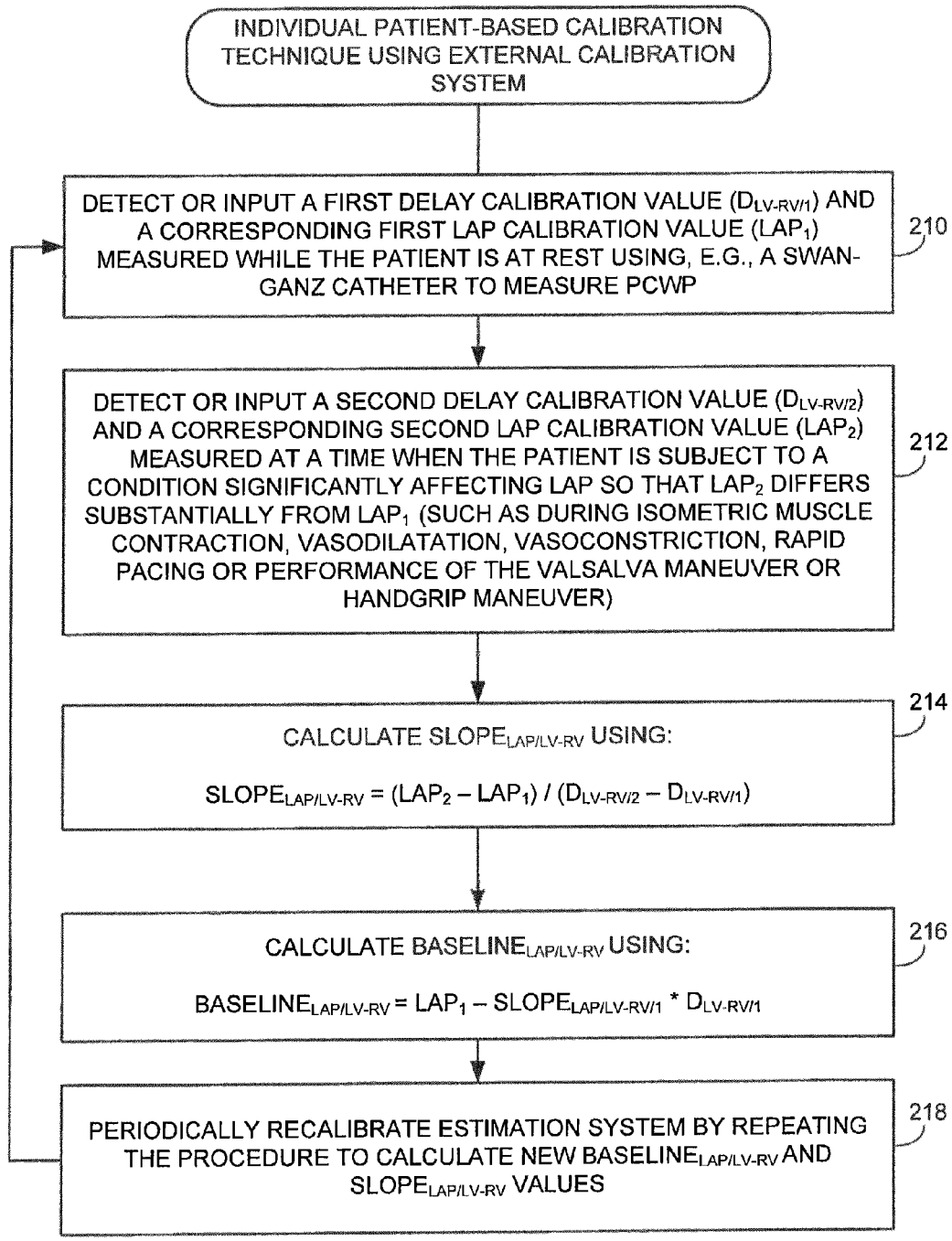
FIG. 8 is a flow diagram illustrating an exemplary procedure for calibrating the LV-RV delay-based LAP estimation technique of FIG. 5 using calibration parameters obtained within the patient in which the system is implanted.

A variety of techniques may be used to initially determine and subsequently adjust the conversion values ($Slope_{LAP/LV-RV}$ and $Baseline_{LAP/LV-RV}$), i.e. to calibrate the delay-based estimation technique of FIG. 5. FIG. 8 summarizes a technique wherein calibration is performed based on calibration values obtained within the particular patient in which the pacer/ICD is implanted. That is, the conversion values are optimized for use with the particular patient. The procedure of FIG. 8 is performed by a physician during the implant procedure of the pacer/ICD while venous access is readily available and a Swan-Ganz catheter can be easily inserted. The procedure in FIG. 8 may be repeated or performed alternatively at a follow-up session after implantation of the pacer/ICD. At step 210, an external calibration system (such as the external programmer of FIG. 15) detects or inputs a first delay calibration value ($D_{LV-RV/1}$) and a corresponding first LAP calibration value ($LAP_1$) measured while the patient is at rest. Preferably, the delay value ($D_{LV-RV/1}$) is detected by the pacer/ICD itself using its leads and its internal detection circuitry, then transmitted to the external system. Simultaneously, $LAP_1$ is detected using, e.g., a Swan-Ganz catheter to measure PCWP. The LAP value is also relayed to the external programmer.

At step 212, detects a second delay calibration value ($D_{LV-RV/1}$) and a corresponding second LAP calibration value ($LAP_2$) measured at a time when the patient is subject to a condition significantly affecting LAP so that $LAP_2$ differs substantially from $LAP_1$. For example, the physician may have the patient perform isometric muscle contractions, particular using thoracic muscles, so as to change LAP within the patient. Alternatively, the physician may administer vasodilatation or vasoconstriction medications, so as to change LAP, or may temporarily reprogram the pacer/ICD to perform rapid pacing, which also changes LAP. Still further, the physician may have the patient perform the Valsalva maneuver, which reduces effective LAP secondary to reduced venous return, or may instead have the patient perform the handgrip maneuver, which tends to increase LAP. (The Valsalva maneuver occurs when a patient forcibly exhales for about 15 seconds against a fixed resistance with a closed glottis while contracting the abdominal muscles. A sudden transient increase in intra-thoracic and intra-abdominal pressures occurs, which tends to empty the chambers of the heart of blood, such that within 1 to 2 seconds (phase I of the Valsalva maneuver) the effective right atrial and right ventricular pressures drop to zero, while following 5 seconds (Late phase II) the effective left atrial and left ventricular pressures tend to reach zero.) Again, the conduction delay value is detected by the pacer/ICD itself then transmitted to the external system.

Thus, after step 212, the external system has obtained at least two pairs of calibration values ($LAP_1$, $D_{LV-RV/1}$ and $LAP_2$, $D_{LV-RV/2}$) where the LAP values differ substantially from one another. Since the LV-RV conduction delay varies due to changes in LV chamber volume that correlate with changes in the LAP, the delay values likewise differ from one another, permitting reliable calculation of the slope and baseline values.

At step 214, the external system calculates $Slope_{LAP/LV-RV}$ using:

$$Slope_{LAP/LV-RV}=(LAP_2-LAP_1)/(D_{LV-RV/2}-D_{LV-RV/1}).$$

At step 216, the external system calculates $Baseline_{LAP/LV-RV}$ using:

$$Baseline_{LAP/LV-RV}=LAP_1-Slope_{LAP/LV-RV/1}*D_{LV-RV/1}$$

These values are then transmitted to the pacer/ICD for storage therein for use in estimating LAP based on newly detected delay values using the technique of FIG. 5. Preferably, qLAP values provided by the pacer/ICD are compared with LAP values detected using the Swan-Ganz catheter to verify that the estimation system of the pacer/ICD has been properly calibrated.

As noted, LV-RV conduction delays are not the only delays that might be used in estimating LAP or other cardiac pressure values. Hence, the first and second delay calibration values are also more generally referred to herein as $D_1$ and $D_2$. The external system calculates Slope using:

$$Slope=(Pressure_2-Pressure_1)/(D_2-D_1).$$

The external system calculates Baseline using:

$$Baseline=Pressure_1-Slope*D_1.$$

Figure 9:
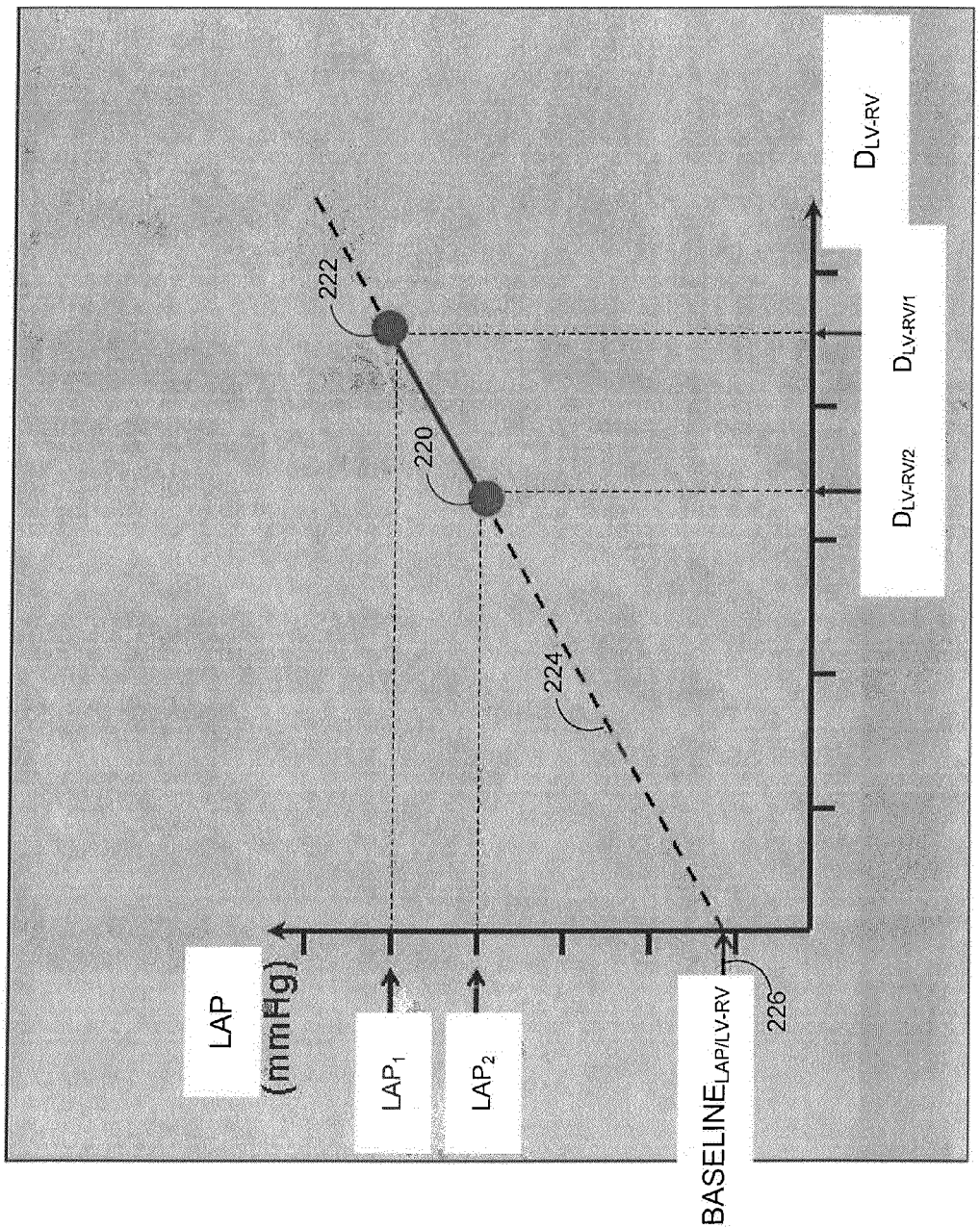
FIG. 9 is a graph illustrating a linear relationship between qLAP and LV-RV delay calibration values exploited by the calibration technique of FIG. 8.

FIG. 9 illustrates an exemplary pair of calibration values 220, 222, along with exemplary slope 224 and baseline values 226 derived therefrom using the technique of FIG. 8. Although only two pairs of calibration values are used in the example of FIG. 8, it should be understood that additional pairs of calibration values might be obtained. Linear regression techniques may be used to derive slope and baseline values from a plurality of pairs of calibration values. Also, as indicated by step 218, the recalibration procedure of FIG. 8 can be repeated periodically (such as during subsequent follow-up sessions with the patient) to update both the slope and baselines values to respond to changes, if any, that may arise within the patient, perhaps due to scarring near the sensing electrodes. Alternatively, a re-calibration technique may be performed by the pacer/ICD itself that re-calibrates only the baseline value. This is summarized in FIG. 10.

Figure 10:
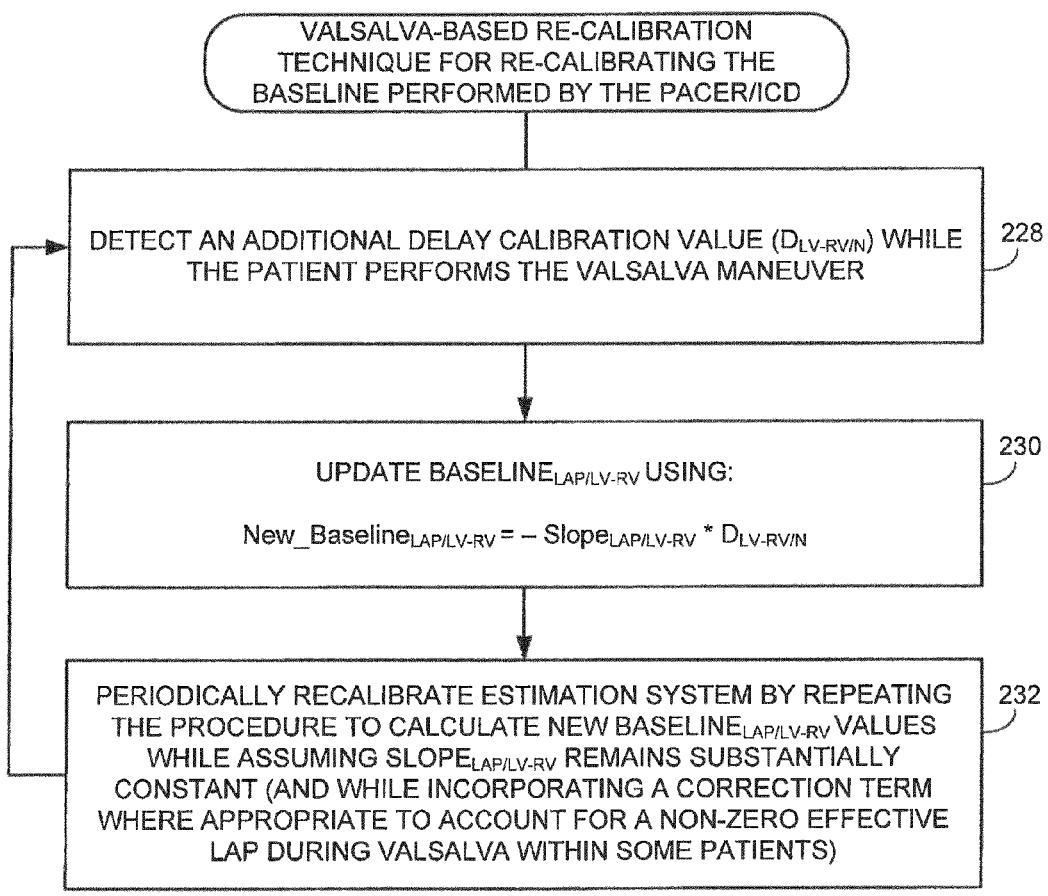
FIG. 10 is a flow diagram illustrating an exemplary procedure for re-calibrating the baseline value of the LV-RV delay-based LAP estimation technique of FIG. 5 using additional calibration parameters obtained within the patient while performing the Valsalva maneuver.

FIG. 10 illustrates a recalibration procedure performed by the pacer/ICD to re-calibrate the baseline value. The procedure exploits the assumption that the slope value, once calculated for a particular patient, typically does not change significantly within the patient. This allows the baseline value to be re-calibrated independently of the slope value. At step 228, the pacer/ICD detects an additional delay calibration value ($D_{LV-RV/N}$) while the patient performs the Valsalva maneuver. As already explained, during the Valsalva maneuver effective LAP drops to zero or near zero. Hence, a separate measurement of effective LAP is not required. Under the assumption that effective LAP drops to zero at the time when the additional delay value ($D_{LV-RV/N}$) is measured, the baseline value can be re-calculated, at step 230, based on the previous slope and the new delay value ($D_{LV-RV/N}$) using:

$$New\_Baseline_{LAP/LV-RV}=-Slope_{LAP/LV-RV}*D_{LV-RV/N}.$$

A particularly attractive feature of this recalibration procedure is that it is non-invasive and can be performed in the ambulatory setting in the physician's office during a routine follow-up visit. Preferably, re-calibration is performed while the patient is clinically stable.

In some patients with diastolic heart failure and poor left ventricular compliance who may have higher cardiac filling pressures (PCWP>20 mmHg) even when well compensated, the effective LAP may not drop completely to zero during a Valsalva maneuver and a correction term may need to be applied to account for this possibility. (See, for example, FIG. 5 of U.S. Patent Application 2004/0019285 of Eigler, et al., entitled "Apparatus for Minimally Invasive Calibration of Implanted Pressure Transducers," which is incorporated by reference herein in its entirety.)

In order to determine whether a particular patient requires such a correction term, a third measurement of the conduction delay ($D_3$) during the original calibration procedure FIG. 8 should be obtained while the patient is performing the Valsalva maneuver. This assumes that $D_1$ and $D_2$ were not obtained during a Valsalva maneuver. The correction term ($qLAP_{VALSALVA}$) is simply computed using:

$$qLAP_{VALSALVA} = D_3 * Slope_{LAP/LV-RV} + Baseline_{LAP/LV-RV}$$

wherein $qLAP_{VALSALVA}$ is an effective LAP pressure value. Ideally, if the blood volume inside the left atrium significantly decreases during the Valsalva maneuver, then $qLAP_{VALSALVA}$ will be near zero. Step 230 may alternatively be computed using:

$$New\_Baseline_{LAP/LV-RV} = qLAP_{VALSALVA} - Slope_{LAP/LV-RV} * D_N.$$

The response of intracardiac pressures to the Valsalva is discussed in McClean et al., "Noninvasive calibration of cardiac pressure transducers in patients with heart failure: An aid to implantable hemodynamic monitoring and therapeutic guidance", Journal of Cardiac Failure, Vol. 12 No. 7 2006, pp 568-576. It is described therein that during the Valsalva maneuver the effective PCWP reduces nearly to zero as described above. A similar observation was observed for other chambers of the heart. In particular, the effective residual pressure within a specific cardiac chamber ($P_{eff}$) was computed as the difference between the measured intracardiac pressure ($P_{intracardiac}$) and the simultaneous intrathoracic or airway pressure ($P_{airway}$) averaged over the time interval from 5 to 10 seconds after the initiation of the Valsalva maneuver (Late phase II). The effective intracardiac pressure ($P_{eff}$) is computed using:

$$P_{eff} = P_{intracardiac} - P_{airway}$$

where ($P_{airway}$) is detected, e.g., using an external pressure detection system. See, for example, the upper airway apparatus of FIG. 2 of U.S. Patent Application 2004/0019285 of Eigler, at al., cited above. Thus, in order to estimate the effective LAP ($LAP_{eff}$) during the Valsalva maneuver one may obtain this measurement directly by computing average of the difference between the PCWP and the simultaneous airway pressure over the interval from 5 to 10 seconds following the initiation of the Valsalva maneuver (late Phase II). This may be written more specifically as:

$$LAP_{eff} = PCWP - P_{airway}$$

and $LAP_{eff}$ may be used alternatively as the correction term described above.

The new baseline value is then used when converting additional conduction delay values to effective qLAP values (step 204 of FIG. 5.) As indicated by step 232, the pacer/ICD can periodically recalibrate its estimation system by repeating the procedure to calculate new $Baseline_{LAP/LV-RV}$ values while assuming $Slope_{LAP/LV-RV}$ remains substantially constant and using the correction term where appropriate.

In practice, the procedure of FIG. 10 may be initiated by periodically having the pacer/ICD transmit a signal to the bedside monitor providing instructions to the patient to perform the Valsalva maneuver. The pacer/ICD detects the new conduction delay value during the Valsalva maneuver and updates the baseline value. The pacer/ICD may be additionally programmed to verify that the patient actually performed the maneuver by, e.g., analyzing changes in respiration (as detected using otherwise conventional respiration detection techniques) to verify that respiratory patterns consistent with the Valsalva maneuver occur. The pacer/ICD can also time its detection of the additional conduction delay value based on the respiratory signals to help ensure that the new conduction delay value is measured at a point when effective LAP is expected to be zero. Alternatively, the re-calibration technique may be performed only under the supervision of a physician or other clinician during a follow-up session with the patient. Still, the re-calibration procedure eliminates the need to directly measure effective LAP during the follow-up using a Swan-Ganz catheter. The catheter is only employed during the original calibration procedure. Thus, FIG. 10 illustrates a technique wherein the baseline value is re-calibrated by the pacer/ICD under the assumption that slope does not change by exploiting the Valsalva maneuver. The Valsalva maneuver may also be exploited to re-calibrate both slope and baseline, if needed within a particular patient. This is illustrated in FIGS. 11 and 12.

Figure 11:
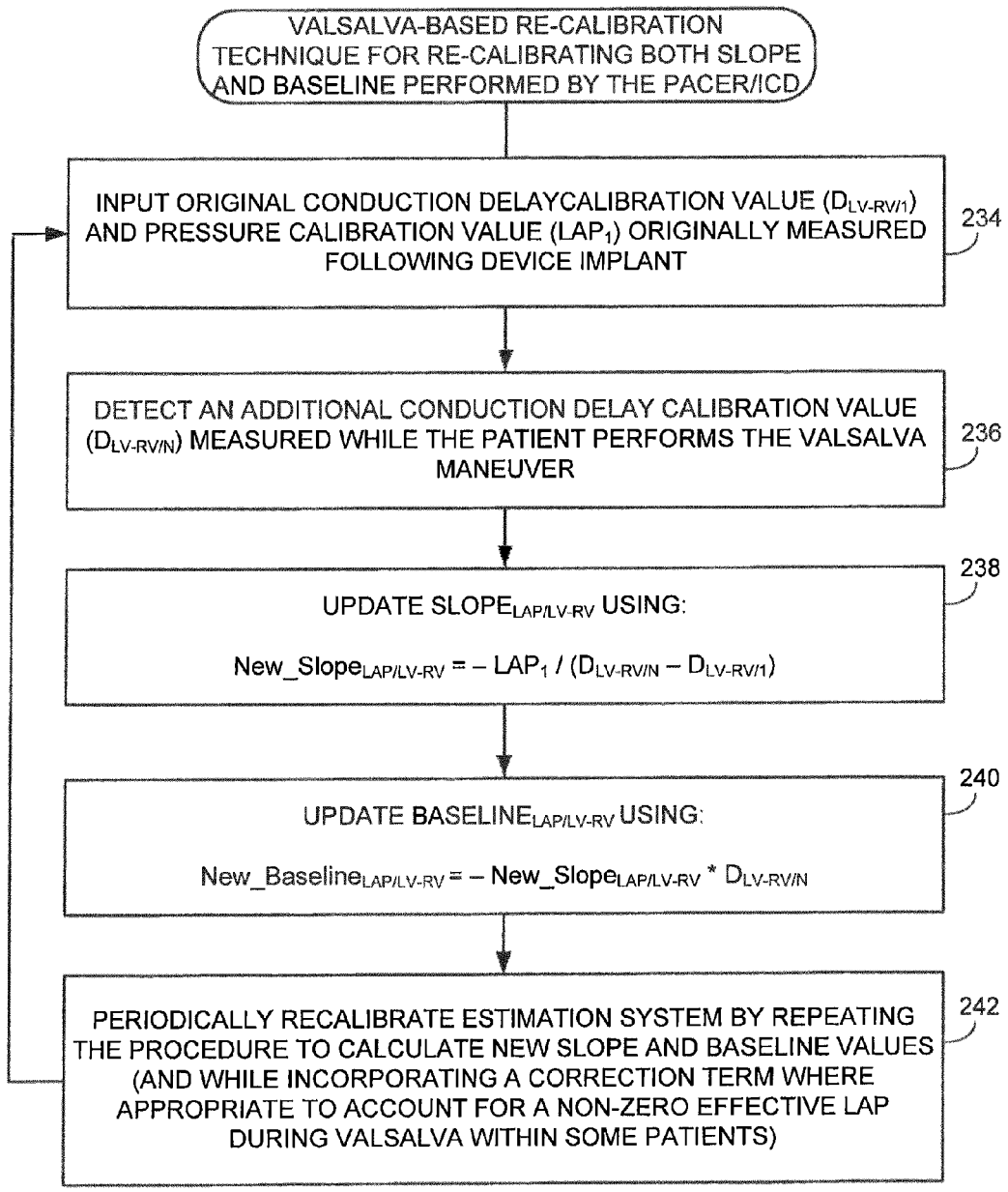
FIG. 11 is a flow diagram illustrating an exemplary procedure for re-calibrating both slope and baseline values of the LV-RV delay-based LAP estimation technique of FIG. 5 using additional calibration parameters obtained within the patient while performing the Valsalva maneuver.
Figure 12:
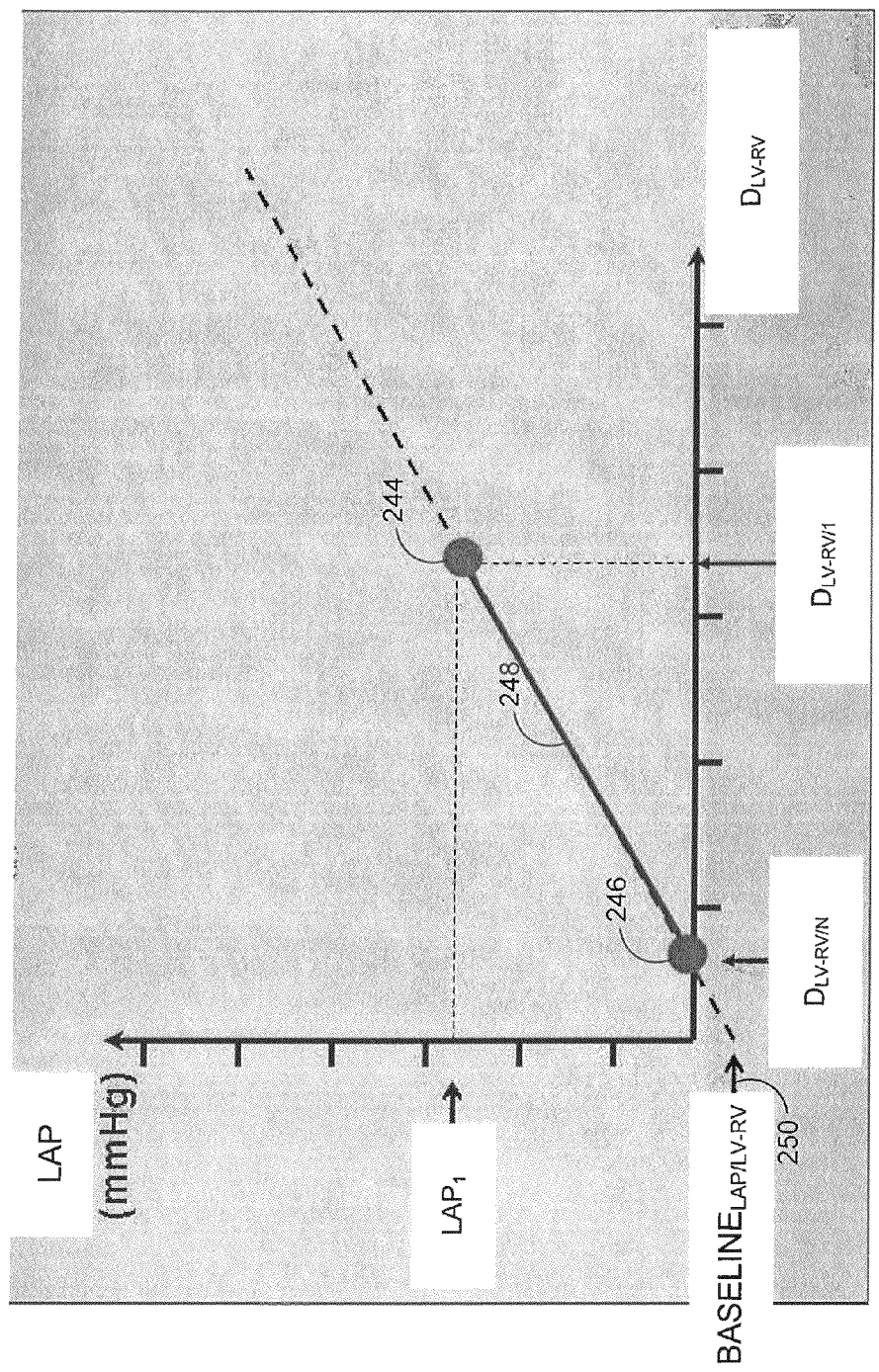
FIG. 12 is a graph illustrating a linear relationship between qLAP and LV-RV delay calibration values exploited by the re-calibration technique of FIG. 11, and, in particular, illustrating a zero LAP value obtained within the patient during the Valsalva maneuver.

FIG. 11 summarizes a recalibration procedure performed by the pacer/ICD to re-calibrate both the slope and baseline values. The procedure can be used in patients where the slope value changes. At step 234, the pacer/ICD inputs the original conduction delay calibration value ($D_{LV-RV/1}$) and effective pressure calibration value ($LAP_1$) originally measured following device implant (FIG. 8) or during a previous calibration procedure. The assumption is that $LAP_1$ is unchanged from the previous calibration procedure. At step 236, the pacer/ICD detects an additional conduction delay calibration value ($D_{LV-RV/N}$) while the patient performs the Valsalva maneuver. As already noted, during the Valsalva maneuver effective LAP typically drops to at or near zero and so separate measurement of effective LAP is not required. Rather, it is assumed that effective LAP is zero when the additional conduction delay value ($D_{LV-RV/N}$) is measured, thus allowing the slope to be re-calculated, at step 238, using:

$$New\_Slope_{LAP/LV-RV} = -LAP_1 / (D_{LV-RV/N} - D_{LV-RV/1}).$$

Once the new slope value is calculated, the new baseline value can be calculated, at step 240, using:

$$New\_Baseline_{LAP/LV-RV} = -New\_Slope_{LAP/LV-RV} * D_{LV-RV/N}.$$

More generally:

$$Slope = -Pressure_1 / (D_N - D_1) \text{ and}$$

$$Baseline = -Slope * D_N$$

The new slope and baseline values are then used when converting additional conduction delay values to effective qLAP values (step 206 of FIG. 5.) As indicated by step 242, the pacer/ICD can periodically recalibrate its estimation system by repeating the procedure to calculate new $Baseline_{LAP/LV-RV}$ and $Slope_{LAP/LV-RV}$ values and using the correction term where appropriate. As with the procedure of FIG. 10, the procedure of FIG. 11 may be initiated by periodically having the pacer/ICD transmit a signal to the bedside monitor providing instructions to the patient to perform the Valsalva maneuver or the procedure may be performed under the supervision of a physician or other clinician.

FIG. 12 illustrates an exemplary pair of calibration values 244, 246, along with exemplary slope 248 and baseline values 250 derived therefrom using the technique of FIG. 11. The first pair of calibration values 244 is obtained following implant. The second pair of calibration values 246 is obtained during the re-calibration procedure while the patient performs the Valsalva maneuver. Since the Valsalva maneuver is being performed, the effective LAP value of the second pair of calibration values 246 is zero and so the pressure need not be measured. The conduction delay value of the second pair along with the pressure and conduction delay values of the first pair are used to calculate the new slope 244 and baseline values 250 using the equations of FIG. 11.

Figure 13:
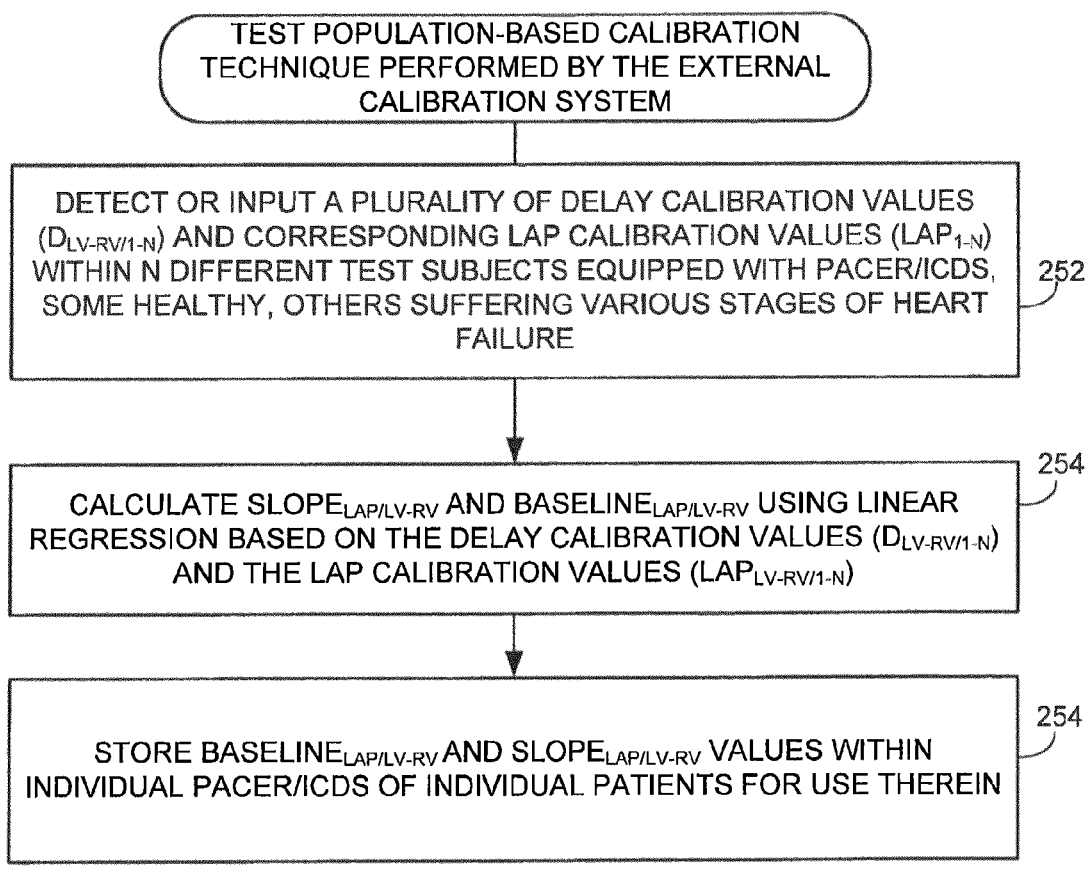
FIG. 13 is a flow diagram illustrating an exemplary procedure for calibrating the LAP-based technique of FIG. 5 using calibration parameters obtained from a population of test subjects.

Turning now to FIG. 13, techniques are summarized for calibrating or re-calibrating the conduction delay-based estimation procedure based on data from a population of human patients or human test subjects. In the specific example of FIG. 13, data is obtained from a plurality of test patients subject to various stages of heart failure and have various LAP values. Beginning at step 252, the external calibration system detects or inputs a plurality of conduction delay calibration values ($D_{LV-RV/1-N}$) and corresponding LAP calibration values ($LAP_{1-N}$) within N different human test subjects equipped with pacer/ICDs, some healthy, others suffering differing stages of heart failure, i.e. differing levels of severity of heart failure. The conduction delay values are detected by the pacer/ICDs of the test subjects, then relayed to the external calibration system. The LAP values may be obtained using Swan-Ganz catheters or the like. Since the test subjects exhibit differing stages of heart failure, differing values of LAP are thereby exhibited. At step 254, the external system then calculates $Slope_{LAP/LV-RV}$ and $Baseline_{LAP/LV-RV}$ values using linear regression based on the conduction delay calibration values ($D_{LV-RV/1-N}$) and the LAP calibration values ($LAP_{1-N}$). At step 256, the external system then stores the $Slope_{LAP/LV-RV}$ and $Baseline_{LAP/LV-RV}$ values within individual pacer/ICDs of individual patients for use therein. By obtaining data from a population of test subjects, the slope and baseline values are therefore likely to be effective within a wide range of patients. In some patients, these values may be sufficient to provide an adequate estimate of LAP. In other patients, these values may be used as starting points for further re-calibration. For example, the slope value obtained via the technique of FIG. 13 may be used within a wide range of patients along with patient-specific baseline values obtained using the baseline-only re-calibration procedure of FIG. 10.

Thus, a variety of techniques for calibrating the procedure, estimating LAP and then tracking heart failure are provided. These may be supplemented by using other non-conduction delay-based cardiac pressure detection and heart failure detection techniques. In some implementations, before an alarm is activated or any therapy is automatically delivered, the pacer/ICD employs at least one other detection technique to corroborate the detection of heart failure. Techniques for detecting or tracking heart failure are set forth the following patents and patent applications: U.S. Pat. No.: 6,328,699 to Eigler, et al., entitled "Permanently Implantable System and Method for Detecting, Diagnosing and Treating Congestive Heart Failure"; U.S. Pat. No.: 6,970,742 to Mann, et al., entitled "Method for Detecting, Diagnosing, and Treating Cardiovascular Disease"; U.S. Pat. No. 7,115,095 to Eigler, et al., entitled "Systems and Methods for Detecting, Diagnosing and Treating Congestive Heart Failure"; U.S. patent application Ser. No. 11/100,008, of Kil et al., entitled "System And Method For Detecting Heart Failure And Pulmonary Edema Based On Ventricular End-Diastolic Pressure Using An Implantable Medical Device", filed Apr. 5, 2005, now U.S. Pat. No. 7,437,192; U.S. patent application Ser. No. 11/014,276, of Min et al., entitled "System And Method For Predicting Heart Failure Based On Ventricular End-Diastolic Volume/Pressure Using An Implantable Medical Device", filed Dec. 15, 2004, now U.S. Pat. No. 7,272,443; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004, now U.S. Pat. No. 7,505,814, and U.S. patent application Ser. No 10/346,809, of Min et al., entitled "System and Method for Monitoring Cardiac Function via Cardiac Sounds Using an Implantable Cardiac Stimulation Device," filed Jan. 17, 2003, now U.S. Pat. No. 7,139,609. See also: U.S. Pat. No. 6,572,557, to Tchou, et al., cited above, U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device For Monitoring Congestive Heart Failure." Also, other calibration procedures may potentially be exploited in connection with the calibration techniques described herein. See, for example, U.S. Patent Publication No. 2004/0019285 of Eigler, et al., entitled "Apparatus For Minimally Invasive Calibration Of Implanted Pressure Transducers," now U.S. Pat. No. 7,862,513, particularly the various linear regression techniques discussed therein. Also, see the calibration procedures set forth in: U.S. patent application Ser. No. 11/559,235, by Panescu et al., entitled "System and Method for Estimating Cardiac Pressure Using Parameters Derived from Impedance Signals Detected by an Implantable Medical Device," cited above.

The examples above primarily pertain to estimating LV-RV delays. However, as already noted, other conduction delays can be used to estimate LAP. In general, any conduction delay that is affected by a particular cardiac pressure parameter might be exploited to estimate that cardiac pressure parameter. For example, LAP may also be estimated from AV delays. AV may be determined in much the same manner as LV-RV delays are determined (i.e. paced on pacer or sensed atrial and ventricular events.) Also, the morphology of the P-wave may be exploited to estimate AV delays (such as its shape or width). Typically, the wider the P-wave, the longer the AV delay. The narrower the P-wave, the shorter the AV delay. The morphology of atrial evoked responses may also be exploited to estimate AV delay. The QuickOpt code of the appendix may be modified as needed to provide these parameters. The following is a list of parameters that generally can be exploited to estimate LAP or other cardiac pressure parameter and which can be obtained from the QuickOpt code of the appendix or from modified versions thereof:

A sense and A pace wave duration (indicates LA dilation and qLAP)

V sense: RV-LV conduction delay

RV pace-LV pace delay; LV-RV pace delay; or differences therebetween, including any appropriate correction terms.

PR and AR: atrio-ventricular delays.

RV-LV pace delay minus pacing latency (which is an alternative to V sense that tests for heart block in patients.)

Although primarily described with respect to examples having a pacer/ICD, other implantable medical devices may be equipped to exploit the techniques described herein, For the sake of completeness, an exemplary pacer/ICD will now be described, which includes components for performing the functions and steps already described. Also, an exemplary external programmer will be described, which includes components for performing the calibration steps already described.

Exemplary Pacer/ICD

Figure 15:
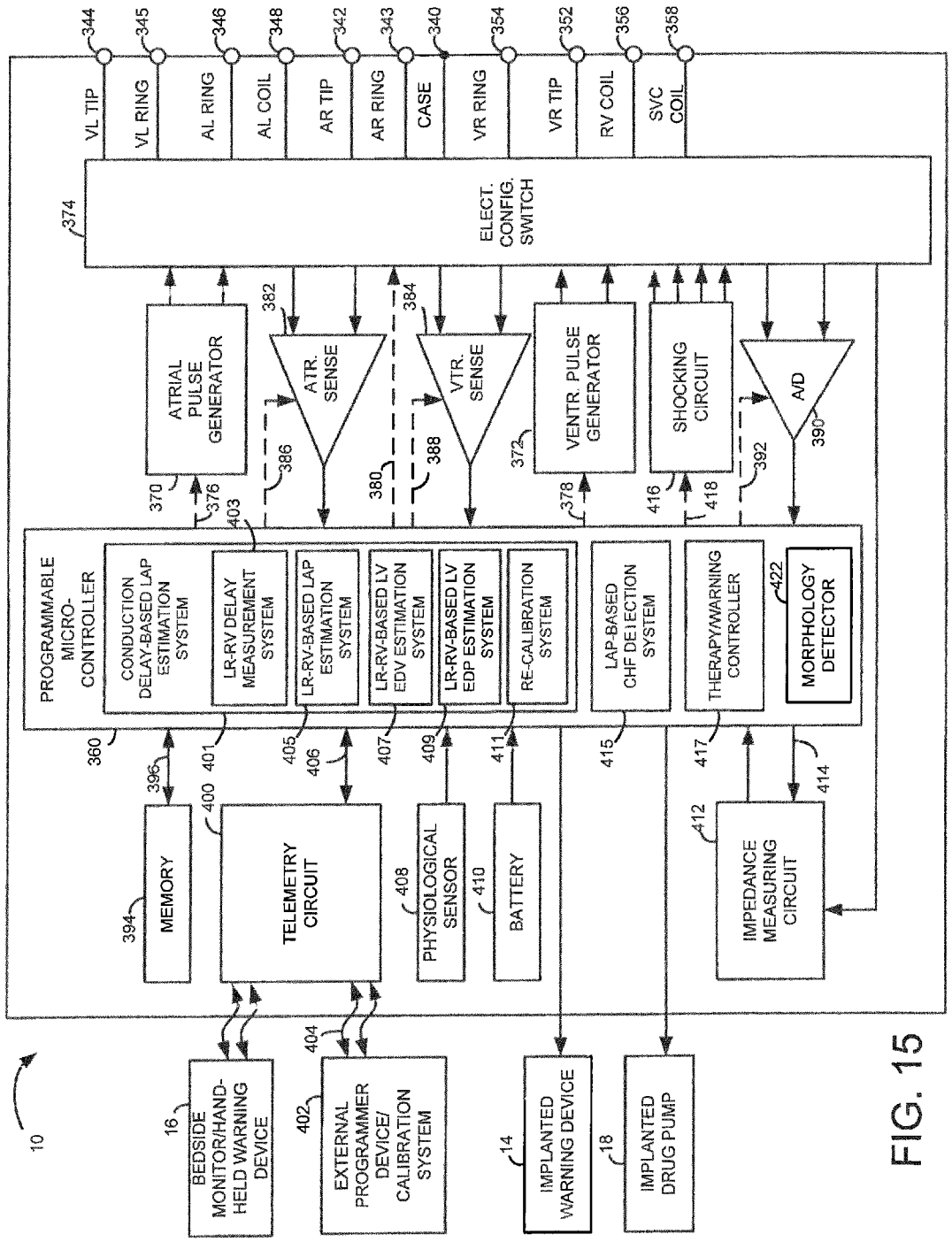
FIG. 15 is a functional block diagram of the pacer/ICD of FIG. 14, illustrating basic circuit elements that provide cardioversion, defibrillation and/or pacing stimulation in the heart and particularly illustrating components for estimating LAP based on conduction delays and for adaptively adjusting pacing parameters in response thereto.
Figure 16:
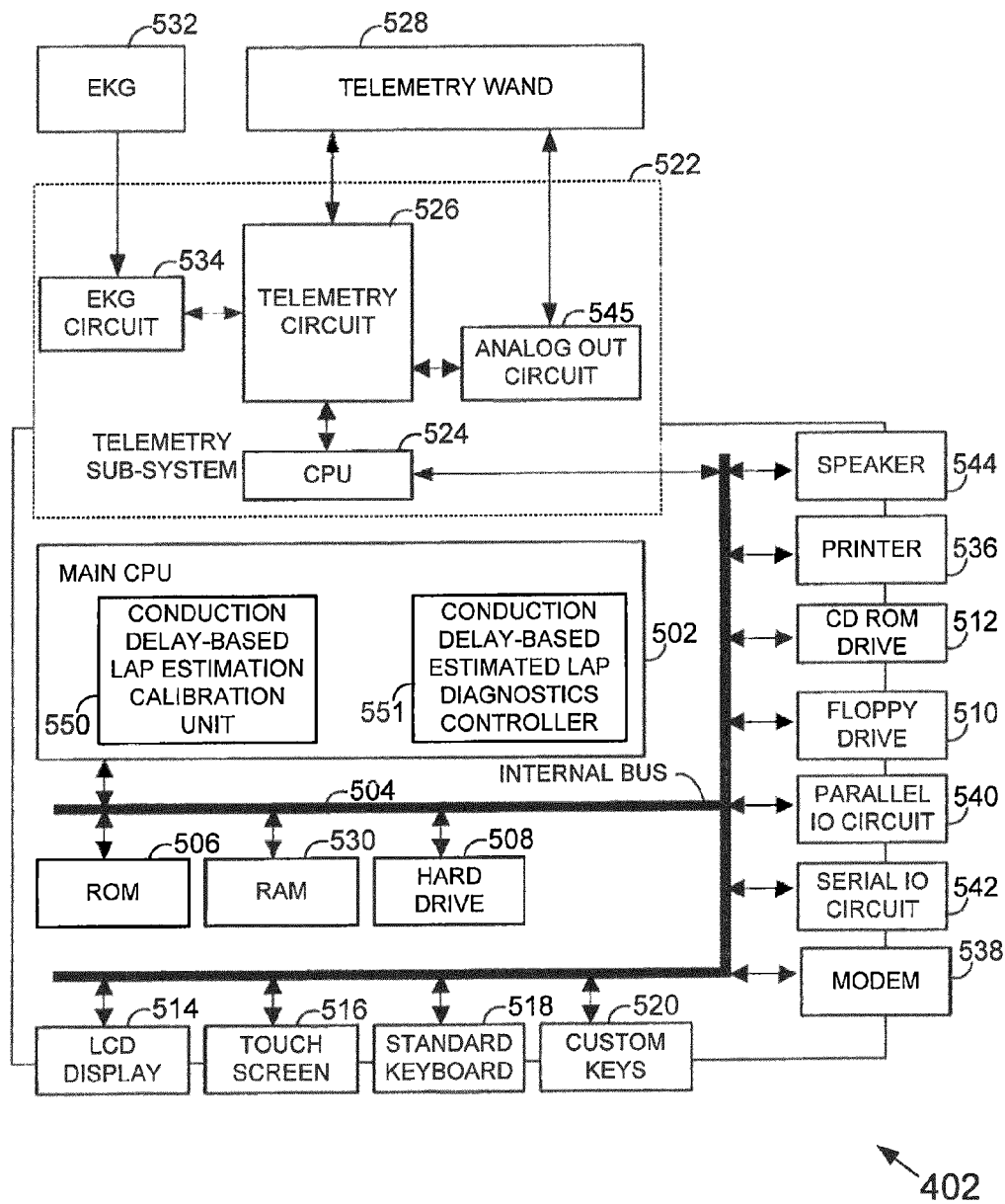
FIG. 16 is a functional block diagram illustrating components of a device programmer of FIG. 15, and in particular illustrating a programmer-based LAP estimation calibration system.

With reference to FIGS. 14 and 15, a description of an exemplary pacer/ICD will now be provided. FIG. 14 provides a simplified block diagram of the pacer/ICD, which is a dual-chamber stimulation device capable of treating both fast and slow arrhythmias with stimulation therapy, including cardioversion, defibrillation, and pacing stimulation, and also capable of estimating LAP or other forms of cardiac pressure using impedance signals. To provide other atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 324 is designed to receive atrial and ventricular cardiac signals and to deliver left ventricular pacing therapy using at least a left ventricular tip electrode 326 and a LV ring electrode 325, left atrial pacing therapy using at least a left atrial ring electrode 327, and shocking therapy using at least a left atrial coil electrode 328. With this configuration, biventricular pacing can be performed. Although only three leads are shown in FIG. 14, it should also be understood that additional leads (with one or more pacing, sensing and/or shocking electrodes) might be used and/or additional electrodes might be provided on the leads already shown. An interventricular conduction delay 101 already discussed, is also shown in FIG. 14.

A simplified block diagram of internal components of pacer/ICD 10 is shown in FIG. 15. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 15, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 345, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left ventricular ring terminal ($V_L$ RING) 345, a left atrial ring terminal ($A_L$ RING) 346, and a left atrial shocking terminal ($A_L$ COIL) 348, which are adapted for connection to the left ventricular ring electrode 326, the left atrial ring electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 15, an atrial pulse generator 370 and a ventricular pulse generator 372 generate pacing stimulation pulses for delivery by the right atrial lead 320, the right ventricular lead 330, and/or the CS lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, CS lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the CS lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, VV delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 15. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 15, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used. The impedance measuring circuit 412 also detects the impedance signals discussed above if zLAP is to be estimated, in addition to qLAP. That is, impedance measuring circuit 412 is an electrical impedance (Z) detector operative to detect an electrical impedance (Z) signal within the patient along at least one sensing vector wherein impedance is affected by cardiac pressure.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 4-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Insofar as LAP estimation is concerned, the microcontroller includes a conduction delay-based LAP estimation system 401 operative to estimate LAP or other forms of cardiac pressure based on parameters derived from conduction delays using the techniques described above. That is, the estimation system is operative to: measure an electrical conduction delay in the heart of the patient and estimate cardiac pressure within the patient from the electrical conduction delay. In this example, estimation system 401 includes: an LV-RV delay measurement system 403 operative to measure interventricular conduction delays within the patient and an LV-RV-based LAP estimation system 405 operative to estimated LAP from the measured interventricular delays. The estimation system also includes, in this example, an LV-RV-based LV EDV estimation system 407 operative to estimate LV EDV from the measured interventricular delays and an LV-RV-based LV EDP estimation system 409 operative to estimate LV EDP from the measured interventricular delays. Estimation system 401 also includes a re-calibration unit or system 411 operative to re-calibrate the conversion factors discussed above. An LAP-based CHF detection system 415 is provide to detect and track CHF based on LAP. Warning and/or notification signals are generated, when appropriate, by a therapy/warning controller 417 then relayed to the bedside monitor 18 via telemetry system 400 or to external programmer 402 (or other external calibration system.) Controller 417 can also controller an implantable drug pump, if one is provided, to deliver appropriate medications. Controller 417 also controls the adaptive adjustment of CRT parameters and other pacing parameters, as discussed above. Terminals for connecting the implanted warning device and the implanted drug pump to the pacer/ICD are not separately shown. Diagnostic data pertaining to LAP, CHF, therapy adjustments, etc., is stored in memory 394.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Exemplary External Programmer

FIG. 16 illustrates pertinent components of an external programmer 402 for use in programming the pacer/ICD of FIG. 15 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 402 may also be capable of processing and analyzing data received from the implanted device and from the EKG leads to, for example, render preliminary diagnosis as to medical conditions of the patient or to the operations of the implanted device.

Now, considering the components of programmer 402, operations of the programmer are controlled by a CPU 502, which may be a generally programmable microprocessor or microcontroller or may be a dedicated processing device such as an application specific integrated circuit (ASIC) or the like. Software instructions to be performed by the CPU are accessed via an internal bus 504 from a read only memory (ROM) 506 and random access memory 530. Additional software may be accessed from a hard drive 508, floppy drive 510, and CD ROM drive 512, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 514 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 516 overlaid on the LCD display or through a standard keyboard 518 supplemented by additional custom keys 520, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 402 to retrieve data stored within any implanted devices and to also retrieve EKG data from EKG leads, if any, coupled to the patient. To this end, CPU 502 transmits appropriate signals to a telemetry subsystem 522, which provides components for directly interfacing with the implanted devices, and the EKG leads. Telemetry subsystem 522 includes its own separate CPU 524 for coordinating the operations of the telemetry subsystem. Main CPU 502 of programmer communicates with telemetry subsystem CPU 524 via internal bus 504. Telemetry subsystem additionally includes a telemetry circuit 526 connected to telemetry wand 528, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 534 for receiving surface EKG signals from a surface EKG system 532. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 402 either within a random access memory (RAM) 530, hard drive 508 or within a floppy diskette placed within floppy drive 510. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 402, the implanted devices may be further controlled to transmit additional data in real time as it is detected by the implanted devices, such as additional IEGM data, lead impedance data, and the like. Additionally, or in the alternative, telemetry subsystem 522 receives EKG signals from EKG leads 532 via an EKG processing circuit 534. As with data retrieved from the implanted device itself, signals received from the EKG leads are stored within one or more of the storage devices of the external programmer. Typically, EKG leads output analog electrical signals representative of the EKG. Accordingly, EKG circuit 534 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 502, the programming commands are converted to specific programmable parameters for transmission to the implanted devices via telemetry wand 528 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information, Any or all of the information displayed by programmer may also be printed using a printer 536.

Additionally, CPU 502 also preferably includes a conduction delay-based LAP estimation calibration unit 550 operative to perform the calibration procedures described above. CPU 502 also preferably includes a conduction delay-based estimated LAP diagnostics controller 551 operative to control the display of estimated LAP values and related diagnostics. As already noted, physicians are often more familiar with LAP values than conduction delay values and hence benefit from LAP-based diagnostics displays that graphically illustrates changes in LAP within the patient, such as changes brought on by heart failure.

Programmer/monitor 402 also includes a modem 538 to permit direct transmission of data to other programmers via the public switched telephone network (PSTN) or other interconnection line, such as a T1 line or fiber optic cable. Depending upon the implementation, the modem may be connected directly to internal bus 504 may be connected to the internal bus via either a parallel port 540 or a serial port 542. Other peripheral devices may be connected to the external programmer via parallel port 540 or a serial port 542 as well. Although one of each is shown, a plurality of input output (IO) ports might be provided. A speaker 544 is included for providing audible tones to the user, such as a warning beep in the event improper input is provided by the physician. Telemetry subsystem 522 additionally includes an analog output circuit 545 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 16 are intended merely to provide an overview of the operation of programmer and are not intended to describe in detail every feature of the hardware and software of the programmer and is not intended to provide an exhaustive list of the functions performed by the programmer.

In the foregoing descriptions, LAP or other cardiac pressure values are estimated from conduction delay values. A variety of techniques were set forth for determining or measuring the delay values. In the following section, techniques are set forth for estimating delay values from admittance or impedance measurements. Note, though, that the estimated delay values are not necessarily used to then estimate LAP. Rather, the estimated delay values may be used for any suitable purpose. In particular, heart failure may be tracked based on the estimated delay values. That is, whereas the foregoing set forth techniques inter alia for tracking heart failure based on LAP values estimated from measured conduction delays, the following section sets forth techniques for tracking heart failure based on conduction delays estimated from measured impedance or admittance values. The two general techniques may be used in conjunction, where appropriate.

Admittance/Impedance-Based Delay Estimation Techniques

Turning now to FIGS. 17-20, system and methods for estimating conduction delays from admittance or impedance values and for tracking heart failure based on the estimated conduction delays will be briefly summarized. The examples described here principally exploit measured impedance values. However, as impedance is the reciprocal of admittance, measured admittance values can alternatively be exploited. Briefly, with reference to FIG. 17, impedance values are measured at block 600 from which conduction delay values are estimated at block 602. The delay values are used to detect heart failure events, at block 604, or to perform heart failure trending. A calibration block is also provided for calibrating the impedance-to-delay estimation procedure. That is, when the delays are estimated via block 602, supervising personnel can verify the estimations are correct by comparing the estimated delays to QuickOpt-based delays obtained in the physician's office. Any difference therebetween can then be used to adjust or calibrate the impedance to delay estimation procedure. Once properly calibrated, impedance measurements (block 608) may be used by the pacer/ICD to estimate conduction delays (block 610), from which heart failure events (or heart failure trends) 612 are detected.

Figure 18:
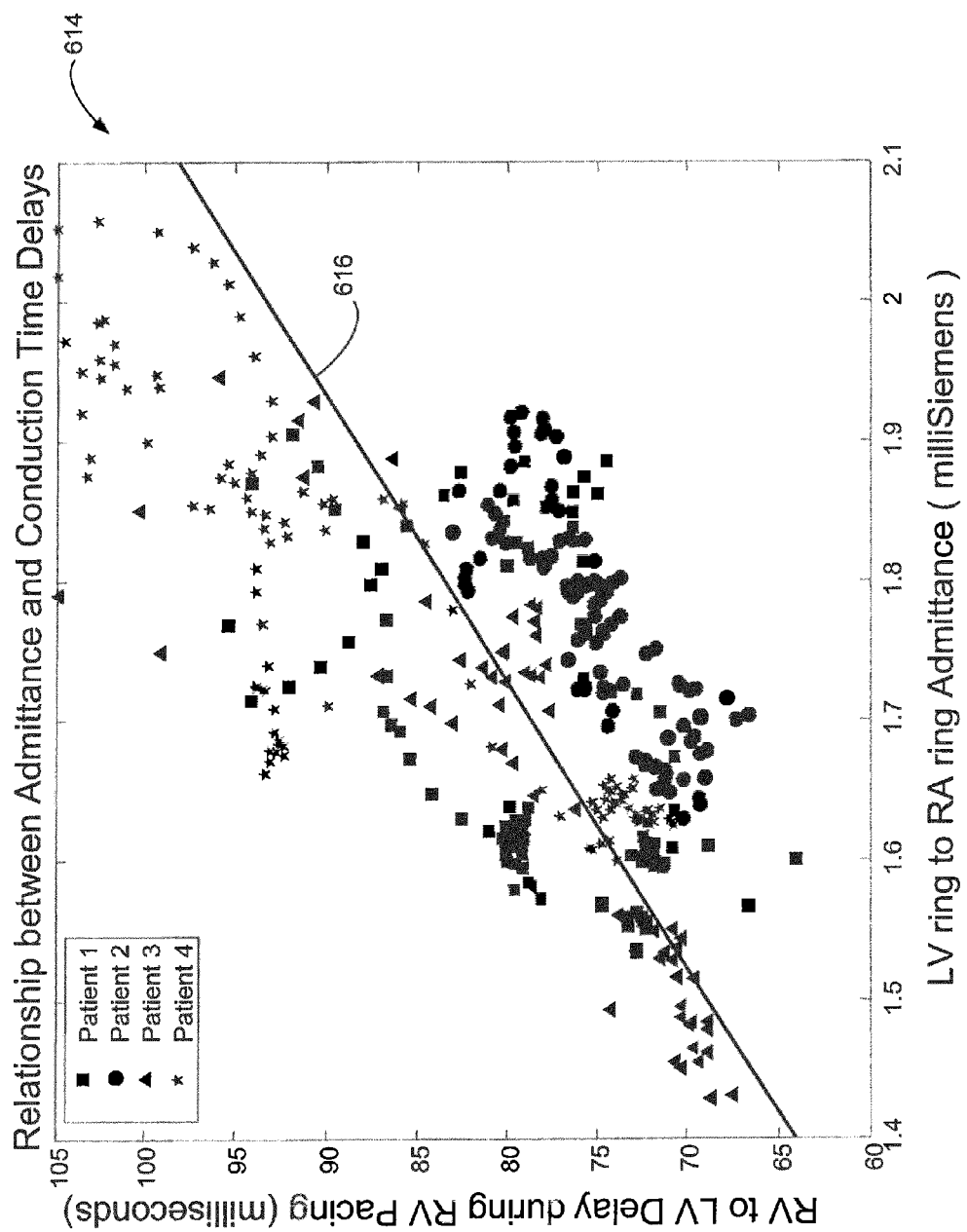
FIG. 18 illustrates a relationship between admittance (i.e. the reciprocal of impedance) and conduction time delays, which is exploited by the technique of FIG. 17.

The estimation of conduction delays based on impedance/admittance exploits a generally linear correlation between admittance and conduction time delays, which is illustrated in FIG. 18 by way of graph 614. In particular, the graph shows the relationship between admittance (1/impedance) and VV delay. This example used the impedance vector from the LV ring to the RA ring. The delay was the between the RV and LV while the RV was being paced. The relationship in this example shows a strong linear relationship between the VV delay and LVring-RAring admittance in five patients. Line 616 represents the best-fit line between VV delay and admittance given by: VVdelay [ms]=48.712*Admittance [mS]−4.12. Hence, there is also strong correlation between the VV delay and LVring-RAring impedance.

Figure 19:
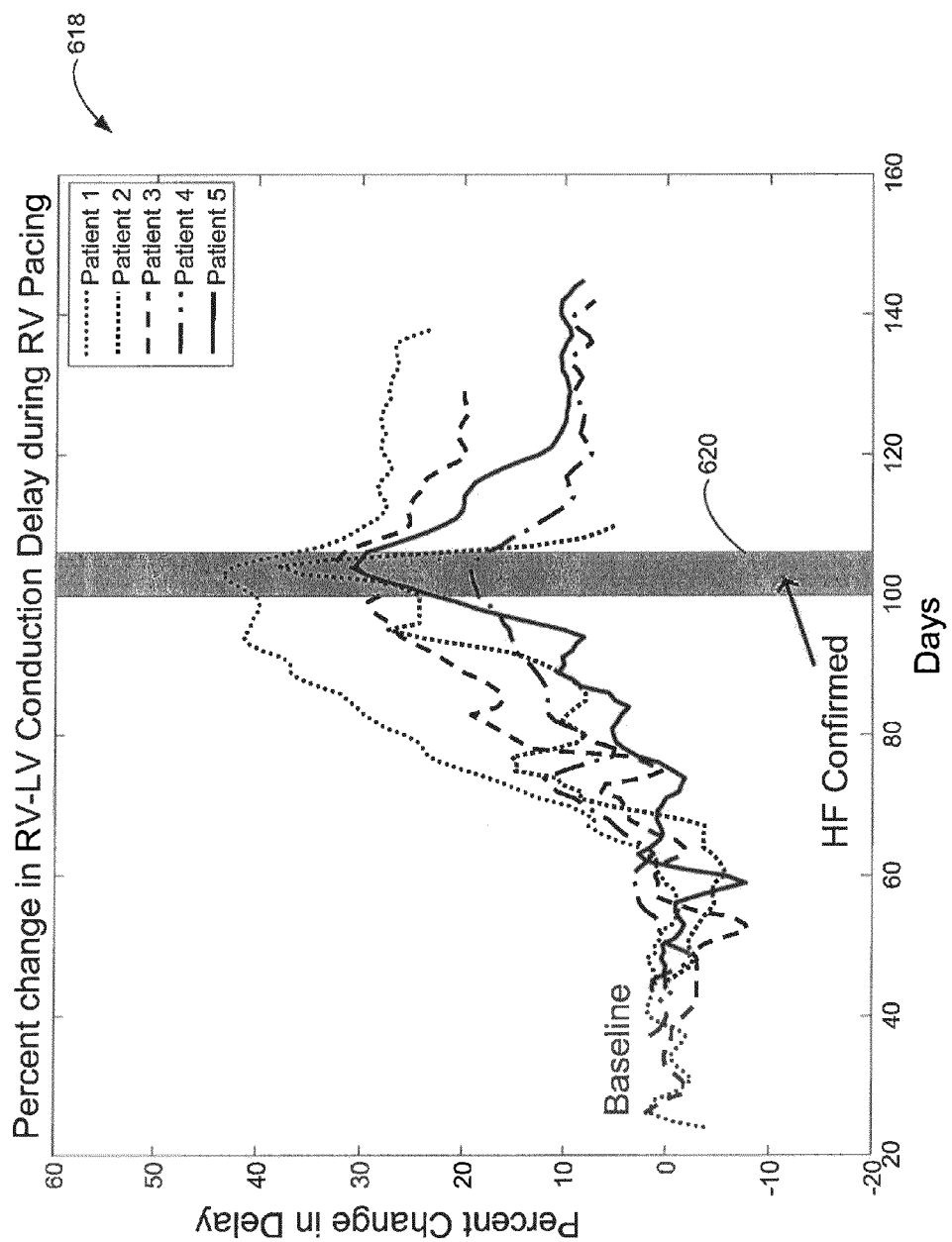
FIG. 19 illustrates changes in conduction time delays that are indicative of heart failure, which may also be exploited by the technique of FIG. 17.

As explained, heart failure can be detected and tracked based on conduction delays. This is illustrated in FIG. 19 by way of graph 618. In this example, developing heart failure caused an increase in the delay between the RV and the LV measured when the RV is paced. Day 100 represents the normalized time when the five patients experienced a HF exacerbation. HF was resolved at day 104 and then patients recovered. The gray shaded area 620 of the graph highlights the time period when heart failure was occurring. Hence, FIG. 19 shows that the delay increased during HF and decreased during recovery. The percent change is referenced to baseline (i.e. zero percent is no HF). The pacer/ICD can be programmed to set a threshold (for instance 20%) to detect HF events. If the percent change in the delays increase above 20%, an alarm can be used to trigger the patient to take corrective action.

Figure 17:
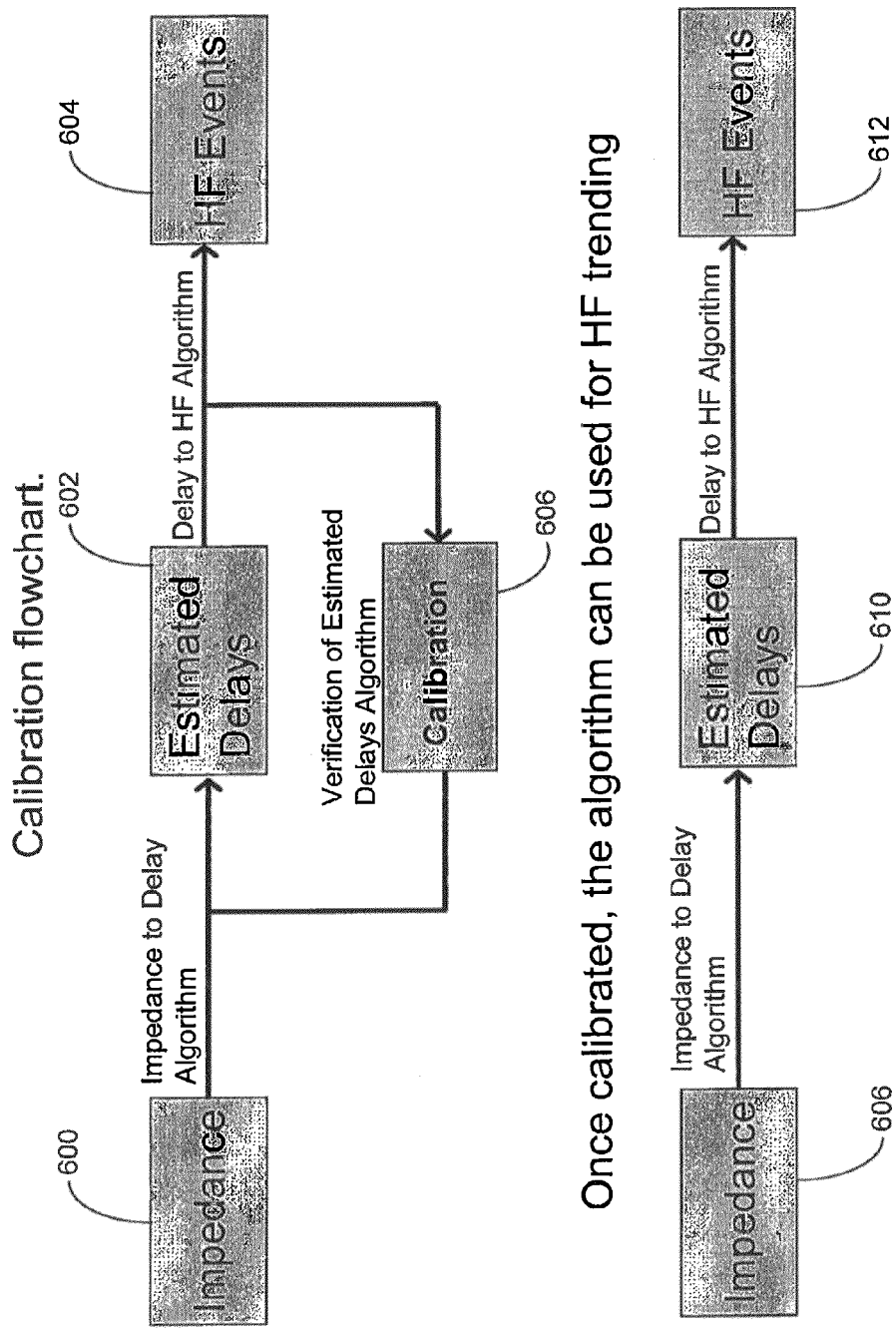
FIG. 17 summarizes a technique for estimating conduction delays based on measured impedance values for use with the system of FIG. 1.
Figure 20:
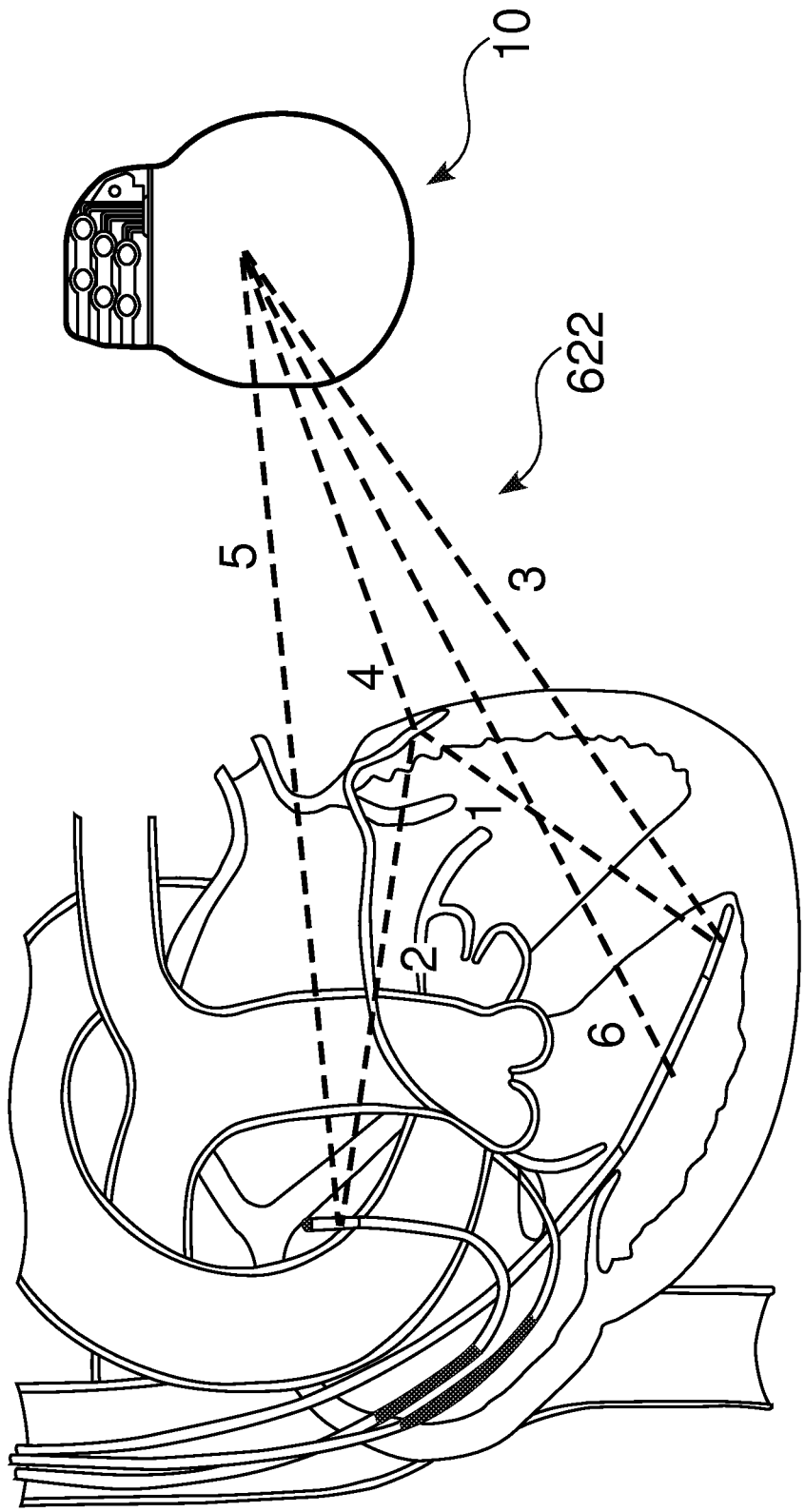
FIG. 20 provides a stylized representation of a heart and particularly illustrates various impedance vectors that may be exploited used to measure impedance for use with the technique of FIG. 17.

As shown in FIG. 20, one or multiple impedance or admittance vectors 622 can be used in either a linear or multi-linear (i.e. quadratic, etc) combination to estimate the conduction delays. The examples of FIG. 20 are as follows: 1: LV ring to RV ring; 2. LV ring to RA ring; 3. RV ring to case; 4. LV ring to case; 5. RA ring to case; and 6. RV coil to case. Multiple different equations can be used to determine the delays. In one example, where admittance values are detected, the relationship between the admittance and delay is quadratic:

$$\text{Delay}=\alpha*\text{adm}^2+\beta*\text{adm}+\delta$$

where "adm" refer to admittance and where alpha, beta, and gamma are known constants developed using a training set of data. Multiple admittance values can be used to determine a delay:

$$\text{Delay}=\alpha_1*\text{adm}_1^2+\beta_1*\text{adm}_1+\alpha_2*\text{adm}_2^2+\beta_2*\text{adm}_2+\delta$$

where admittance vectors 1 and 2 with their corresponding parameters were used to determine the delay. In another embodiment, the estimated delays can be verified each time the patient goes to the physician's office such as with the use of delay algorithm or with special software such as QuickOpt™. When the device is interrogated with the programmer, the programmer would use the QuickOpt procedure to verify the estimated delays offline (FIG. 17).

Admittance/Impedance-Based Estimation Techniques

Figure 21:
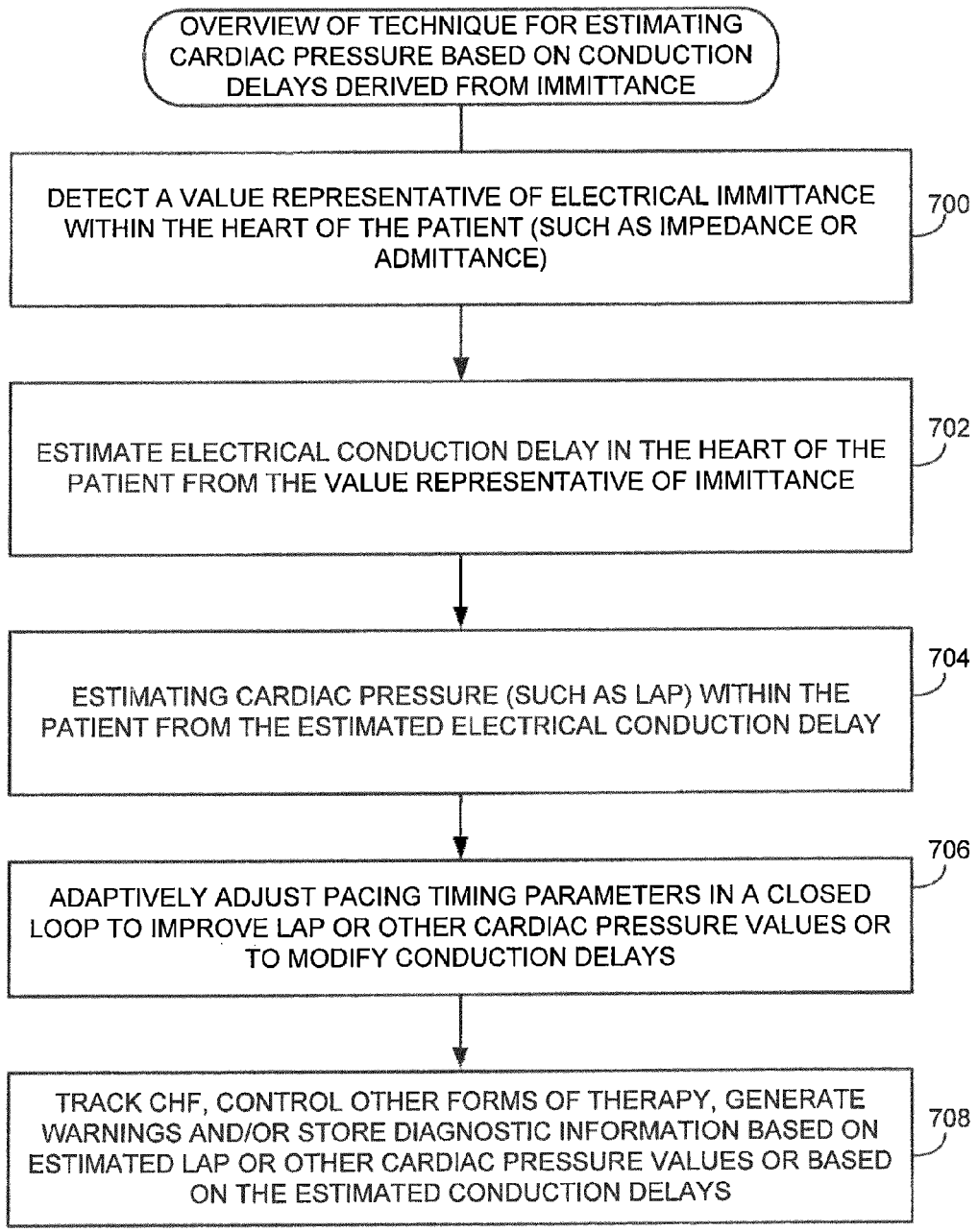
FIG. 21 summarizes a technique for estimating conduction delays based measured immittance values for use with the system of FIG. 1, and for also estimating LAP or other forms of cardiac pressure.

Turning now to FIGS. 21-26, techniques will be described for estimating delay values from admittance/impedance and for further estimating cardiac pressure from estimated delay values. FIG. 21 summarizes the techniques. At step 700, the pacer/ICD detects a value representative of electrical immittance within the heart of the patient (such as impedance or admittance). As noted, admittance is the reciprocal of impedance and, hence, either value can easily be converted to the other. That is, step 700 encompasses the detection of either immittance value and the conversion, where appropriate, to the other immittance value. Alternatively, conductance (G) or other suitable electrical parameters can instead be detected, then used to derive an immittance value. Considering an impedance-based example in more detail, the pacer/ICD detects electrical impedance (Z) along a sensing vector where impedance is known to be correlated with electrical conduction delays, which are in turn correlated with cardiac pressure, particularly LAP. For example, the impedance signal may be sensed between an LV tip electrode and an RA tip electrode. As discussed above, there is a strong correlation between the VV delay and LVring-RAring impedance, which permits VV delay to be estimated from LVring-RAring impedance. There is also a strong correlation between VV delay and LAP, which permits LAP to be estimated from VV delay. As already shown in FIG. 20, multiple impedance signals may be sensed using different sensing vectors passing through different chambers of the heart so as to permit the pacer/ICD to estimate different conduction delays within different chambers of the heart, assuming appropriate conversion values have been determined and calibrated. To this end, the implanted system may be equipped, e.g., with multiple electrodes per lead or with multiple leads per chamber. Unipolar or bipolar sensing systems may be employed.

At step 702, the pacer/ICD estimates an electrical conduction delay in the heart of the patient from the value representative of immittance, such as by applying a first set of pre-determined conversion factors derived using linear regression to convert the immittance values to estimated delay values. Depending upon the vector or vectors originally used to measure immittance at step 700, and the particular conversion factors to be used, any of a variety of electrical conduction delays within the heart can be estimated at step 702. Preferably, though, the pacer/ICD operates to estimate one or more relatively standard conduction delay parameters, such as VV delay or AV delay, as clinicians are familiar with these values. Moreover, a variety of external systems/techniques are available for directly measuring or determining the VV and AV delay values for use in calibrating the estimation procedure of step 702.

Specific exemplary combinations of electrodes are listed below (in Table I) for use in estimating particular delay values. In one example, a linear combination of an "RV coil to case" impedance value, an "LV ring to RA ring" impedance value and an "LV ring to case" impedance value are used to estimate the LV Pacing VV Delay. That is, a predetermined set of conversion factors are used for converting that particular set of impedance values to an estimate of the LV Pacing VV Delay.

QuickOpt or similar systems/techniques can be used to provide an alternative determination of the LV Pacing VV delay to calibrate the conversion factors. Neural networks can also be used to estimate delay based on immittance.

At step 704, in at least some examples, the pacer/ICD then further estimates a parameter representative of cardiac pressure within the patient from the estimated electrical conduction delay, such as by applying a second set of pre-determined conversion factors derived using linear regression to convert the estimated conduction delay to an estimated pressure value. Depending upon the particular delay value or values estimated at step 704, and the particular conversion factors to be used, any of a variety of cardiac pressure values can be estimated at step 704, such as LAP, LVP, LV EDV or LV EDP. Preferably, though, the pacer/ICD operates to estimate LAP, as clinicians are familiar with LAP. Moreover, a variety of systems/techniques are available for directly measuring or determining LAP for use in calibrating the estimation procedure of step 704.

Insofar as the estimation procedure of step 704 is concerned, the various technique techniques described above with reference to FIGS. 1-15 can be used. In an example where the VV delay (i.e. LV-RV delay) is initially estimated from the LVring-RAring impedance, LAP may then be estimated as described above in connection with FIG. 5. As already explained, the duration of the VV conduction delay depends, in part, on the sizes of the chambers of the heart. As heart failure progress, pressure within the LV increases and the LV chamber often becomes distended, resulting in changes in both LVring-RAring immittance and VV conduction delay. Hence, there is, in at least some patients, a correlation between the VV conduction delay (estimated from immittance) and LV chamber size and LV chamber pressure. Hence, in such patients, there is a correlation between LV-RV delay and LV EDV and LV EDP. Likewise, as heart failure progresses, LAP increases. Accordingly, within at least some patients, there is also a correlation between VV delay (estimated from immittance) and LAP. The techniques of the invention exploit this correlation to, e.g., estimate LAP from the VV delay (estimated from immittance). As already noted, LV EDV and LV EDP may also be estimated from the LV-RV delay, and hence LV EDV and LV EDP may also be estimated from LV-RV delays estimated from LVring-RAring impedance or admittance, within at least some patients.

Neural networks can alternatively be used to estimate delay based on immittance. Calibration of the conduction delay-to-cardiac pressure estimation procedure of step 704 may be performed generally in accordance with the techniques described above in connection with FIGS. 8-13.

At step 706, the pacer/ICD then adaptively adjusts pacing timing parameters in a closed loop to improve LAP or other cardiac pressure values or to modify conduction delays. Techniques described above with reference to FIG. 7 can be used. At step 708, the pacer/ICD then tracks CHF, controls other forms of therapy, generates warnings and/or stores diagnostic information based on estimated LAP or other cardiac pressure values or based on the estimated conduction delays. Techniques described above with reference to FIG. 3 can be used.

Note that the functions of steps 706 and 708 may be performed based on either the conduction delays estimated at step 702 or on the cardiac pressure values estimated at step 704, or some combination thereof. For example, estimated conduction delays may be used to adjust pacing timing parameters at step 706. As another example, estimated conduction delays may be used to track CHF at step 708.

Impedance-Based LAP Estimation Example

Figure 22:
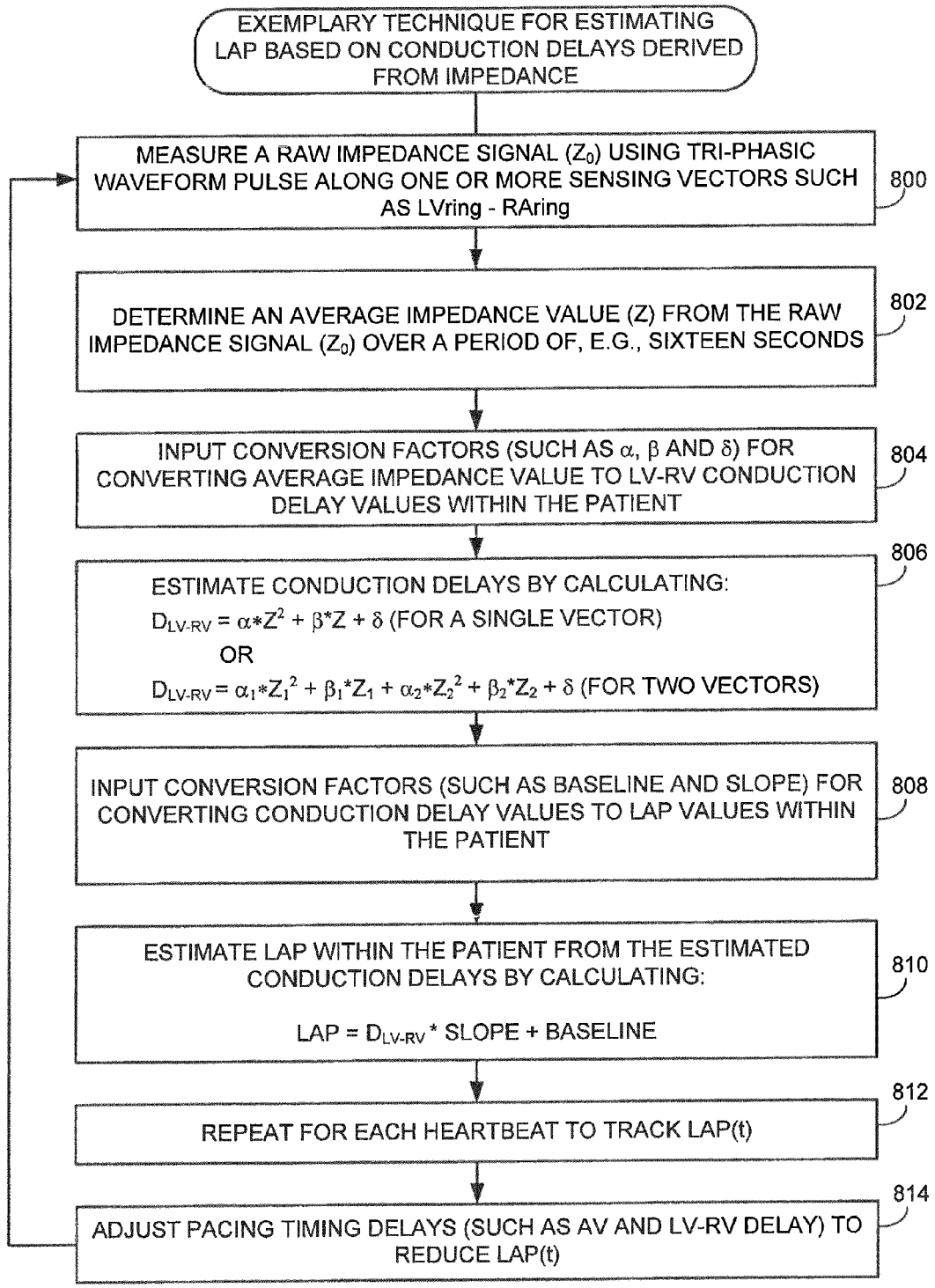
FIG. 22 illustrates a first exemplary technique for estimating LAP based on conduction delays, wherein the delays are estimated from measured impedance values, in accordance with the general technique of FIG. 21.

Turning now to FIG. 22, an example is illustrated where average impedance (Z) is used to estimate LAP by first estimating the VV (i.e. LV RV) conduction delay. At step 800, the pacer/ICD measures a raw impedance signal ($Z_0$) along one or more sensing vectors, such as those listed below in TABLE I. In general, impedance signals can be obtained by transmitting a current between a pair of electrodes and subsequently measuring the voltage between the same or another pair of electrodes. The impedance is calculated as the ratio of the measured voltage to the transmitted current. Preferably, a tri-phasic impedance pulse waveform is employed to sense the impedance signal. The tri-phasic waveform is a frequency-rich, low energy waveform that provides a net-zero charge and a net-zero voltage. An exemplary tri-phasic pulse waveform is described in detail in some of the patent applications, cited above, particularly U.S. patent application Ser. No. 11/558,194, by Panescu et al., entitled "Closed-Loop Adaptive Adjustment of Pacing Therapy based on Cardiogenic Impedance Signals Detected by an Implantable Medical Device." For convenience, a portion of that description will now be provided herein.

The tri-phasic waveform possesses many special waveform features and electrical characteristics that are well suited for probing and measuring many types of physiological parameters in the body using current modulated or voltage modulated pulses. The waveform has negative phases (pulse segments below baseline) that balance positive phases (pulse segments above baseline). Other versions of the waveform may have more than three phases, may be synchronous or asynchronous, may be rectangular or sinusoidal, etc. One version of the waveform uses the sinc(x) sampling waveform. Typically, the tri-phasic waveform is applied as a current waveform with the resulting voltage being sensed. Alternatively, the waveform is applied as a voltage waveform and sensed as electrical current. In the following descriptions, a current waveform is assumed, unless otherwise noted.

Advantageous properties of the waveform include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces. The waveform preferably has a total duration less than the charging time constant of the electrode-electrolyte interfaces used to inject and sense the signals. These time constants are typically in the range of a few milliseconds. In one implementation, the duration of the waveform is less than one millisecond. This waveform feature is helpful for minimizing polarization effects at these electrode-electrolyte interfaces. Other features of the waveform include symmetric or asymmetric phase duration, decreasing phase amplitudes, and alternating phase signs. The waveform preferably has null durations in between phases to provide time to allow complete processing of information caused by one phase before the next phase of the waveform begins. Implementations of the waveform that have near perfect square wave pulses (or rectangular wave pulses) contain a great deal of high-frequency content. Near-sinusoidal implementations of the waveform may contain less high frequency content than the rectangular wave versions.

The features of exemplary waveforms just enumerated provide numerous advantages, including: eliminating the need for fast digital sampling, minimizing artifacts introduced in the measurement process, increased tolerance of small phase delays between injected and sensed signals. The waveform also lends itself to CMOS realization using low-value switched capacitor solutions. Further, the wide frequency spectrum of the injected signal can be used to implement algorithms that differentiate tissues based on their frequency response, and/or phase delay. The very low duty-cycle of the waveform makes them safer for patients. The reduced duty-cycle brings the injected charge and the root-mean-square value of the injected signal well below levels that could be perceived by the patient or that could induce adverse events.

It is important to note that the net-zero voltage feature, also referred to as the voltage-balanced feature, refers to the voltage formed on blocking capacitors that appear in series with the load. The flow of current through these capacitors builds up voltage across them. Since these capacitors also appear in circuits that are responsible for sensing cardiac activity, it is important that the net voltage built up on them be zero. As a result of the net-zero voltage feature, the influence of the waveform on the circuits that sense cardiac activity is minimal. Other features of the waveform derive from the above-mentioned null segments—intra-waveform segments containing no signal—that serve several purposes. First, the null segments allow the electronics in processing circuits to settle during measurement of phases and second, they allow multiple instances of the waveform to exist in the patient's tissue simultaneously, being staggered by time multiplexing such that a phase of one waveform can be measured during the time that there is no signal between phases of another waveform.

The waveform provides an elegant and reliable vehicle for measuring bodily impedances in a manner that gives reliably reproducible results. Instead of a conventional technique of trying to sense an instantaneous "snapshot" measurement of a conventionally injected signal, the circuitry of the pacer/ICD derives an impedance measurement by dividing the area under the sensed voltage curve by the area of the injected current waveform. The pacer/ICD can perform this exemplary method by "integrating the curve" of an absolute value of the waveforms. Sometimes the exemplary implantable device can closely approximate this integration without having to perform an integration operation by directly measuring and summing the area "under" the curve (e.g., under the rectangular wave) of the sensed voltage waveform, that is, the area composed of the absolute value of the three areas of the three phases of an exemplary tri-phasic current waveform.

Likewise, the pacer/ICD can integrate, or closely approximate the integration, by measuring and summing the area "under" the curve (e.g., the rectangular wave) of the sensed voltage waveform, that is, the area composed of the absolute value of the three areas of the three phases. In one implementation, the area of the sensed voltage waveform is measured at the output of an integrator circuit. The area of the injected current waveform is computed by, or preset by, the microcontroller driving the implantable device. The pacer/ICD may thus use this area-based ("areal") approach to deriving a network of impedance measurements over a multi-vector network.

Although the tri-phasic pulse is preferred, other impedance detection pulses or techniques can be used. Depending upon the particular sensing vector, it may be appropriate to filter the resulting impedance signal to eliminate or reduce any non-cardiogenic components such as any components arising due to respiration or changes in body position of posture. Band-pass filtering is typically sufficient to filter out respiratory components.

At step 802, the pacer/ICD then determines an average impedance value (Z) from the raw impedance signal ($Z_0$) over a period of, e.g. sixteen seconds, which is typically equivalent to about four respiratory cycles. Preferably, an impedance detection circuit is provided within the pacer/ICD that is equipped to determine the average value (Z) of the raw impedance signal, or the average of various parameters derived from the raw impedance signal such as average peak-to-peak impedance or average systolic slope. Systolic slope represents the slope of the cardiogenic component of the impedance signal, i.e. that portion of the signal representative of the beating of the heart of the patient. In one example, the maximum of the systolic slope may be exploited, i.e. the maximum of dZ/dt may be calculated for each "cardiogenic" beat within the impedance signal, with the max dZ/dt values then averaged over some interval of time, such as sixteen seconds. In any case, by averaging the raw impedance signal (or parameters derived therefrom) over several respiratory cycles, variations due to respiration and the beating of the heart are substantially filtered out. Particular techniques for detecting or determining the various components of the initial raw impedance signal are discussed in the above-cited applications, including techniques for identifying or extracting the cardiogenic component.

At step 804, the pacer/ICD inputs predetermined conversion factors from memory for converting the cardiogenic electrical impedance values to LV-RV conduction delay estimates (or other conduction delay estimates). The conversion factors may be, e.g., the aforementioned $\alpha$, $\beta$ and $\delta$ conversion factors originally discussed above in connection with FIG. 17, obtained during a calibration procedure employing linear regression. At step 806, the pacer/ICD then estimates LV-RV (i.e. VV) conduction delays by calculating:

$$D_{LV-RV} = \alpha * Z^2 + \beta * Z + \delta$$

for a single vector where $\alpha$, $\beta$ and $\delta$ are pre-determined conversion factors input at step 802 and wherein Z represents the average impedance along a single vector passing through the LV and RV such as from LVring to RAring.

In an example where two sensing vectors are instead employed, the conduction delays are estimated by calculating:

$$D_{LV-RV} = \alpha_1 Z_1^2 + \beta_1 * Z_1 + \alpha_2 * Z_2^2 + \beta_2 * Z_2 + \delta$$

where $\alpha_1$, $\beta_1$, $\alpha_2$, $\beta_2$ and $\delta$ are the conversion factors and wherein $Z_1$ represents the average impedance along a first vector passing through the LV and RV such as from LVring to RAring and $Z_2$ represents the average impedance along a second, different vector passing through the LV and RV such as from RVring to LAring. In some implementations, three or more sensing vectors are instead used.

In one particular example, three impedance values are derived from various combinations of electrodes for use in estimating particular AV and VV delays as follows:

TABLE I

AV-VV Delay Models

| Delay | Impedance 1 | Impedance 2 | Impedance 3 |
|---|---|---|---|
| LV Pacing VV Delay | RV coil to case | LV ring to RA ring | LV ring to case |
| RV Pacing VV Delay | RV coil to case | LV ring to case | RA ring to case |
| No Pacing VV Delay | LV ring to RA ring | RV ring to LV ring | LV ring to case |
| RA Pacing A-RV Delay | RV Coil to case | LV ring to RA ring | LV ring to case |
| RA Pacing A-LV Delay | RV coil to case | LV ring to RA ring | LV ring to case |
| RA Pacing VV Delay | LV ring to RA ring | RV ring to LV ring | RA ring to case |
| No Pacing A-RV Delay | LV ring to RA ring | LV ring to case | RA ring to case |
| No Pacing A-LV Delay | RV coil to case | RA ring to case | RV ring to case |

A linear combination of the three impedances may be used to calculate the corresponding delay value. For example, a linear combination of the "RV coil to case" impedance value, the "LV ring to RA ring" impedance value and the "LV ring to case" impedance value may be used to estimate the LV Pacing VV Delay, using predetermined conversion factors appropriate for estimating that particular delay value from those particular impedance values.

At step 808, the pacer/ICD then inputs conversion factors for converting conduction delay values to LAP values within the patient. The conversion factors may be, e.g., predetermined slope and baseline values obtained during a calibration procedure employing linear regression. General techniques for determining and updating slope and baseline values are discussed above in connection with FIGS. 8-13. Note, though, that the specific slope and baseline values may differ when using the technique of FIG. 22 as compared to the techniques of FIGS. 1-15 because the slope and baseline values for use with FIG. 22 must be appropriate for use with estimated delay values rather than measured delay values. Moreover, different conversion factors are typically required at step 808 depending upon the particular vector used to derive the impedance signal from which the conduction delay is estimated.

At step 810, the pacer/ICD estimates LAP within the patient from the estimated conduction delays by calculating:

$$LAP = D_{LV\text{-}RV} * SLOPE + BASELINE.$$

As indicated by step 812, the pacer/ICD repeats the estimation procedure for each heartbeat to track LAP(t). At step 814, the pacer/ICD adjusts its timing delays (such as the VV and AV delays) in an effort reduce LAP so as to mitigate CHF or other heart ailments. Adjustment techniques already described above in connection with FIGS. 5 and 7 may be used.

Admittance-Based LAP Estimation Example

Figure 23:
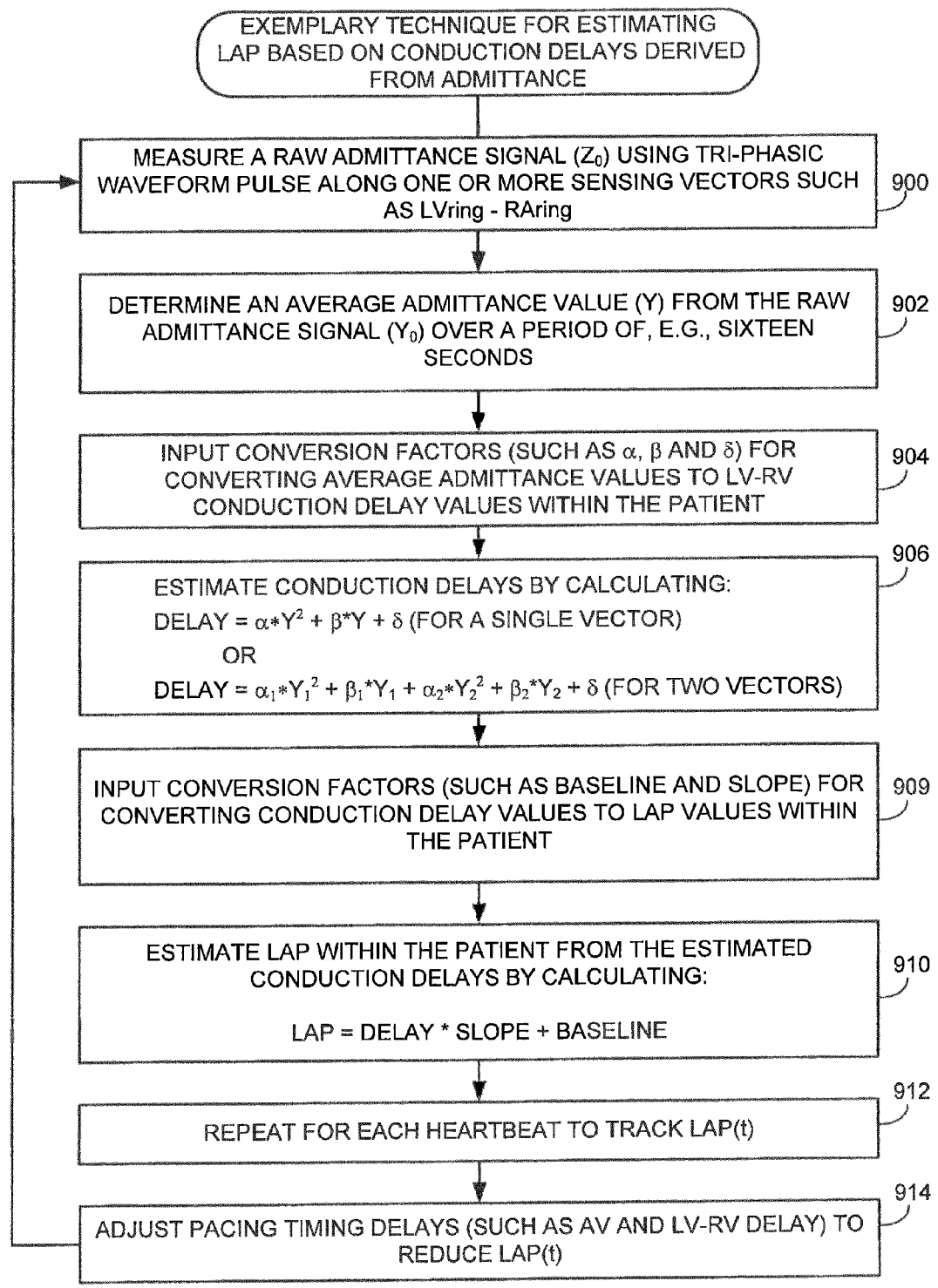
FIG. 23 illustrates a second exemplary technique for estimating LAP based on conduction delays, wherein the delays are estimated from measured admittance values, in accordance with the general technique of FIG. 21.

FIG. 23 provides an example where average admittance (Y) is instead exploited. The steps of FIG. 23 are similar to those of FIG. 22 and will be discussed only briefly. At step 900, the pacer/ICD measures a raw admittance signal ($Y_0$) and, at step, 902, determines an average admittance value (Y) from the raw admittance signal ($Y_0$) over a period of, e.g. sixteen seconds. In some examples, various parameters derived from the raw admittance signal may instead be exploited, such as average peak-to-peak admittance. At step 904, the pacer/ICD inputs predetermined conversion factors from memory for converting the average admittance values to LV-RV conduction delay estimates (or other conduction delay estimates). The conversion factors may be, e.g., similar to the aforementioned □□, □ and □□ conversion factors discussed above in connection with FIG. 22, but appropriate for use with admittance rather than impedance.

At step 906, the pacer/ICD then estimates LV-RV (i.e. VV) conduction delays by calculating:

$$D_{LV\text{-}RV} = \alpha * Y^2 + \beta * Y + \delta$$

for a single vector where $\alpha$, $\beta$ and $\delta$ are the conversion factors appropriate for use with admittance and wherein Y represents the average admittance along a single vector passing through the LV and RV, such as from LVring to RAring.

In an example where two sensing vectors are instead employed, the conduction delays are estimated by calculating:

$$D_{LV\text{-}RV} = \alpha_1 * Y_1^2 + \beta_1 * Y_1 + \alpha_2 * Y_2^2 + \beta_2 * Y_2 + \delta$$

where $\alpha_1$, $\beta_1$, $\alpha_2$, $\beta_2$ and $\delta$ are the appropriate conversion factors and wherein $Y_1$ represents the average admittance along a first vector passing through the LV and RV such as from LVring to RAring and $Y_2$ represents the average admittance along a second, different vector passing through the LV and RV such as from RVring to LAring.

At step 908, the pacer/ICD then inputs conversion factors for converting conduction delay values to LAP values within the patient. The conversion factors may again be, e.g., predetermined slope and baseline values obtained during a calibration procedure employing linear regression. At step 910, the pacer/ICD estimates LAP within the patient from the estimated conduction delays by again calculating:

$$LAP = D_{LV\text{-}RV} * SLOPE + BASELINE.$$

Also, as indicated by step 912, the pacer/ICD can repeat the estimation procedure for each heartbeat to track LAP(t) and, at step 914, the pacer/ICD can adjust its timing delays in an effort reduce LAP.

Hence, FIGS. 22-23 illustrate exemplary techniques for estimated LAP based on conduction delay values estimated from impedance/admittance values. These techniques may be used in addition to, or as an alternative to, the LAP estimation techniques of FIGS. 1-15, which are instead based on measured conduction delays values. In some implementations, the pacer/ICD is equipped to perform both estimation techniques and so the memory of the pacer/ICD stores the various conversion factors and retrieves the appropriate factors depending upon the particular estimation technique currently being used, as specified by the programming of the device. LAP values estimated using different techniques may be averaged together.

Admittance/Impedance-Based Delay Estimation Calibration

Figure 24:
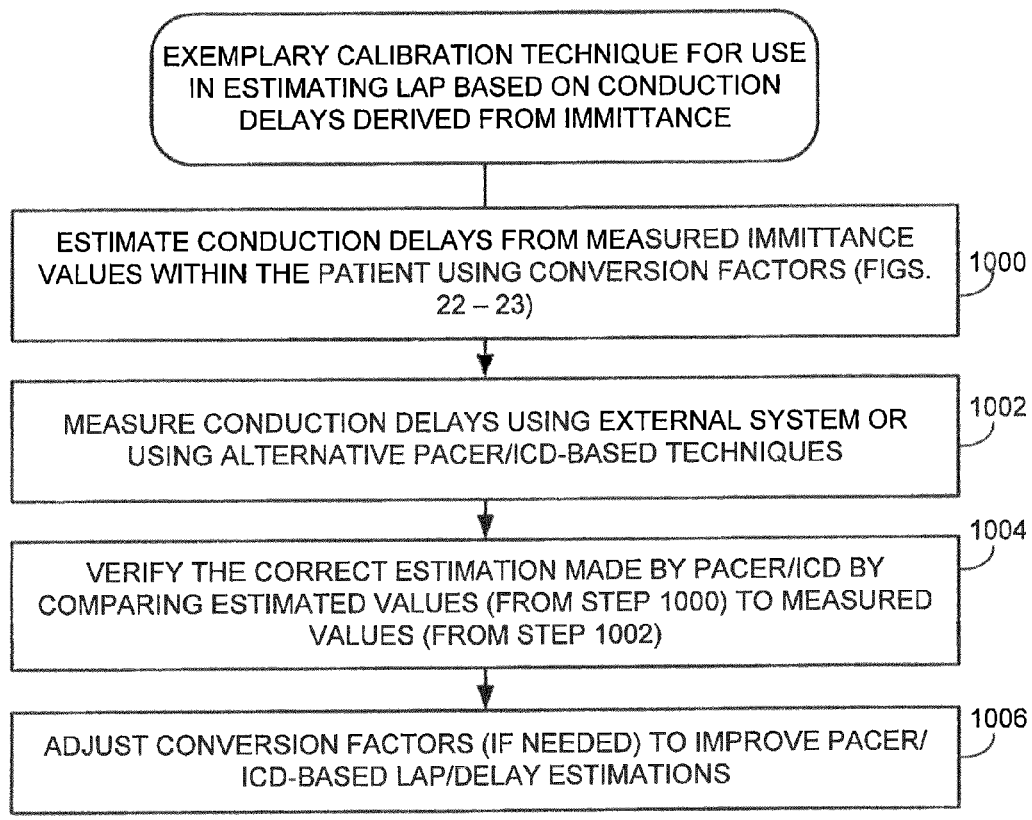
FIG. 24 summarizes a calibration technique for calibrating the LAP estimation techniques of FIGS. 22-23.

FIG. 24 illustrates an exemplary technique for calibrating the immittance-to-delay estimation procedures of FIGS. 22-23. At step 1000, the pacer/ICD estimates conduction delays (such as LV-RV delays) from measured immittance values within the patient using various conversion factors (FIGS. 22-23). At step 1002, an external system, such as a device programmer, measures the same conduction delays for use in calibration. For example, if the external device is equipped with the QuickOpt system, data generated by QuickOpt can be used to specify the LV-RV conduction delay within the patient for comparison against an LV-RV delay estimated by the pacer/ICD. For the sake of completeness, pertinent portions of the QuickOpt code have been provided in the attached appendix (Appendix A). The example of Appendix A primarily operates to set RV thresholds. However, the LV-RV delay may be obtained using information generated by the code. That is, in the code. "ndx_lv" is the location of the LV QRS. "ndx_rv" is the location of the RV QRS. Hence, the LV-RV delay may be obtained by subtracting ndx_rv from ndx_lv (or vice versa).

At step 1004, the external system verifies the correct estimation made by the pacer/ICD by comparing the estimated values from step 1000 to the measured values from step 1002. At step 1006, the external system adjusts the conversion factors (if needed) of the pacer/ICD to improve pacer/ICD-based LAP/delay estimations. In this regard, the external system may transmit programming commands to the pacer/ICD to reprogram it with adjusted conversion factors. By improving or calibrating the conversion factors, the pacer/ICD can more accurately estimate conduction delays, which in turn allows the device to more accurately estimate LAP. As already explained in connection with FIG. 16, the external programmer can also be equipped with systems for re-calibrating the conduction delay-to-LAP estimation procedures employed by the pacer/ICD. Preferably, both stages of the overall LAP estimation procedure employed by the pacer/ICD are periodically recalibrated.

Note also that if the pacer/ICD itself is equipped to reliably measure conduction delays, then those measured delays can additionally or alternatively be used to periodically recalibrate the immittance-to-delay estimation procedure (or vice versa). Also, at least some pacer/ICDs are equipped with a device-based QuickOpt system to allow conduction delays to be readily obtained within the device. These conduction delay values can also be used calibrate the immittance-to-delay estimation procedure. U.S. Pat. No. 7,248,925, to Bruhns et al., entitled "System and Method for Determining Optimal Atrioventricular Delay based on Intrinsic Conduction Delays."

For the sake of completeness, devices equipped to implement the techniques of FIGS. 21-24 will now be briefly described.

Exemplary Pacer/ICD and External Programmer

Figure 25:
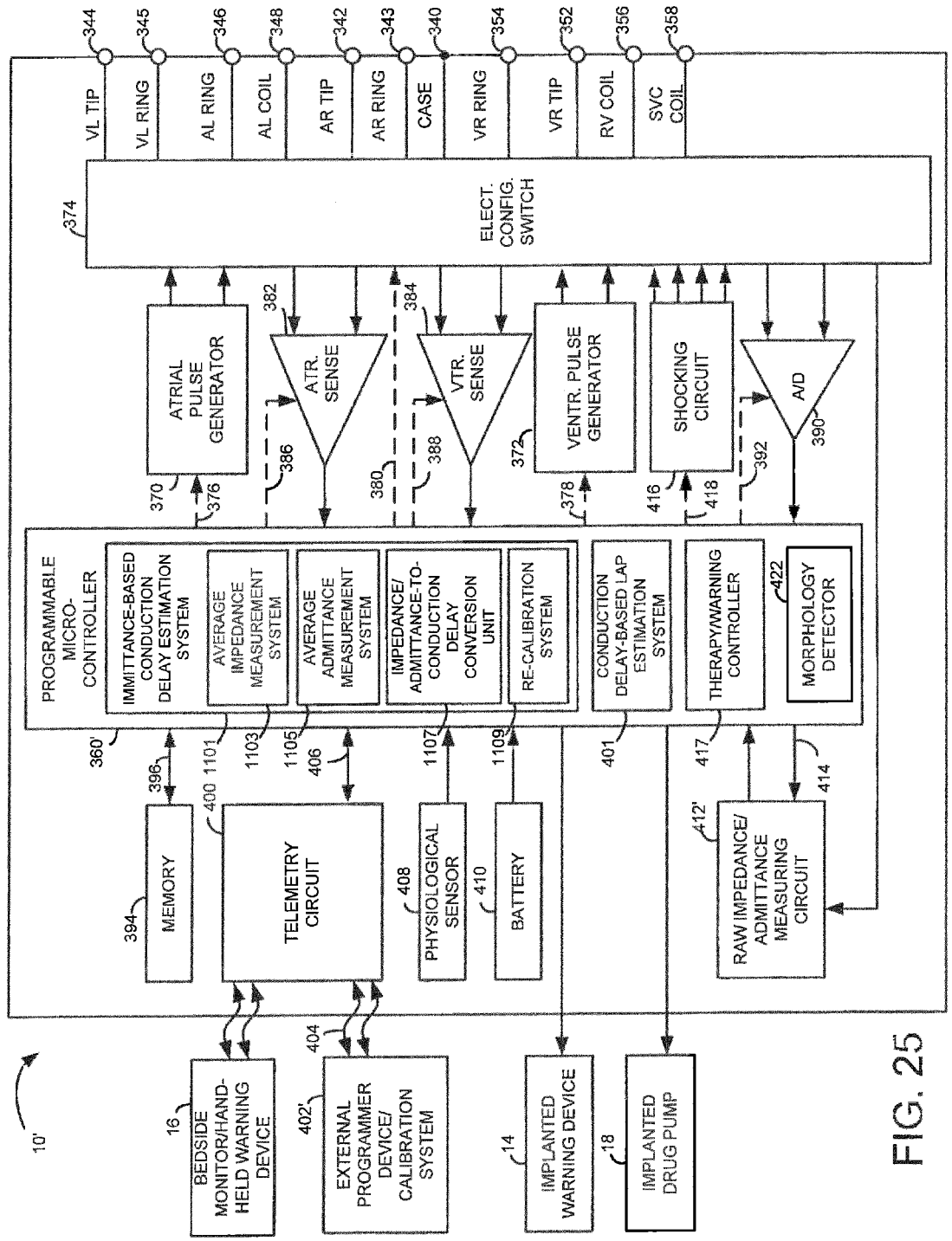
FIG. 25 illustrates a functional block diagram of an alternative implementation of the pacer/ICD of FIG. 14, particularly illustrating components for estimating conduction delays based on immittance values, for estimating LAP from the conduction delays, and for adaptively adjusting pacing parameters in response thereto.

A simplified block diagram of internal components of a pacer/ICD 10' is provided in FIG. 25, wherein the pacer/ICD includes components for estimating LAP based on delays values estimated from immittance. Most of the components are the same as in pacer/ICD 10 of FIG. 15 and only pertinent differences will be noted. The pacer/ICD 10 includes an impedance/admittance measuring circuit 412' for measuring or detecting an immittance value. Insofar as immittance-based delay estimation is concerned, the microcontroller 360' includes an immittance-based conduction delay-based estimation system 1101 operative to estimate conduction delays based on immittance values using the techniques described above in FIGS. 21-24. Estimation system 1101 includes an average impedance measurement system 1103 and additionally, or alternatively, includes an average admittance measurement system 1105. Estimation system 1101 also includes an impedance/admittance-to-conduction delay conversion unit 1107 operative to convert impedance/admittance values to conduction delays using, e.g., conversion factors, as already described. An on-board re-calibration system 1109 may be provided for calibrating the conversion factors used to convert impedance/admittance to conduction delays, if the device is equipped to reliably measure (or otherwise obtain) conduction delays.

The microcontroller also includes, as in the embodiment of FIG. 15, a conduction delay-based LAP estimation system 401 operative to estimate cardiac pressure from electrical conduction delays (in this case estimated delays rather than measured delays.) Although not shown, an LAP-based CHF detection system (such as system 415 of FIG. 15) may also be provided to detect and track CHF based on LAP. Warning and/or notification signals are generated, when appropriate, by a therapy/warning controller 417 then relayed to the bedside monitor 18 via telemetry system 400 or to external programmer 402 (or other external calibration system.) Controller 417 can also control an implantable drug pump, if one is provided, to deliver appropriate medications. Controller 417 also controls the adaptive adjustment of CRT parameters and other pacing parameters, as discussed above. Terminals for connecting the implanted warning device and the implanted drug pump to the pacer/ICD are not separately shown. Diagnostic data pertaining to estimated conduction delays, LAP, CHF, therapy adjustments, etc., is stored in memory 394.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Figure 26:
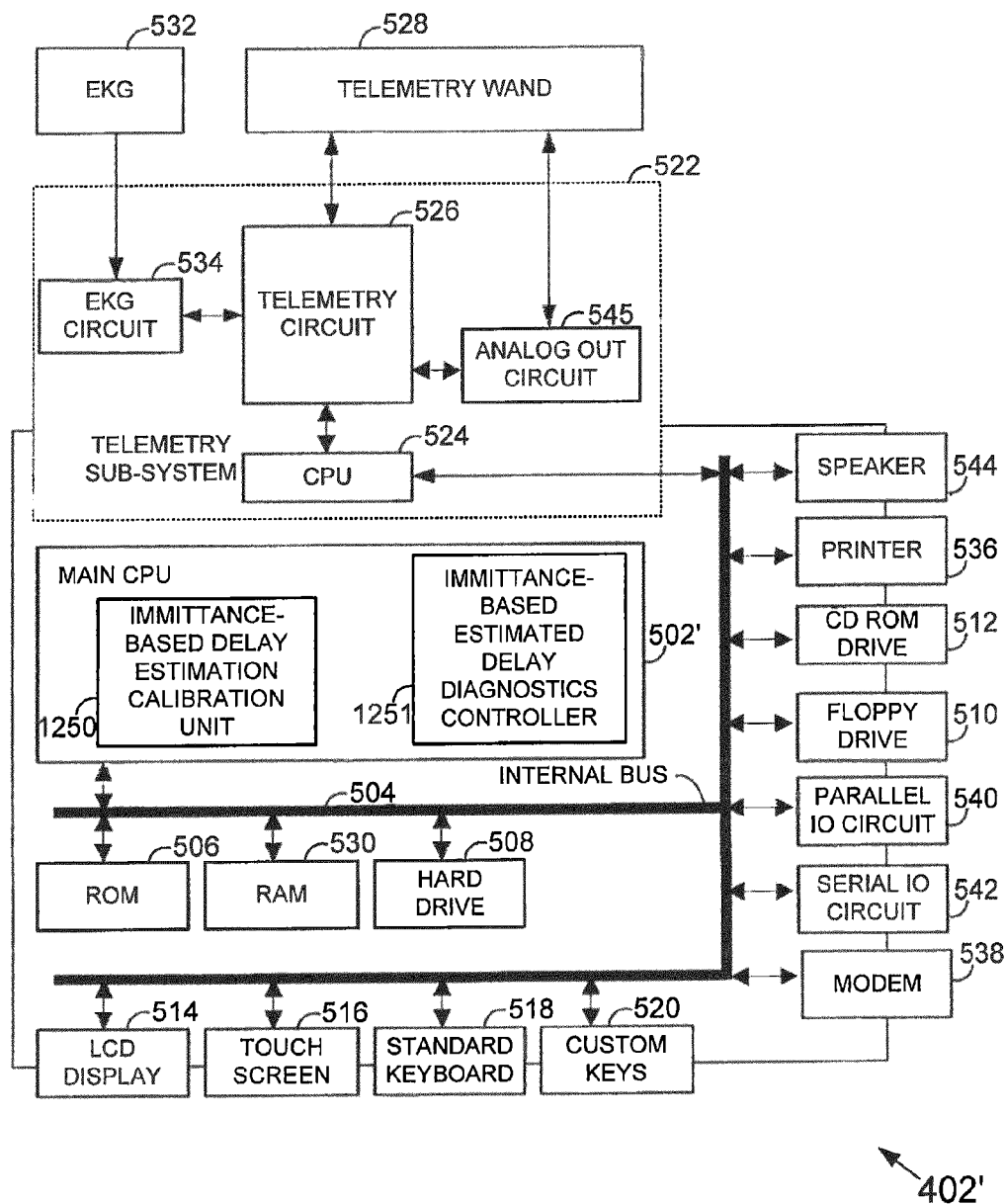
FIG. 26 is a functional block diagram illustrating components of a device programmer of FIG. 25, and in particular illustrating an immittance-based calibration system.

FIG. 26 illustrates pertinent components of an external programmer 402' for use in programming the pacer/ICD of FIG. 26 and for performing the above-described calibration techniques. Most of the components are the same as in programmer 402 of FIG. 16 and only pertinent differences will be noted. CPU 502' includes, in this example, an immittance-based delay estimation calibration unit 1250 operative to perform the calibration procedures described above for calibrating the immittance-to-delay conversion performed by the pacer/ICD of FIG. 25. CPU 502' also preferably includes an immittance delay-based estimated delay diagnostics controller 1251 operative to control the display of estimated delay values and related diagnostics. Although not shown in FIG. 26, the programmer device may also include the LAP estimation calibration and diagnostics components of the programmer of FIG. 16.

Using Intra-Cardiac Conduction Time Delays to Predict/Trend Heart Failure

Still further, the pacer/ICD may be equipped to predict heart failure events and to trend heart failure progression. In this regard, during HF, the myocardium of the heart remodels such that the cardiac output decreases. During the remodeling, intracardiac conduction time delays have been shown to change. By monitoring the changes in conduction delays, the pacer/ICD can monitor HF progression and detect the occurrence of HF events.

More specifically, patients with heart failure may be candidates for a CRT device. A heart failure patient with an implantable CRT device has at least three pacing leads implanted therein (RA, RV, and LV). Each of these leads may be used to stimulate the heart to contract either independently or synchronously. When a single chamber is stimulated, cardiac contraction occurs in the stimulated chamber, which is usually followed by a subsequent cardiac contraction in other chambers after the stimulus has had sufficient time to reach the other chamber. The time delay between contractions of any two chambers is dependent on various factors, such as conduction velocity and the distance to be traveled. It is believed that the time delay between the contraction of any two cardiac chambers following either a natural occurring stimulus or an externally administered stimulus is indicative of the degree of cardiac failure and is also proportional to the cardiac chamber size (as explained above), such that longer delays may be associated with a worsening cardiac status. Hence, one or a combination of conduction delays can be used to predict HF events and trend HF progression.

The inter-ventricular conduction time delay following the delivery of a left ventricular pacing stimulus may be used to estimate the size and/or LV filling pressure. At the time a pacing stimulus is delivered to the LV, the chamber is filled with blood and corresponds to LV EDV. The pacing stimulus causes the LV muscle to depolarize and subsequently contract. While the LV depolarization occurs, the depolarization wave front travels across the LV toward the right ventricle and ultimately causes the RV to depolarize and subsequently contract. The delay between the time when the LV pacing stimulus was administered and the time when the RV depolarizes may be proportional in at least some patients to the LV EDV. For HF, the LV EDV increases as HF progresses, thus the LV to RV conduction time delay will increase as HF worsens, in at least some patients. The pacing stimulus could also be applied to the RV ventricular while measuring the time delay until the LV depolarizes. Other delays that might be used are the paced atrium to recorded ventricles (both RV and LV), intrinsic activity either between the atrium and the ventricles or between the right and left ventricles.

The conduction time delay can be used in a variety of ways to trend HF progression and to detect HF events. In one embodiment, to trend HF progression is to measure the change in time delay from baseline. The baseline is set to when the patient does not experience any HF events. If the change in time delay increases. HF is thus getting worse. A decrease in time delay in indicative of an improvement in HF. The change in time delay can be represented in time (i.e. milliseconds) or as a percent change from baseline:

$$PercentChange = \frac{CurrentMeasurement - Baseline}{Baseline} * 100\%$$

By using the change in time delays (either as a percent or in milliseconds), the pacer/ICD can set a threshold to detect HF events. For example, if the time delay increases more than 20% over baseline, an alarm would be triggered to notify the patient to change medication or seek medical attention.

In another embodiment, the threshold to detect HF events is instead based on the previous values of the delays. If the patient were slowly worsening, the threshold for an HF event would be slowly increasing. This method allows the natural progression of HF to occur without triggering false alarms. However, if a sudden change were detected in time delays, such as a HF exacerbation, the time delay would increase above the threshold and trigger the alarm.

Another trending algorithm is:

$$r = 1 - \frac{Delay_{LongTerm}}{Delay_{ShortTerm}}$$

HF_Index = sum(max($r$, 0))

where the long-term delay is a 10 to 50 day moving average of the delays, and the short-term delay is a 1 to 9 day moving average of the delays. During a HF event, the short-term delay is larger than the long-term delay, causing r to be positive. Since HF_Index is a cumulative sum, a positive value of r causes the HF_Index to increase. An HF event causes the HF_Index rise, and if stays above a threshold for a certain number of days, an alarm is triggered. If r is not positive for a certain number of days (for instance, 3 days), HF_index is reset to zero.

Other cumulative sum algorithms that incorporate comparing long-term delays (10 to 50 days) to short-term delays (1-9 days) may also be used. Any combination of delays might also be used in these detection algorithms (for instance, RV pacing RV-LV delay and Intrinsic RA-RV delay). To determine the delays, the pacer/ICD can use a variety of methods. One such method uses a built-in delay algorithm. In one example, the set of measured delays is:

Paced LV RV to LV Delay
Paced RV RV to LV Delay
Paced RA RA to RV Delay
Paced RA RA to LV Delay
Paced RA RV to LV Delay
No Pacing RA to RV Delay
No Pacing RA to LV Delay
No Pacing RV to LV Delay Any one delay or any combination of the delays can be used by the pacer/ICD for HF trending/predicting. The techniques described above can be used to estimate these or other delays for HF trending/predicting, as well as for use in estimating LAP, as already described.

Hence, a pacer/ICD or external system can be equipped: to use the intracardiac conduction time delays to trend HF progression and to detect HF events; to use a cumulative sum algorithm to trend HF and to detect HF events; to use a threshold algorithm to trend HF and to detect HF event; to use QuickOpt (or similar) to determine the conduction delays; to use different impedance vectors to determine conduction delays; and/or to use QuickOpt to verify an estimate conduction delays In general, while the invention has been described with reference to particular embodiments, modifications can be made thereto without departing from the scope of the invention. Note also that the term "including" as used herein is intended to be inclusive, i.e. "including but not limited to."

---

APPENDIX A

%Setting threshold for find RV
max_rv=max(rv);
mn_rv=mean(rv);
thshld_rv=0.55*(max_rv-mn_rv)+mn_rv; %threshold
I find where the RV crosses the threshold
%Finding when RV crosses threshold
ndx=find(rv>thshld_rv);
dndx=diff([0; ndx]);
sndx=find(dndx>10);
strt_ndx=ndx(sndx);
dndx=diff([ndx; length(rv)]);
endx=find(dndx>10);
end_ndx=ndx(endx);
I find the maximum signal when the V channel crosses the threshold, and call that my ndx
%Finding maximum for index of RV
ndx_rv=zeros(length(strt_ndx),1);
for i=1:length(strt_ndx)
    [jnk,mx_ndx]=max(rv(strt_ndx(i):end_ndx(i)));
    ndx_rv(i)=strt_ndx(i)+mx_ndx-1;
end
Make sure that each V event captures based on size of signal
%Making sure caption occurred
bad_ndx=[ ];
if ndx_lv(end)+25>length(lv)
    ndx_lv(end)=[ ];
end
for i=1:length(ndx_lv)
    mx_lv=max(lv(ndx_lv(i):ndx_lv(i)+12));

-continued

APPENDIX A

```
        if mx_lv<69
            bad_ndx=[bad_ndx i];
        end
    end
    ndx_lv(bad_ndx)=[ ];
    This next section aligns the LV with the RV to match sure they are matched with eachother
    %Making sure LV and RV are same length
    if ~isempty(ndx_lv) && ~isempty(ndx_rv)
        if length(ndx_rv)~=length(ndx_lv)
            while ndx_rv(1)<ndx_lv(1)
                ndx_rv(1)=[ ];
            end
            while ndx_lv(end)>ndx_rv(end)
                ndx_lv(end)=[ ];
            end
        end
    end
    if length(ndx_rv)~=1ength(ndx_lv)
        %disp('error: RV ~= LV: LV')
        %Removing T waves from RV ndx
        diff_rv=diff(ndx_rv);
        diff_ndx=find(diff_rv<100);
        ddndx=diff([0;diff_ndx]);
        diff_ndx=diff_ndx(ddndx~=1);
        ndx_rv(diff_ndx+1)=[ ];
        %Aligning RV with LV indices
        if length(ndx_rv)<length(ndx_lv)
            tmp_ndx=zeros(length(ndx_rv),1);
            bad_ndx=[ ];
            for i=1:length(ndx_rv)
                tmp=find(ndx_lv>ndx_rv(i)-56 & ndx_lv<ndx_rv(i)+90);
                if ~isempty(tmp)
                    if length(tmp)>1
                        tmp2=ndx_lv(tmp)-ndx_rv(i);
                        [jnk,tmp3],=min(abs(tmp2));
                        tmp=tmp(tmp3);
                    end
                    tmp_ndx(i),=ndx_lv(tmp);
                else
                    bad_ndx=[bad_ndx i];
                end
            end
            ndx_rv(bad_ndx)=[ ];
            ndx_lv=tmp_ndx;
            ndx_lv(ndx_lv==0)=[ ];
        elseif length(ndx_rv)>length(ndx_lv)
            tmp_ndx=zeros(length(ndx_lv),1);
            bad_ndx=[ ];
            for i=1:length(ndx_lv)
                tmp=find(ndx_rv>ndx_lv(i)-80 & ndx_rv<ndx_lv(i)+80);
                if ~isempty(tmp)
                    if length(tmp)>1
                        tmp2=ndx_rv(tmp)-ndx_lv(i);
                        [jnk,tmp3]=min(abs(tmp2));
                        tmp=tmp(tmp3);
                    end
                    tmp_ndx(i)=ndx_rv(tmp);
                else
                    bad_ndx=[bad_ndx i];
                end
            end
            ndx_lv(bad_ndx)=[ ];
            ndx_rv=tmp_ndx;
            ndx_rv(ndx_rv==0)=[ ];
        end
    end
```

What is claimed is:

1. A system for estimating cardiac pressure within a patient using an implantable medical device for implant within a patient, the system comprising:
   an immittance detection system operative to detect a value representative of electrical immittance within the heart of the patient;
   an immittance-based electrical conduction delay estimation unit operative to estimate an electrical conduction delay in the heart of the patient from the value representative of immittance; and
   a conduction delay-based cardiac pressure estimation unit operative to estimate cardiac pressure within the patient from the estimated electrical conduction delay;
   a controller configured to at least one of, based at least in part on the estimated cardiac pressure:
   generate instructions for therapy to at least one end user,
   automatically deliver medication using a drug pump, or
   automatically adjust pacing parameters of the implantable medical device.

2. A system for estimating cardiac pressure within a patient using an implantable medical device for implant within a patient, the system comprising:
   an impedance/admittance measuring circuit configured to detect a value representative of electrical immittance within the heart of the patient;
   a controller configured to:
   estimate an electrical conduction delay in the heart of the patient from the value representative of immittance;
   estimate cardiac pressure within the patient from the estimated electrical conduction delay, and
   at least one of, based at least in part on the estimated cardiac pressure:
   generate instructions for therapy to at least one end user,
   automatically delivery medication using a drug pump, or
   automatically adjust pacing parameters of the implantable medical device.

3. The system of claim 2 wherein the impedance/admittance measuring circuit is configured to detect the value representative of electrical immittance by:
   detecting a value representative of electrical admittance; and
   converting the value representative of electrical admittance into a value representative of electrical impedance.

4. The system of claim 2 wherein the impedance/admittance measuring circuit is configured to detect the value representative of electrical immittance by:
   detecting a value representative of electrical impedance; and
   converting the value representative of electrical impedance into a value representative of electrical admittance.

5. The system of claim 2 wherein the impedance/admittance measuring circuit is configured to detect the value representative of electrical immittance by:
   measuring a raw impedance signal ($Z_0$) along at least one sensing vector passing through the heart of a patient in which the device is implanted; and
   determining an average impedance value (Z) from the raw impedance signal ($Z_0$).

6. The system of claim 5 wherein the controller is configured to estimate electrical conduction delay from the average impedance value (Z) by applying conversion values to the average impedance values to estimate the conduction delay.

7. The system of claim 6 wherein applying the conversion values to the average impedance to estimate the conduction delay includes calculating:

$$\text{Delay} = \alpha * Z^2 + \beta * Z + \delta$$

where $\alpha$, $\beta$ and $\delta$ are the conversion factors and wherein Z represents average impedance along a given vector passing through the heart of the patient.

8. The system of claim 6 wherein applying the conversion values to the average impedance to estimate the conduction delay includes calculating:

$$\text{Delay} = \alpha_1 * Z_1^2 + \beta_1 * Z_1 + \alpha_2 * Z_2^2 + \beta_2 * Z_2 + \delta$$

where $\alpha_1$, $\beta_1$, $\alpha_2$, $\beta_2$ and $\delta$ are the conversion factors and wherein $Z_1$ represents average impedance along a first vector passing through the heart of the patient and $Z_2$ represents average impedance along a second, different vector passing through the heart of the patient.

9. The system of claim 6 further including an external programmer operable to determine the conversion factors for converting average impedance values to delay values for the particular patient.

10. The system of claim 3 wherein a value representative of electrical admittance is detected by:
    measuring a raw admittance signal ($Y_0$) along at least one sensing vector passing through the heart of a patient in which the device is implanted; and
    determining the average admittance value (Y) from the raw admittance signal ($Y_0$).

11. The system of claim 10 wherein the electrical conduction delay is estimated from the average admittance value by:
    determining conversion factors for converting average admittance values to delay values within the patient; and
    applying the conversion values to the average admittance value to estimate the conduction delay.

12. The system of claim 11 wherein applying the conversion values to the average admittance value to estimate the conduction delay includes calculating:

$$\text{Delay} = \alpha * Y^2 + \beta * Y + \delta$$

where $\alpha$, $\beta$ and $\delta$ are the conversion factors and wherein Y represents average admittance along a given vector passing through the heart of the patient.

13. The system of claim 12 wherein applying the conversion values to average admittance value to estimate the conduction delay includes calculating:

$$\text{Delay} = \alpha_1 * Y_1^2 + \beta_1 * Y_1 + \alpha_2 * Y_2^2 + \beta_2 * Y + \delta$$

where $\alpha_1$, $\beta_1$, $\alpha_2$, $\beta_2$ and $\delta$ are the conversion factors and wherein $Y_1$ represents average admittance along a first vector passing through the heart of the patient and $Y_2$ represents average admittance along a second, different vector passing through the heart of the patient.

14. The system of claim 11 further including an external programmer operable to determine the conversion factors for converting average admittance values to delay values for the particular patient.

15. The system of claim 2 wherein the cardiac pressure includes left atrial pressure (LAP).

16. The system of claim 2 wherein the controller is configured to estimate cardiac pressure within the patient from the estimated electrical conduction delay by:
    retrieving predetermined conversion factors from a memory of said implantable medical device for converting the conduction delay to cardiac pressure; and
    estimating cardiac pressure within the patient from the electrical conduction delay by applying the conversion factors to the conduction delay.

17. The system of claim 16 wherein retrieving predetermined conversion factors includes retrieving slope and baseline values representative of a linear relationship between cardiac pressure and the conduction delays.

18. The system of claim 16 wherein estimating cardiac pressure includes calculating:

Cardiac Pressure=Delay*Slope+Baseline.

19. The system of claim 18 further includes an external programmer operable to determine the slope and baseline values that are representative of the linear relationship between the conduction delay and cardiac pressure for the particular patient.

20. The system of claim 2 wherein the controller is further configured to control therapy based on the estimated cardiac pressure.

21. The system of claim 2 wherein the controller is further configured to determine a measure of cardiac function based on the estimated cardiac pressure.

22. The system of claim 2 wherein the controller is further configured to track heart failure based on the estimated cardiac pressure.

23. A system for estimating cardiac pressure within a patient using an implantable medical device, the system comprising:
- an electrical immittance detector circuit operative to detect a value representative of electrical immittance within the heart of the patient;
- an immittance-based electrical conduction delay estimation circuit operative to estimate an electrical conduction delay in the heart of the patient from the value representative of immittance;
- a conduction delay-based cardiac pressure estimation circuit operative to estimate cardiac pressure within the patient from the estimated electrical conduction delay; and
- a therapy/warning controller configured to at least one of:
- generate instructions for therapy, based at least in part on the estimated cardiac pressure, to at least one end user,
- automatically deliver medication using a drug pump, based at least in part on the estimated cardiac pressure, or
- automatically adjust pacing parameters of the implantable medical device, based at least in part on the estimated cardiac pressure.

* * * * *